US012636362B2

(12) United States Patent
Lu et al.

(10) Patent No.: US 12,636,362 B2
(45) Date of Patent: May 26, 2026

(54) HUMAN ANTI-VEGFR-2/KDR ANTIBODIES

(71) Applicant: Kadmon Corporation, LLC, Bridgewater, NJ (US)

(72) Inventors: Dan Lu, Montvale, NJ (US); Zhenping Zhu, Woodcliff Lake, NJ (US)

(73) Assignee: Kadmon Corporation, LLC, Morristown, NJ (US)

( * ) Notice: Subject to any disclaimer, the term of this patent is extended or adjusted under 35 U.S.C. 154(b) by 391 days.

(21) Appl. No.: 18/181,640

(22) Filed: Mar. 10, 2023

(65) Prior Publication Data

US 2023/0338524 A1      Oct. 26, 2023

Related U.S. Application Data

(62) Division of application No. 16/799,977, filed on Feb. 25, 2020, now Pat. No. 11,633,475, which is a division of application No. 15/517,778, filed as application No. PCT/US2015/054569 on Oct. 7, 2015, now Pat. No. 10,588,968.

(60) Provisional application No. 62/061,097, filed on Oct. 7, 2014.

(51) Int. Cl.

| | |
|---|---|
| *A61K 39/395* | (2006.01) |
| *A61P 35/00* | (2006.01) |
| *C07K 16/28* | (2006.01) |
| *C07K 16/30* | (2006.01) |
| *C12N 5/10* | (2006.01) |
| *C12N 15/00* | (2006.01) |
| *C12N 15/13* | (2006.01) |
| *C12N 15/79* | (2006.01) |

(52) U.S. Cl.
CPC .......... *A61K 39/3955* (2013.01); *A61P 35/00* (2018.01); *C07K 16/2863* (2013.01); *C07K 2317/33* (2013.01); *C07K 2317/76* (2013.01); *C07K 2317/92* (2013.01); *C12N 5/10* (2013.01); *C12N 15/00* (2013.01); *C12N 15/79* (2013.01); *C12N 2800/00* (2013.01)

(58) Field of Classification Search
CPC ............ A61K 39/3955; C07K 16/2863; C07K 2317/33; C07K 2317/76; C07K 2317/92; C12N 5/10; C12N 15/00; C12N 15/79; C12N 2800/00
See application file for complete search history.

(56) References Cited

U.S. PATENT DOCUMENTS

| | | | |
|---|---|---|---|
| 2005/0147612 A1* | 7/2005 | Yayon ..................... | A61P 27/02 |
| | | | 536/23.53 |
| 2012/0316071 A1 | 12/2012 | Smider et al. | |
| 2013/0011409 A1 | 1/2013 | Shipp et al. | |
| 2016/0237095 A1 | 8/2016 | Kim et al. | |

FOREIGN PATENT DOCUMENTS

| | | |
|---|---|---|
| CN | 101643509 A | 2/2010 |
| JP | 2003310276 A | 11/2003 |
| WO | 2003075840 A2 | 9/2003 |
| WO | 2012004631 A2 | 1/2012 |
| WO | 2013067098 A1 | 5/2013 |
| WO | 2013149219 A2 | 10/2013 |
| WO | 2014055996 A2 | 4/2014 |
| WO | 2014055998 A1 | 4/2014 |
| WO | 2014055999 A2 | 4/2014 |
| WO | WO-2015054317 A1 * | 4/2015 .............. A61P 37/06 |

OTHER PUBLICATIONS

Bendig, M. M., "Humanization of Roden Monoclonal Antibodies by CDR Grafting"; Methods: A Companion to Methods in Enzymology (1995); vol. 8; pp. 83-93.

Colman, P. M., "Effects of Amino Acid Sequence Changes on Antibody-Antigen Interactions"; Research in Immunology (1994); vol. 145; pp. 33-36.

Khantasup, K. et al., "Design and Generation of Humanized Single-Chain Fv Derived from Mouse Hybridoma for Potential targeting Application"; Monoclonal Antibodies in Immuodiagnosis and Immunotherapy (2015); vol. 34:6; pp. 404-417.

Paul, W.E., "Fundamental Immunology"; 3rd Edition (1993); pp. 292-295.

Rudikoff, S. et al., "Single Amino Acid Substitution Altering Antigen-Binding Specificity"; PNAS USA (1982); vol. 79:6; pp. 1979-1983.

* cited by examiner

*Primary Examiner* — Hong Sang
(74) *Attorney, Agent, or Firm* — McNeill PLLC

(57) ABSTRACT

The invention relates to antibodies that bind to VEGFR-2. The antibodies are used for treating neoplastic diseases, hyperproliferative disorders, and angiogenic disorders and can be used alone or in combination with other agents.

6 Claims, 19 Drawing Sheets
Specification includes a Sequence Listing.

```
                          1                            2                         3                       4
Kabat   No.  1 2 3 4 5 6 7 8 9 0 1 2 3 4 5 6 7 8 9 0 1 2 3 4 5    6 7 8 9 0 1 2 3 4 5 A B    6 7 8 9 0 1 2 3
SEQ ID NO.
4            E V Q L L E S G G G L V Q P G G S L R L S C A A S    G F T F S W Y V M G - -     W V R Q A P G K
12           E V Q L L E S G G G L V Q P G G S L R L S C A A S    G F T F S W Y I M L - -     W V R Q A P G K 5                      6                                7                             8
Kabat   No.  4 5 6 7 8 9   0 1 2 A B C 3 4 5 6 7 8 9 0 1 2 3 4 5    6 7 8 9 0 1 2 3 4 5 6 7 8 9 0 1 2 A B C
SEQ ID NO.
4            G L E W V S   S I Y P - - S G G A T N Y A D S V K G    R F T I S R D N S K N T L Y L Q M N S L
12           G L E W V S   S I G S - - - S G G F T D Y A D S V K G  R F T I S R D N S K N T L Y L Q M N S L 9                           10                                1
                                                                                  0
Kabat   No.  3 4 5 6 7 8 9 0 1 2 3 4   5 6 7 8 9 0 A B C D E F G H I J K 1 2    3 4 5 6 7 8 9 0 1 2 3
SEQ ID NO.
4            R A E D T A V Y Y C A R   G N Y F - - - - - - - - - - - D Y       W G Q G T L V T V S S
12           R A E D T A V Y Y C A R   G L A A P - - - - - - - - - - R S       W G R G T L V T V S S
```

| Kabat No. | | |
|---|---|---|
| SEQ ID NO. | FR (Kabat 1–23) ... CDR1 box ... (Kabat 35–37) | |
| 8  | QSVLTQDPA-VSVALGQTVRIHTC   QGDSL-----RSYYAS   WYQ |
| 24 | QSALTQPPS-VSVSPGQTASIHTC   SGDKL-----GDEYAS   WYQ |
| 28 | QYELTQPPS-VSVSPGQTASIHTC   SGDNL-----RHEYSS   WYQ |
| 32 | QSVLTQPPS-VSVSPGQTASIHTC   SGEKL-----GDEYAS   WYQ |
| 36 | QSELTQPPS-VSVSPGQTASIHTC   SGEKL-----GDEYAS   WYQ |
| 40 | QYELTQPPS-VSVSPGQTATIHTC   TGDKL-----GDQFAS   WYQ |
| 44 | QSALTQPPS-VSVSPGHTATIHTC   SGQIL-----GERSAS   WYQ |
| 48 | QSALTQPPS-VSVSPGQTAIIHSC   SGDAL-----GNNYAS   WYQ |
| 16 | QSALTQPPS-VSEAPGQRVTIHSC   SGSTSN-IH-IGNNAVI   WYQ |
| 20 | QSALTQPPS-VSGTPGQRVTIHSC   SGSSSN-IH-IGTYPVN   WYQ |
| 52 | QSALTQPPS-VSEAPGQRVTIHSC   SGSSSN-IH-IGTNTLN   WYQ |
| 56 | QYELTQPPS-VSGTPGQRVTIHSC   SGSTSN-IH-IGNNAVI   WYQ |
| 60 | QSELTQPDS-VSGSPGQSITIHSC   SGSSSN-IL-LGSNTVN   WYQ |
| 64 | QSVLTQPDS-VSGSPGQSITIHSC   SGSSND-----IESNYYV   WYQ |
| 68 | QSELTQPDS-VSGSPGQSITIHSC   SGSSND-IGS-IGSYDYVS   WYQ |
| 72 | QSALTQPAS-MSGSRGSPGQSITIHSC   TGSSHD-VGA-IGAYDYVS   WYK |
| 76 | QSALTQPAS-VSGSPGQSITIHSC   AGTSSD-IGA-IGAYDYVS   WYK |
| 80 | QSVLTQPYS-VSGSPGQSITIHSC   TGSSHD-IGA-IGAYDYVS   WYK |
| 84 | QSVLTQPDS-VSGSPGQSITIHSC   TGSSHD-IGA-IGAYDYVS   WYK |
| 88 | QSALTQPDS-VSGSPGQSITIHSC   TGSSHD-IGA-IGAYDYVS   WYK |
| 92 | QSVLTQPDS-VSGSPGQSITIHSC   TGSSHD-IGA-IGAYDYVS   WYK |
| 96 | QSELTQPDS-VSGSPGQSITIHSC   TGSSHD-IGA-IGAYDYVS   WYK |

Fig. 1B (cont.)

Amino acid sequence alignment by Kabat numbering. FR2 region (Kabat ~38–49), CDR‑L2 region (boxed, Kabat 50–56), and FR3 region (Kabat ~57–80).

| SEQ ID NO: | Kabat 38–49 | CDR‑L2 (50–56) | Kabat 57–80 |
|---|---|---|---|
| 8 | QQKPGQSPLVVIY | QDTNRPS | GIPERFSGSNSGNTATLTISETQA |
| 24 | QQKPGQSPVLVIY | QDNKRPS | GIPERFSGSNSGNTATLTISGTQA |
| 28 | QQRPGQSPVLVIY | QDSKRPS | GIPERFSGSNSGNTATLTISGTQA |
| 32 | QQKPGQSPVLVIY | QDNKRPS | GIPERFSGSNSGNTATLTISGTQA |
| 36 | QQKPGQSPVLVIY | QDNKRPS | GIPERFSGSNSGNTATLTISGTQA |
| 40 | HQKPGQSPILLVLY | QNDKRPS | GIPDRFSGSDSGNTATLTISGAQS |
| 44 | QQRPGQAPVLVIY | QSSQRPS | GIPERFSGSISGNTATLTISETQT |
| 48 | QQKPGQSPVLVIY | QDTKRPS | GIPERFSGSSSGNTATLTISGLQS |
| 16 | QQLPGKAPKLLIY | YDDLLPS | GVSDRFSGSKSGTSASLAISGLQA |
| 20 | QQLPGTAPKLLIY | STDQRPS | GVPDRFSGSNSGNTASLTISGLQS |
| 52 | QQLPGKAPKLLIY | ANNQRPS | GVPDRFSGSRSGTSASLAISGLQS |
| 56 | QQLPGTAPKLLIY | YDDLLPS | GVPDRFSGSKSGNTASLTISGLRS |
| 60 | QQLPGTAPKLLIY | TNSQRPS | GVPDRFSGSKSGNTASLTISGLQP |
| 64 | QQLPGRAPKLLIY | TNNQRPS | GVADRFSGSKSGNTASLTISGLQP |
| 68 | QQHPGKAPRLLIY | DVNNRPS | GVSDRFSGSKSGNTASLTISGLQP |
| 72 | QYHPGKAPKFILY | DVYNRPS | GVSDRFSGSKSGNTASLTISGLQP |
| 76 | HHLPGNAPKFILY | DVYNRPS | GVSDRFSGSKSGNTASLTISGLQP |
| 80 | HHLPGNAPKFILY | DVYNRPS | GVSDRFSGSKSGNTASLTISGLQP |
| 84 | HHLPGNAPKFILY | DVYNRPS | GVSDRFSGSKSGNTASLTISGLQP |
| 88 | HHLPGNAPKFILY | DVYNRPS | GVSDRFSGSKSGNTASLTISGLQP |
| 92 | HHLPGNAPKFILY | DVYNRPS | GVSDRFSGSKSGNTASLTISGLQP |
| 96 | HHLPGNAPKFILY | DVYNRPS | GVSDRFSGSKSGNTASLTISGLQP |

| Kabat No. SEQ ID NO: | 1 2 3 4 5 6 7 8 | 9 0 1 2 3 4 5 A B C D E F 6 7 | 8 9 0 1 2 3 4 5 6 A 7 8 9 |
|---|---|---|---|
| 8 | M D E A D Y Y C | Q A W D S N T · · · · · · A V | F G G G T K L T V L G Q P |
| 24 | M D E A D Y Y C | Q A W D S S T · · · · · · V V | F G G G T K L T V L G Q P |
| 28 | L D E A D Y Y C | Q A W G S S T · · · · · · V V | F G G G T K L T V L G Q P |
| 32 | M D E A D Y Y C | Q A W D S S T · · · · · · L L | F G G G T K L T V L G Q P |
| 36 | M D E A D Y Y C | Q A W D S S T · · · · · · L L | F G G G T K L T V L G Q P |
| 40 | M D E A H Y Y C | Q A W D F S S · · · · · · A L | F G G G T K L T V L G Q P |
| 44 | I D E A D Y Y C | Q T W D T S · · · · · · · I L | F G G G T K V T V L S Q P |
| 48 | M D E A D Y Y C | Q T W D R N T P · · · · · Y V | F G A G T K V T V L G Q P |
| 16 | E D E A D Y Y C | A S W D D N L N G · · · · P L | F G G G T K L T V L R Q P |
| 20 | M D E A D Y Y C | Q A W D S S T · · · · · · V V | F G G G T K L T V L G Q P |
| 52 | D D E A D Y Y C | A T W D D S L I G · · · · P V | F G G G T K L T V L G Q P |
| 56 | E D E A D Y Y C | A S W D D N L N G · · · · P L | F G G G T K L T V L R Q P |
| 60 | E D E A D Y Y C | A A W D D S L N G · · · · W V | F G G G T K L T V L G Q P |
| 64 | E D E A D Y Y C | A S W D D S L S G · · · · V V | F G G G T K L T V L R Q P |
| 68 | D D E A D Y Y C | M S Y T I T A · · · · · · L L | F G G G T R V T V L S Q P |
| 72 | D D E A D Y F C | M S Y T I T T · · · · · · L L | F G T G T R V T V L S Q P |
| 76 | D D E A D Y F C | M S Y T I T T · · · · · · L L | F G T G T R V T V L S Q P |
| 80 | D D E A D Y F C | M S Y T I T T · · · · · · L L | F G T G T R V T V L S Q P |
| 84 | D D E A D Y F C | M S Y T I T T · · · · · · L L | F G T G T R V T V L S Q P |
| 88 | D D E A D Y F C | M S Y T I T T · · · · · · L L | F G T G T R V T V L S Q P |
| 92 | D D E A D Y F C | M S Y T I T T · · · · · · L L | F G T G T R V T V L S Q P |
| 96 | D D E A D Y F C | M S Y T I T T · · · · · · L L | F G T G T R V T V L S Q P |

Fig. 1B (cont.)

| Kabat No. | | | | | | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| SEQ ID NO: | 1 | 2 | 3 | 4 | 5 | 6 | 7 | 8 | 9 | 0 | 1 | 2 | 3 | 4 | 5 | 6 | 7 | 8 | 9 | 0 | 1 | 2 | 3 | | 4 | 5 | 6 | 7 | | 8 | 9 | 0 | 1 | 2 | 3 | 4 | | 5 | 6 | 7 | | | | | |
| 100 | D I Q M T Q S P G T L S L S P G E R A T L S C | | | | | | | | | | | | | | | | | | | | | | | | R A S Q S | | | | V S S S Y L A | | | | | | | | W Y Q | | | | | | |
| 104 | D I Q M T Q S P G T L S L S V L P G E R A T L S C | | | | | | | | | | | | | | | | | | | | | | | | R A S E R | | | | I S S N Y L M | | | | | | | | W F Q | | | | | | |
| 108 | D I Q M T Q S P A T L S L S P G E R A T L S C | | | | | | | | | | | | | | | | | | | | | | | | R A S Q S I | | | | I S S N Y L A | | | | | | | | W Y Q | | | | | | |
| 112 | D I Q M T Q S P G T L S L S P G E R A T L S C | | | | | | | | | | | | | | | | | | | | | | | | R A S Q S | | | | R S S G Y L S | | | | | | | | W F Q | | | | | | |
| 116 | D I Q M T Q S P G T L S L S P G E R A T L S C | | | | | | | | | | | | | | | | | | | | | | | | R A S Q S | | | | V S S N Y L G | | | | | | | | W Y Q | | | | | | |
| 120 | D I Q M T Q S P G T L S L S P G E R A T L S C | | | | | | | | | | | | | | | | | | | | | | | | R A S Q S | | | | V S S N Y L A | | | | | | | | W Y Q | | | | | | |
| 124 | D I Q M T Q S P G T L S L S P G E R A T L S C | | | | | | | | | | | | | | | | | | | | | | | | R A S Q S | | | | V S S N Y L A | | | | | | | | W Y Q | | | | | | |
| 128 | D I Q M T Q S P G T L S L S P G E R A T L S C | | | | | | | | | | | | | | | | | | | | | | | | R A S Q N | | | | V S S W Y L A | | | | | | | | W Y Q | | | | | | |
| 132 | D I Q M T Q S P G T L S L S P G E R A T L S C | | | | | | | | | | | | | | | | | | | | | | | | R A S Q S | | | | V G S S Y L A | | | | | | | | W Y Q | | | | | | |
| 136 | D I Q M T Q S P G T L S L S P G E R A T L S C | | | | | | | | | | | | | | | | | | | | | | | | R A S Q S | | | | V S S S Y L A | | | | | | | | W Y Q | | | | | | |
| 140 | D I Q M T Q S P G T L S L S P G E R A T L S C | | | | | | | | | | | | | | | | | | | | | | | | R A S Q S | | | | V S S S Y L A | | | | | | | | W Y Q | | | | | | |
| 144 | D I Q M T Q S P G T L S L S P G E R A T L S C | | | | | | | | | | | | | | | | | | | | | | | | R A S Q S | | | | V S S S Y L A | | | | | | | | W Y Q | | | | | | |
| 148 | D I Q M T Q S P G T L S L S P G E G A T L S C | | | | | | | | | | | | | | | | | | | | | | | | R A S Q S | | | | V S S N Y F G | | | | | | | | W Y Q | | | | | | |
| 152 | D I Q M T Q S P G T L S L S P G D R A T L S C | | | | | | | | | | | | | | | | | | | | | | | | R A S Q S | | | | V S S N Y L A | | | | | | | | W Y Q | | | | | | |
| 156 | D I Q M T Q S P G T L S L S P G E R A T L S C | | | | | | | | | | | | | | | | | | | | | | | | R A S Q S | | | | V S S N Y L A | | | | | | | | W Y Q | | | | | | |
| 160 | D I Q M T Q S P A T L S L S P G E R A T L S C | | | | | | | | | | | | | | | | | | | | | | | | R A S Q S | | | | L N N N Y L A | | | | | | | | W Y Q | | | | | | |
| 164 | D I Q M T Q S P G T L S L S P G E R A T L S C | | | | | | | | | | | | | | | | | | | | | | | | R A S Q S | | | | V S S N Y L A | | | | | | | | W Y Q | | | | | | |
| 168 | D I Q M T Q S P A T L S V S P G E R A T L S C | | | | | | | | | | | | | | | | | | | | | | | | R A S H S | | | | V S S D Y L A | | | | | | | | W Y Q | | | | | | |
| 172 | D I Q M T Q S P G T L S L S P G E R A T L S C | | | | | | | | | | | | | | | | | | | | | | | | R A S H S | | | | V S S D Y L A | | | | | | | | W Y Q | | | | | | |
| 176 | D I Q M T Q S P D T L S L S V S P G E R A T L S C | | | | | | | | | | | | | | | | | | | | | | | | R A S H S | | | | V S S D Y L A | | | | | | | | W Y Q | | | | | | |
| 180 | D I Q M T Q S P D T L S L S P G E R A T L S C | | | | | | | | | | | | | | | | | | | | | | | | R A S H S | | | | V S S D Y L A | | | | | | | | W Y Q | | | | | | |
| 184 | D I Q M T Q S P D T L S L S P G E R A T L S C | | | | | | | | | | | | | | | | | | | | | | | | R A S H S | | | | V S S D Y L A | | | | | | | | W Y Q | | | | | | |

Fig. 1C

| Kabat No.<br>SEQ ID NO: | 4<br>8 9 0 1 2 3 4 5 6 7 8 9 | 5<br>0 1 2 3 4 5 6 | 6 7 8<br>7 8 9 0 1 2 3 4 5 6 7 8 9 0 1 2 3 4 5 6 7 8 9 0 |
|---|---|---|---|
| 100 | Q K P G Q A P R L L M Y | G A S S R A T | G F P D R F S G S G S G T D F S L T I S R L E P |
| 104 | Q K P G Q A P R L L M Y | G A S I R A T | G I P D R F S G S E S G T D F T L T I S R V E P |
| 108 | Q R P G Q A P R L L I Y | G A S S R S T | G T P D R F S G S G S G T D F T L T I S R L E P |
| 112 | Q K P G Q A P R L L I Y | G A S T R A T | G T P A R F S G S G S G T D F T L T I D R L E S |
| 116 | Q K P G Q A P R L L I Y | G A S S R A T | G I P D R F S G S G S G T D F T L T I S R L E P |
| 120 | Q K P G Q A P R L L I Y | G A S S R A T | G I P D R F S G S G S G T D F T L T I S R L E P |
| 124 | Q K P G Q A P R L L I Y | G A S S R A T | G I P D R F S G S G S G T D F S L T I S R L E P |
| 128 | Q K P G Q A P R L L M Y | G A S N R A T | G I P D R F S G S G S G T D F T L T I S R L E P |
| 132 | Q K P G Q A P R L L M Y | G A S S R A T | G F P D R F S G S G S G T D F S L T I S R L E P |
| 136 | Q K P G Q A P R L L M Y | G A S S R A T | G F P D R F S G S G S G T D F S L T I S R L E P |
| 140 | Q K P G R A P R L L M Y | G A S S R A T | G F P D R F S G S G S G T D F S L T I S R L E P |
| 144 | Q K P G Q A P R L L I Y | G A S S R A T | G I P D R F S G S G S G T D Y T L T I N R L E P |
| 148 | Q K P G Q A P R L L I Y | G A S T R A T | G I P P R F S G S G S G T E F T L T I S S V Q S |
| 152 | Q K P G Q A P R L L I Y | G A S S R A T | G I P D R F S G S G S G T D F T L T I S R L E P |
| 156 | Q K P G Q A P R L L I Y | G A S S R A T | G I P D R F S G S G S G T D F S L T I S R L E P |
| 160 | Q K P G Q A P R V L I Y | G A S T R A T | G I P D R F T G S G S G T D F T L T I S R L E P |
| 164 | Q K P G Q A P R L L M Y | G A S T R A T | G I P A R F S G S G S G T E F T L T I S S L Q S |
| 168 | Q K P G R A P R L L M Y | G A S S R A T | G F P D R F S G S G S G T D F S L T I S R L E P |
| 172 | Q K P G R A P R L L M Y | G A S S R A T | G F P D R F S G S G S G T D F S L T I S R L E P |
| 176 | Q K P G R A P R L L M Y | G A S S R A T | G F P D R F S G S G S G T D F S L T I S R L E P |
| 180 | Q K P G R A P R L L M Y | G A S S R A T | G F P D R F S G S G S G T D F S L T I S R L E P |
| 184 | Q K P G R A P R L L M Y | G A S S R A T | G F P D R F S G S G S G T D F S L T I S R L E P |

Fig. 1C (cont.)

| Kabat No. | 1 2 3 4 5 6 7 8 | 9 0 1 2 3 4 5 A B C D E F 6 7 | 8 9 0 1 2 3 4 5 6 7 8 |
|---|---|---|---|
| SEQ ID NO: | | | |
| 100 | E D F A V Y Y C | Q Q F D S S P       P T | F F G G G T K V E I K R |
| 104 | E D F A V Y Y C | Q Q Y Y S S P       L T | F F G G G T K V E M K R |
| 108 | E D F A I Y Y C | Q Q F D T L P       I T | F F G Q G T R L D E I K R |
| 112 | E D F A V Y F C | Q Q Y G S S T       I T | F F G G G T K V E I K R |
| 116 | E D F A V Y Y C | Q Q F D N L P       V T | F F G Q G T K V E M K R |
| 120 | E D F A V Y Y C | Q Q F D T S P       L T | H I G G G T R V D E I K R |
| 124 | E D S A V Y Y C | Q Q F D S S P       L S | F F G G G T K V E I K R |
| 128 | E D S A V Y Y C | Q Q F D S S P       L T | H I G G G T K V E I K R |
| 132 | E D F A V Y Y C | Q Q F D S S P       P T | F F G G G T K V E I K R |
| 136 | E D F A V Y Y C | Q Q F D S S P       P T | F F G G G T K V E I K R |
| 140 | E D F A V Y Y C | Q Q F G S S P       P T | F F G G G T K V E I K R |
| 144 | E D F A I Y Y C | Q Q F D N W P P   P   Y T | F F G Q G T K L E I K R |
| 148 | E D F A V Y Y C | Q Q F D S S P   P   W T | F F G Q G T K V E I K R |
| 152 | E D S A V Y Y C | Q Q F D S S P       L T | F F G G G T R L E I K R |
| 156 | E D S A V Y Y C | Q Q F D S S P       L S | F F G G G T K V E I K R |
| 160 | E D S A V Y Y C | Q Q F D S S P       L S | F F G G G T K V E I K R |
| 164 | E D F A M Y Y C | Q Q F D S S P       P T | F F G G G T K V E I K R |
| 168 | E D F A M Y Y C | Q Q F D S S P       P T | F F G G G T K V E I K R |
| 172 | E D F A V Y Y C | Q Q F D S S P       P T | F F G G G T K V E I K R |
| 176 | E D F A V Y Y C | Q Q F D S S P       P T | F F G G G T K V E I K R |
| 180 | E D F A V Y Y C | Q Q F D S S P       P T | F F G G G T K V E I K R |
| 184 | E D F A V Y Y C | Q Q F D S S P       P T | F F G G G T R I D I K R |

Fig. 1C (cont.)

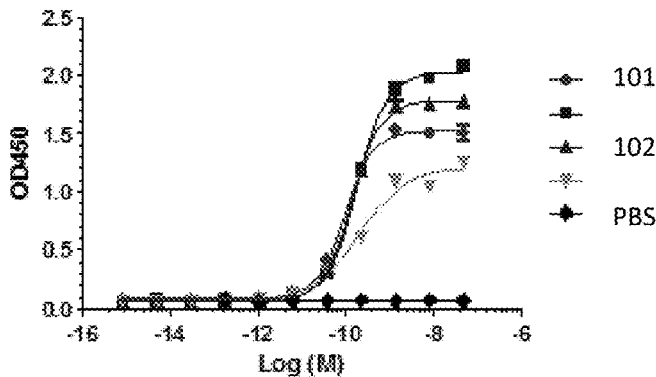
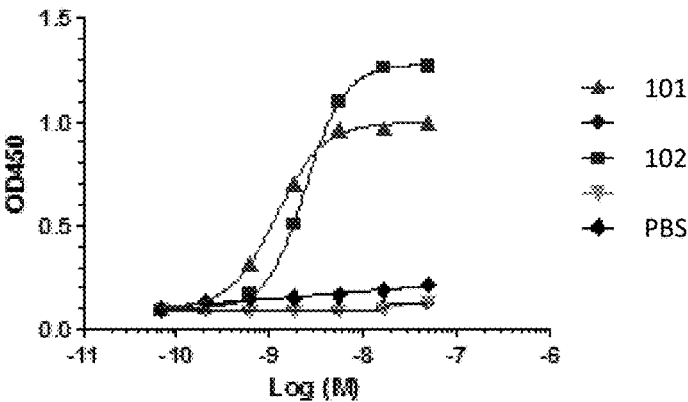
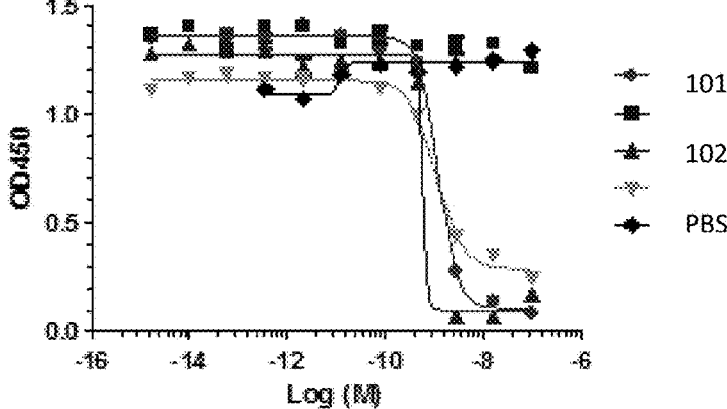
Fig. 2

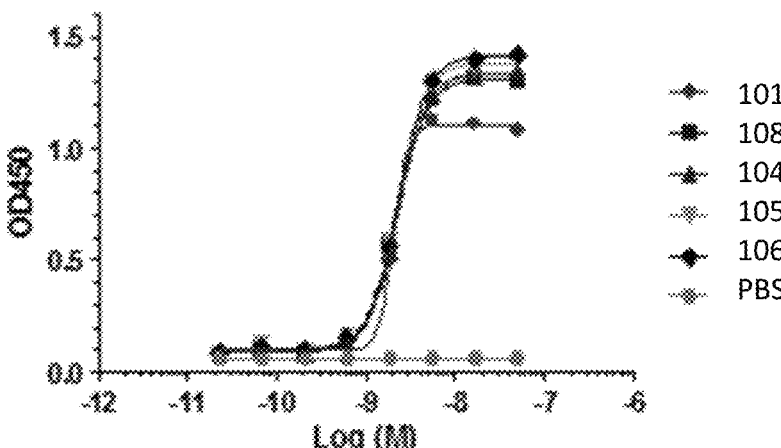
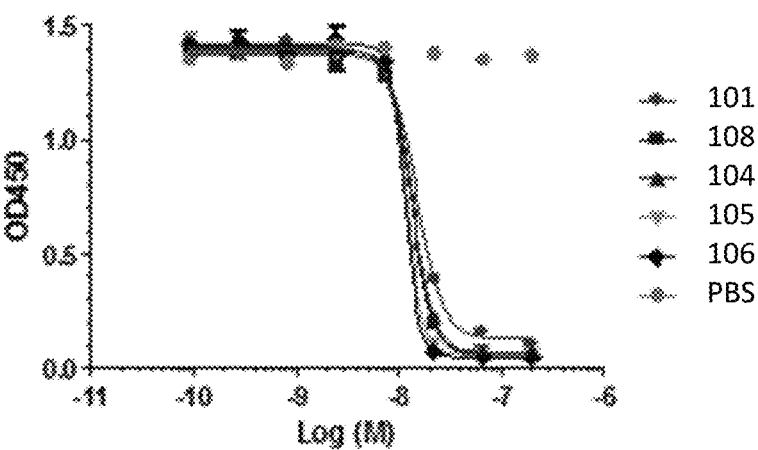
Fig. 4

Block 1

```
Kabat                        1                                                 3                       4
No.      1 2 3 4 5 6 7 8 9 0 1 2 3 4 5   2 0 1 2 3 4 5   6 7 8 9 0 1 2 3 4 5 A B   6 7 8 9 0 1 2 3
SEQ ID NO.
   4     E V Q L L E S G G G L V Q P G   G S L R L S C A A S   G F T F S W Y V M G - -   W V R Q A P G K
 200     E V Q L L E S G G G L V Q P G   G S L R L S C A A S   G F T F S W Y V M G - -   W V R Q A P G K
 208     E V Q L L E S G G G L V Q P G   G S L R L S C A A S   G F T F S W Y V M S - -   W V R Q A P G K
 216     E V Q L L E S G G G L V Q P G   G S L R L S C A A S   G F T F S W Y V M G - -   W V R Q A P G K
 224     E V Q L L E S G G G L V Q P G   G S L R L S C A A S   G F T F S W Y V M G - -   W V R Q A P G K
 232     E V Q L L E S G G G L V Q P G   G S L R L S C A A S   G F T F S W Y V M G - -   W V R Q A P G K
```

Block 2

```
Kabat                      5                             6                                     7                                     8
No.      4 5 6 7 8 9   0 1 2 A B C 3 4 5   6 7 8 9 0 1 2 3 4 5   6 7 8 9 0 1 2 3 4 5   6 7 8 9 0 1 2 A B C
SEQ ID NO.
   4     G L E W V S   S I Y P - - S G G A T N Y A D S V K G   R F T I S R D N S K N T L Y L Q M N S L
 200     G L E W V S   S I Y P - - Q G G A T S Y A D S V K G   R F T I S R D N S K N T L Y L Q M N S L
 208     G L E W V S   S I Y P - - Q G G A T N Y A D S V K G   R F T I S R D N S K N T L Y L Q M N S L
 216     G L E W V S   S I Y P - - S G G A T N Y A D S V K G   R F T I S R D N S K N T L Y L Q M N S L
 224     G L E W V S   S I Y P - - S G G A T N Y A D S V K G   R F T I S R D N S K N T L Y L Q M N S L
 232     G L E W V S   S I Y P - - S G G A T N Y A D S V K G   R F T I S R D N S K N T L Y L Q M N S L
```

Block 3

```
Kabat                      9                 1                                       1
No.      3 4 5 6 7 8 9 0 1 2 3 4   5 6 7 8 9 0 A B C D E F G H I J K 1 2   3 4 5   6 7 8 9 0 1 2 3
SEQ ID NO.
   4     R A E D T A V Y Y C A R   G N Y F - - - - - - - - - - - - - - D Y   W G Q G T L V T T V S S
 200     R A E D T A V Y Y C A R   G N Y F - - - - - - - - - - - - - - D Y   W G Q G T L V T T V S S
 208     R A E D T A V Y Y C A R   G N Y F - - - - - - - - - - - - - - D Y   W G Q G T L V T T V S S
 216     R A E D T A V Y Y C A R   G N Y L - - - - - - - - - - - - - - D Y   W G Q G T L V T T V S S
 224     R A E D T A V Y Y C A R   G P Y L - - - - - - - - - - - - - - D Y   W G Q G T L V T T V S S
 232     R A E D T A V Y Y C A R   G S Y L - - - - - - - - - - - - - - D Y   W G Q G T L V T T V S S
```

Fig. 6A

Panel 1

| Kabat No. | | | |
|---|---|---|---|
| SEQ ID NO: | | | |
| 160 | DIQMTQSPGTLSLSPGEGATLSC | RASQS | VSSNYFG WYQ |
| 204 | DIQMTQSPGTLSLSPGEGATLSC | RASQS | VSSNYFG WYQ |
| 212 | DIQMTQSPGTLSLSPGEGATLSC | RASQS | VSSNYFG WYQ |
| 220 | DIQMTQSPGTLSLSPGEGATLSC | RASQS | VSSNYFG WYQ |
| 228 | DIQMTQSPGTLSLSPGEGATLSC | RASQS | VSSNYFG WYQ |
| 236 | DIQMTQSPGTLSLSPGEGATLSC | RASQS | VSSNYFG WYQ |

Panel 2

| Kabat No. | | | |
|---|---|---|---|
| SEQ ID NO: | | | |
| 160 | QKPGQAPRLLIY | GASSRAT | GIPDRFSGSGSGTDFTLTISRLEEP |
| 204 | QKPGQAPRLLIY | GASSRAT | GIPDRFSGSGSGTDFTLTISRLEEP |
| 212 | QKPGQAPRLLIY | GASSRAT | GIPDRFSGSGSGTDFTLTISRLEEP |
| 220 | QKPGQAPRLLIY | GASSRAT | GIPDRFSGSGSGTDFTLTISRLEEP |
| 228 | QKPGQAPRLLIY | GASSRAT | GIPDRFSGSGSGTDFTLTISRLEEP |
| 236 | QKPGQAPRLLIY | GASSRAT | GIPDRFSGSGSGTDFTLTISRLEEP |

Panel 3

| Kabat No. | | | |
|---|---|---|---|
| SEQ ID NO: | | | |
| 160 | EDSAVYYC | QQFDSSP LT | FGGGTKVEIKR |
| 204 | EDSAVYYC | QQFDSLP LT | FGGGTKVEIKR |
| 212 | EDSAVYYC | QQHDSSP LS | FGGGTKVEIKR |
| 220 | EDSAVYYC | QQFDSSP LS | FGGGTKVEIKR |
| 228 | EDSAVYYC | QQFDSSP LT | FGGGTKVEIKR |
| 236 | EDSAVYYC | QQFDSSP LT | FGGGTKVEIKR |

Fig. 6B

Binding to hVEGFR2 on HUVEC and KDR-PAE

Binding to mVEGFR2 on MS1 cells

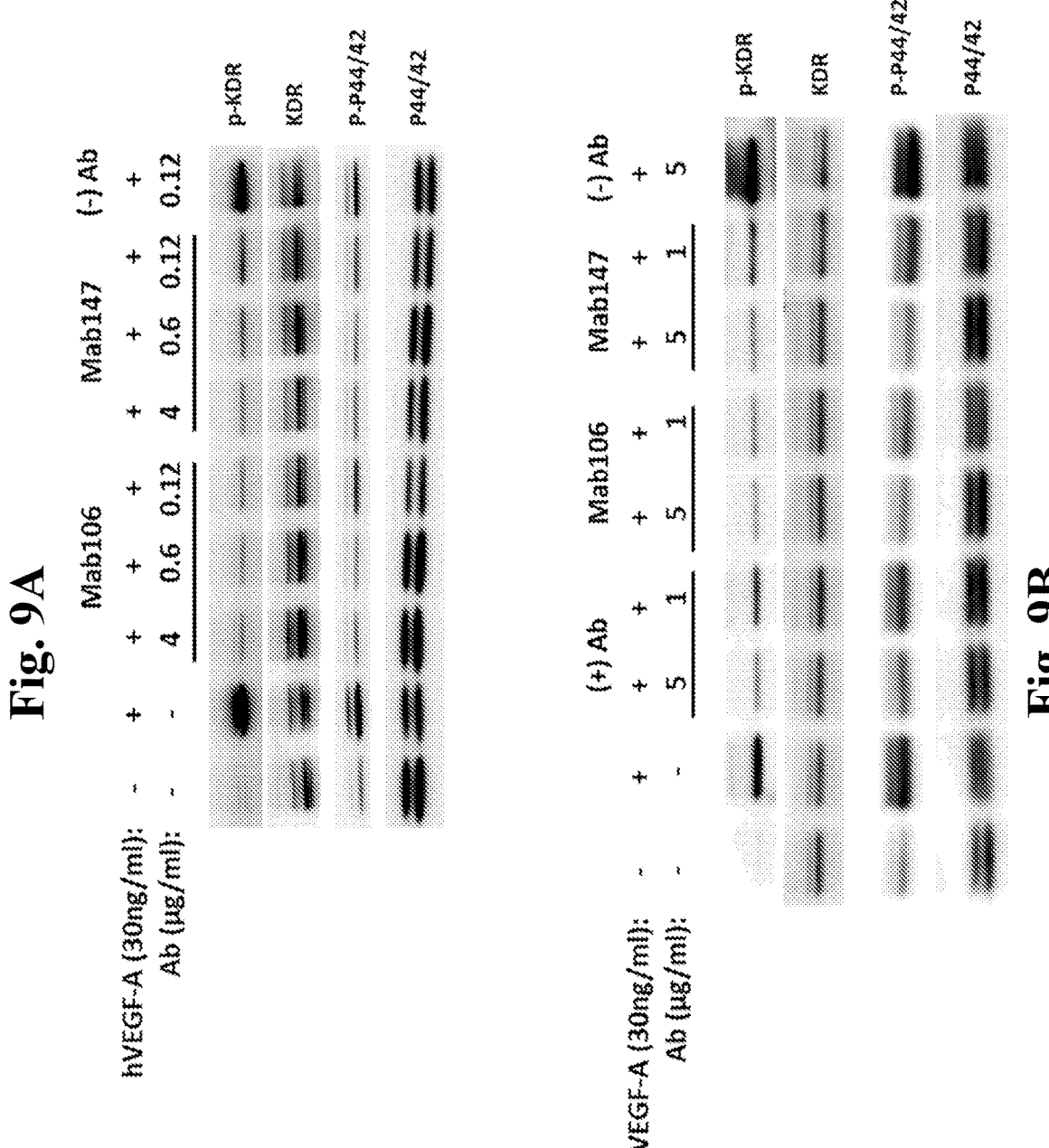

50 ng/ml VEGF (up)
100 ng/ml VEGF (low)

Eoma

| color | 10ug/ml of Ab |
|---|---|
| red | 2' Ab only |
| Fuchsia | Mab147 |
| Lime | (+), anti-mVEGFR2-1 |
| Aqua | (+), anti-mVEGFR2-2 |

SEQUENCE LISTING

```
Sequence total quantity: 252
SEQ ID NO: 1            moltype = AA   length = 7
FEATURE                 Location/Qualifiers
REGION                  1..7
                        note = Human antibody library
source                  1..7
                        mol_type = protein
                        organism = synthetic construct
SEQUENCE: 1
GFTFSWY                                                      7

SEQ ID NO: 2            moltype = AA   length = 7
FEATURE                 Location/Qualifiers
REGION                  1..7
                        note = Human antibody library
source                  1..7
                        mol_type = protein
                        organism = synthetic construct
SEQUENCE: 2
IYPSGGA                                                      7

SEQ ID NO: 3            moltype = AA   length = 6
FEATURE                 Location/Qualifiers
REGION                  1..6
                        note = Human antibody library
source                  1..6
                        mol_type = protein
                        organism = synthetic construct
SEQUENCE: 3
GNYFDY                                                       6

SEQ ID NO: 4            moltype = AA   length = 115
FEATURE                 Location/Qualifiers
REGION                  1..115
                        note = Human antibody library
source                  1..115
                        mol_type = protein
                        organism = synthetic construct
SEQUENCE: 4
EVQLLESGGG LVQPGGSLRL SCAASGFTFS WYVMGWVRQA PGKGLEWVSS IYPSGGATNY  60
ADSVKGRFTI SRDNSKNTLY LQMNSLRAED TAVYYCARGN YFDYWGQGTL VTVSS       115

SEQ ID NO: 5            moltype = AA   length = 11
FEATURE                 Location/Qualifiers
REGION                  1..11
                        note = Human antibody library
source                  1..11
                        mol_type = protein
                        organism = synthetic construct
SEQUENCE: 5
QGDSLRSYYA S                                                 11

SEQ ID NO: 6            moltype = AA   length = 7
FEATURE                 Location/Qualifiers
REGION                  1..7
                        note = Human antibody library
source                  1..7
                        mol_type = protein
                        organism = synthetic construct
SEQUENCE: 6
QDTNRPS                                                      7

SEQ ID NO: 7            moltype = AA   length = 9
FEATURE                 Location/Qualifiers
REGION                  1..9
                        note = Human antibody library
source                  1..9
```

```
                              mol_type = protein
                              organism = synthetic construct
SEQUENCE: 7
QAWDSNTAV                                                          9

SEQ ID NO: 8          moltype = AA   length = 109
FEATURE               Location/Qualifiers
REGION                1..109
                      note = Human antibody library
source                1..109
                      mol_type = protein
                      organism = synthetic construct
SEQUENCE: 8
QSVLTQDPAV SVALGQTVRI TCQGDSLRSY YASWYQQKPG QSPLVVIYQD TNRPSGIPER   60
FSGSNSGNTA TLTISETQAM DEADYYCQAW DSNTAVFGGG TKLTVLGQP              109

SEQ ID NO: 9          moltype = AA   length = 7
FEATURE               Location/Qualifiers
REGION                1..7
                      note = Human antibody library
source                1..7
                      mol_type = protein
                      organism = synthetic construct
SEQUENCE: 9
GFTFSWY                                                            7

SEQ ID NO: 10         moltype = AA   length = 6
FEATURE               Location/Qualifiers
REGION                1..6
                      note = Human antibody library
source                1..6
                      mol_type = protein
                      organism = synthetic construct
SEQUENCE: 10
GSSGGF                                                             6

SEQ ID NO: 11         moltype = AA   length = 7
FEATURE               Location/Qualifiers
REGION                1..7
                      note = Human antibody library
source                1..7
                      mol_type = protein
                      organism = synthetic construct
SEQUENCE: 11
GLAAPRS                                                            7

SEQ ID NO: 12         moltype = AA   length = 116
FEATURE               Location/Qualifiers
REGION                1..116
                      note = Human antibody library
source                1..116
                      mol_type = protein
                      organism = synthetic construct
SEQUENCE: 12
EVQLLESGGG LVQPGGSLRL SCAASGFTFS WYIMLWVRQA PGKGLEWVSS IGSSGGFTDY   60
ADSVKGRFTI SRDNSKNTLY LQMNSLRAED TAVYYCARGL AAPRSWGRGT LVTVSS      116

SEQ ID NO: 13         moltype = AA   length = 13
FEATURE               Location/Qualifiers
REGION                1..13
                      note = Human antibody library
source                1..13
                      mol_type = protein
                      organism = synthetic construct
SEQUENCE: 13
SGSTSNIGNN AVI                                                     13

SEQ ID NO: 14         moltype = AA   length = 7
FEATURE               Location/Qualifiers
REGION                1..7
                      note = Human antibody library
source                1..7
                      mol_type = protein
                      organism = synthetic construct
SEQUENCE: 14
YDDLLPS                                                            7

SEQ ID NO: 15         moltype = AA   length = 11
FEATURE               Location/Qualifiers
```

-continued

```
REGION                    1..11
                          note = Human antibody library
source                    1..11
                          mol_type = protein
                          organism = synthetic construct
SEQUENCE: 15
ASWDDNLNGP L                                                          11

SEQ ID NO: 16             moltype = AA  length = 113
FEATURE                   Location/Qualifiers
REGION                    1..113
                          note = Human antibody library
source                    1..113
                          mol_type = protein
                          organism = synthetic construct
SEQUENCE: 16
QSALTQPPSV SEAPGQRVTI SCSGSTSNIG NNAVIWYQQL PGKAPKLLIY YDDLLPSGVS  60
DRFSGSKSGT SGSLAISGLQ SEDEADYYCA SWDDNLNGPL FGGGTKLTVL RQP         113

SEQ ID NO: 17             moltype = AA  length = 13
FEATURE                   Location/Qualifiers
REGION                    1..13
                          note = Human antibody library
source                    1..13
                          mol_type = protein
                          organism = synthetic construct
SEQUENCE: 17
SGSSSNIGTY PVN                                                        13

SEQ ID NO: 18             moltype = AA  length = 7
FEATURE                   Location/Qualifiers
REGION                    1..7
                          note = Human antibody library
source                    1..7
                          mol_type = protein
                          organism = synthetic construct
SEQUENCE: 18
STDQRPS                                                               7

SEQ ID NO: 19             moltype = AA  length = 9
FEATURE                   Location/Qualifiers
REGION                    1..9
                          note = Human antibody library
source                    1..9
                          mol_type = protein
                          organism = synthetic construct
SEQUENCE: 19
QAWDSSTVV                                                             9

SEQ ID NO: 20             moltype = AA  length = 111
FEATURE                   Location/Qualifiers
REGION                    1..111
                          note = Human antibody library
source                    1..111
                          mol_type = protein
                          organism = synthetic construct
SEQUENCE: 20
QSALTQPPSA SGTPGQRVTI SCSGSSSNIG TYPVNWYQQL PGAAPKLLIY STDQRPSGVP  60
DRFSGSNSGN TATLTISGTQ AMDEADYYCQ AWDSSTVVFG GGTKLTVLGQ P           111

SEQ ID NO: 21             moltype = AA  length = 11
FEATURE                   Location/Qualifiers
REGION                    1..11
                          note = Human antibody library
source                    1..11
                          mol_type = protein
                          organism = synthetic construct
SEQUENCE: 21
SGDKLGDEYA S                                                         11

SEQ ID NO: 22             moltype = AA  length = 7
FEATURE                   Location/Qualifiers
REGION                    1..7
                          note = Human antibody library
source                    1..7
                          mol_type = protein
                          organism = synthetic construct
SEQUENCE: 22
QDNKRPS                                                               7
```

-continued

```
SEQ ID NO: 23              moltype = AA   length = 9
FEATURE                    Location/Qualifiers
REGION                     1..9
                           note = Human antibody library
source                     1..9
                           mol_type = protein
                           organism = synthetic construct
SEQUENCE: 23
QAWDSSTVV                                                          9

SEQ ID NO: 24              moltype = AA   length = 109
FEATURE                    Location/Qualifiers
REGION                     1..109
                           note = Human antibody library
source                     1..109
                           mol_type = protein
                           organism = synthetic construct
SEQUENCE: 24
QSALTQPPSV SVSPGQTASI TCSGDKLGDE YASWYQQKPG QSPVLVIYQD NKRPSGIPER  60
FSGSNSGNTA TLTISGTQAM DEADYYCQAW DSSTVVFGGG TKLTVLGQP              109

SEQ ID NO: 25              moltype = AA   length = 11
FEATURE                    Location/Qualifiers
REGION                     1..11
                           note = Human antibody library
source                     1..11
                           mol_type = protein
                           organism = synthetic construct
SEQUENCE: 25
SGDNLRHEYS S                                                       11

SEQ ID NO: 26              moltype = AA   length = 7
FEATURE                    Location/Qualifiers
REGION                     1..7
                           note = Human antibody library
source                     1..7
                           mol_type = protein
                           organism = synthetic construct
SEQUENCE: 26
QDSKRPS                                                            7

SEQ ID NO: 27              moltype = AA   length = 9
FEATURE                    Location/Qualifiers
REGION                     1..9
                           note = Human antibody library
source                     1..9
                           mol_type = protein
                           organism = synthetic construct
SEQUENCE: 27
QAWGSSTVV                                                          9

SEQ ID NO: 28              moltype = AA   length = 109
FEATURE                    Location/Qualifiers
REGION                     1..109
                           note = Human antibody library
source                     1..109
                           mol_type = protein
                           organism = synthetic construct
SEQUENCE: 28
QYELTQPPSV SVSPGQTASI TCSGDNLRHE YSSWYQQRPG QSPVLVIYQD SKRPSGIPER  60
FSGSNSGNTA TLTISGTQAL DEADYYCQAW GSSTVVFGGG TKLTVLRQP              109

SEQ ID NO: 29              moltype = AA   length = 11
FEATURE                    Location/Qualifiers
REGION                     1..11
                           note = Human antibody library
source                     1..11
                           mol_type = protein
                           organism = synthetic construct
SEQUENCE: 29
SGEKLGDEYA S                                                       11

SEQ ID NO: 30              moltype = AA   length = 7
FEATURE                    Location/Qualifiers
REGION                     1..7
                           note = Human antibody library
source                     1..7
                           mol_type = protein
```

```
                        organism = synthetic construct
SEQUENCE: 30
QDNKRPS                                                                 7

SEQ ID NO: 31          moltype = AA   length = 9
FEATURE                Location/Qualifiers
REGION                 1..9
                       note = Human antibody library
source                 1..9
                       mol_type = protein
                       organism = synthetic construct
SEQUENCE: 31
QAWDSSTLL                                                               9

SEQ ID NO: 32          moltype = AA   length = 109
FEATURE                Location/Qualifiers
REGION                 1..109
                       note = Human antibody library
source                 1..109
                       mol_type = protein
                       organism = synthetic construct
SEQUENCE: 32
QSVLTQPPSV SVSPGQTASI TCSGEKLGDE YASWYQQKPG QSPVLVIYQD NKRPSGIPER   60
FSGSNSGNTA TLTISGTQAM DEADYYCQAW DSSTLLFGGG TKLTVLGQP             109

SEQ ID NO: 33          moltype = AA   length = 11
FEATURE                Location/Qualifiers
REGION                 1..11
                       note = from human Fab library
source                 1..11
                       mol_type = protein
                       organism = synthetic construct
SEQUENCE: 33
SGEKLGDEYA S                                                           11

SEQ ID NO: 34          moltype = AA   length = 7
FEATURE                Location/Qualifiers
REGION                 1..7
                       note = from human Fab library
source                 1..7
                       mol_type = protein
                       organism = synthetic construct
SEQUENCE: 34
QDNKRPS                                                                 7

SEQ ID NO: 35          moltype = AA   length = 9
FEATURE                Location/Qualifiers
REGION                 1..9
                       note = from human Fab library
source                 1..9
                       mol_type = protein
                       organism = synthetic construct
SEQUENCE: 35
QAWDSSTLL                                                               9

SEQ ID NO: 36          moltype = AA   length = 109
FEATURE                Location/Qualifiers
REGION                 1..109
                       note = from human Fab library
source                 1..109
                       mol_type = protein
                       organism = synthetic construct
SEQUENCE: 36
QSELTQPPSV SVSPGQTASI TCSGEKLGDE YASWYQQKPG QSPVLVIYQD NKRPSGIPER   60
FSGSNSGNTA TLTISGTQAM DEADYYCQAW DSSTLLFGGG TKLTVLGQP             109

SEQ ID NO: 37          moltype = AA   length = 11
FEATURE                Location/Qualifiers
REGION                 1..11
                       note = Human antibody library
source                 1..11
                       mol_type = protein
                       organism = synthetic construct
SEQUENCE: 37
TGDKLGDQFA S                                                           11

SEQ ID NO: 38          moltype = AA   length = 7
FEATURE                Location/Qualifiers
REGION                 1..7
```

-continued

```
                          note = Human antibody library
source                    1..7
                          mol_type = protein
                          organism = synthetic construct
SEQUENCE: 38
QNDKRPS                                                      7

SEQ ID NO: 39             moltype = AA  length = 9
FEATURE                   Location/Qualifiers
REGION                    1..9
                          note = Human antibody library
source                    1..9
                          mol_type = protein
                          organism = synthetic construct
SEQUENCE: 39
QAWDFSSAL                                                    9

SEQ ID NO: 40             moltype = AA  length = 109
FEATURE                   Location/Qualifiers
REGION                    1..109
                          note = Human antibody library
source                    1..109
                          mol_type = protein
                          organism = synthetic construct
SEQUENCE: 40
QYELTQPPSV SVSPGQTATI TCTGDKLGDQ FASWYQHKPG QSPILLIYQN DKRPSGIPDR  60
FSGSDSGNTA TLTISGTQAM DEAHYYCQAW DFSSALFGGG TKLTVLGQP              109

SEQ ID NO: 41             moltype = AA  length = 11
FEATURE                   Location/Qualifiers
REGION                    1..11
                          note = Human antibody library
source                    1..11
                          mol_type = protein
                          organism = synthetic construct
SEQUENCE: 41
SGQILGERSA S                                                 11

SEQ ID NO: 42             moltype = AA  length = 7
FEATURE                   Location/Qualifiers
REGION                    1..7
                          note = Human antibody library
source                    1..7
                          mol_type = protein
                          organism = synthetic construct
SEQUENCE: 42
QSSQRPS                                                      7

SEQ ID NO: 43             moltype = AA  length = 8
FEATURE                   Location/Qualifiers
REGION                    1..8
                          note = Human antibody library
source                    1..8
                          mol_type = protein
                          organism = synthetic construct
SEQUENCE: 43
QTWDTSIL                                                     8

SEQ ID NO: 44             moltype = AA  length = 108
FEATURE                   Location/Qualifiers
REGION                    1..108
                          note = Human antibody library
source                    1..108
                          mol_type = protein
                          organism = synthetic construct
SEQUENCE: 44
QSALTQPPSV SVSPGHTATI TCSGQILGER SASWYQQRPG QAPVLVLYQS SQRPSGIPER  60
FSGSISGNTA TLTISGAQSI DEADYYCQTW DTSILFGGGT KLTVLSQP              108

SEQ ID NO: 45             moltype = AA  length = 11
FEATURE                   Location/Qualifiers
REGION                    1..11
                          note = Human antibody library
source                    1..11
                          mol_type = protein
                          organism = synthetic construct
SEQUENCE: 45
SGDALGNNYA S                                                 11
```

-continued

```
SEQ ID NO: 46          moltype = AA  length = 7
FEATURE                Location/Qualifiers
REGION                 1..7
                       note = Human antibody library
source                 1..7
                       mol_type = protein
                       organism = synthetic construct
SEQUENCE: 46
QDTKRPS                                                             7

SEQ ID NO: 47          moltype = AA  length = 10
FEATURE                Location/Qualifiers
REGION                 1..10
                       note = Human antibody library
source                 1..10
                       mol_type = protein
                       organism = synthetic construct
SEQUENCE: 47
QTWDRNTPYV                                                          10

SEQ ID NO: 48          moltype = AA  length = 110
FEATURE                Location/Qualifiers
REGION                 1..110
                       note = Human antibody library
source                 1..110
                       mol_type = protein
                       organism = synthetic construct
SEQUENCE: 48
QSALTQPPSV SVSPGQTAII TCSGDALGNN YASWYQQKPG QSPVLVIYQD TKRPSGIPER   60
FSGSSSGNTA TLTISETQTM DEADYYCQTW DRNTPYVFGA GTKVTVLGQP              110

SEQ ID NO: 49          moltype = AA  length = 13
FEATURE                Location/Qualifiers
REGION                 1..13
                       note = Human antibody library
source                 1..13
                       mol_type = protein
                       organism = synthetic construct
SEQUENCE: 49
SGSSSNIGTN TLN                                                      13

SEQ ID NO: 50          moltype = AA  length = 7
FEATURE                Location/Qualifiers
REGION                 1..7
                       note = Human antibody library
source                 1..7
                       mol_type = protein
                       organism = synthetic construct
SEQUENCE: 50
ANNQRPS                                                             7

SEQ ID NO: 51          moltype = AA  length = 11
FEATURE                Location/Qualifiers
REGION                 1..11
                       note = Human antibody library
source                 1..11
                       mol_type = protein
                       organism = synthetic construct
SEQUENCE: 51
ATWDDSLIGP V                                                        11

SEQ ID NO: 52          moltype = AA  length = 113
FEATURE                Location/Qualifiers
REGION                 1..113
                       note = Human antibody library
source                 1..113
                       mol_type = protein
                       organism = synthetic construct
SEQUENCE: 52
QSALTQPPSV SGTPGQRVTI SCSGSSSNIG TNTLNWYQQL PGTAPKLLIY ANNQRPSGVP   60
DRFSGSRSGT SASLAISGLQ SDDEADYYCA TWDDSLIGPV FGGGTKLTVL GQP          113

SEQ ID NO: 53          moltype = AA  length = 13
FEATURE                Location/Qualifiers
REGION                 1..13
                       note = from human Fab library
source                 1..13
                       mol_type = protein
                       organism = synthetic construct
```

```
SEQUENCE: 53
SGSTSNIGNN AVI                                                          13

SEQ ID NO: 54            moltype = AA   length = 7
FEATURE                  Location/Qualifiers
REGION                   1..7
                         note = from human Fab library
source                   1..7
                         mol_type = protein
                         organism = synthetic construct
SEQUENCE: 54
YDDLLPS                                                                 7

SEQ ID NO: 55            moltype = AA   length = 11
FEATURE                  Location/Qualifiers
REGION                   1..11
                         note = from human Fab library
source                   1..11
                         mol_type = protein
                         organism = synthetic construct
SEQUENCE: 55
ASWDDNLNGP L                                                            11

SEQ ID NO: 56            moltype = AA   length = 113
FEATURE                  Location/Qualifiers
REGION                   1..113
                         note = from human Fab library
source                   1..113
                         mol_type = protein
                         organism = synthetic construct
SEQUENCE: 56
QYELTQPPSV SEAPGQRVTI SCSGSTSNIG NNAVIWYQQL PGKAPKLLIY YDDLLPSGVS   60
DRFSGSKSGT SGSLAISGLQ SEDEADYYCA SWDDNLNGPL FGGGTKLTVL RQP         113

SEQ ID NO: 57            moltype = AA   length = 13
FEATURE                  Location/Qualifiers
REGION                   1..13
                         note = Human antibody library
source                   1..13
                         mol_type = protein
                         organism = synthetic construct
SEQUENCE: 57
SGSSSNLGSN TVN                                                          13

SEQ ID NO: 58            moltype = AA   length = 7
FEATURE                  Location/Qualifiers
REGION                   1..7
                         note = Human antibody library
source                   1..7
                         mol_type = protein
                         organism = synthetic construct
SEQUENCE: 58
TNSQRPS                                                                 7

SEQ ID NO: 59            moltype = AA   length = 11
FEATURE                  Location/Qualifiers
REGION                   1..11
                         note = Human antibody library
source                   1..11
                         mol_type = protein
                         organism = synthetic construct
SEQUENCE: 59
AAWDDSLNGW V                                                            11

SEQ ID NO: 60            moltype = AA   length = 113
FEATURE                  Location/Qualifiers
REGION                   1..113
                         note = Human antibody library
source                   1..113
                         mol_type = protein
                         organism = synthetic construct
SEQUENCE: 60
QSELTQPPSA SGTPGQRVTI SCSGSSSNLG SNTVNWYQQL PGTAPKLLIY TNSQRPSGVP   60
DRFSGLQSGT SASLAISGLQ SEDEADYYCA AWDDSLNGWV FGGGTKLTVL SQP         113

SEQ ID NO: 61            moltype = AA   length = 13
FEATURE                  Location/Qualifiers
REGION                   1..13
                         note = Human antibody library
```

-continued

```
source                  1..13
                        mol_type = protein
                        organism = synthetic construct
SEQUENCE: 61
SGSSSNIESN YVY                                              13

SEQ ID NO: 62           moltype = AA  length = 7
FEATURE                 Location/Qualifiers
REGION                  1..7
                        note = Human antibody library
source                  1..7
                        mol_type = protein
                        organism = synthetic construct
SEQUENCE: 62
TNNQRPS                                                      7

SEQ ID NO: 63           moltype = AA  length = 11
FEATURE                 Location/Qualifiers
REGION                  1..11
                        note = Human antibody library
source                  1..11
                        mol_type = protein
                        organism = synthetic construct
SEQUENCE: 63
ASWDDSLSGV V                                                11

SEQ ID NO: 64           moltype = AA  length = 113
FEATURE                 Location/Qualifiers
REGION                  1..113
                        note = Human antibody library
source                  1..113
                        mol_type = protein
                        organism = synthetic construct
SEQUENCE: 64
QSVLTQPPSA SGTPGQRVTI SCSGSSSNIE SNYVYWYQQL PGTAPKLLIY TNNQRPSGVP  60
DRFSGSKSGT SASLAISGLR SEDEADYYCA SWDDSLSGVV FGGGTKLTVL RQP         113

SEQ ID NO: 65           moltype = AA  length = 14
FEATURE                 Location/Qualifiers
REGION                  1..14
                        note = Human antibody library
source                  1..14
                        mol_type = protein
                        organism = synthetic construct
SEQUENCE: 65
TGSSNDIGSY DYVS                                             14

SEQ ID NO: 66           moltype = AA  length = 7
FEATURE                 Location/Qualifiers
REGION                  1..7
                        note = Human antibody library
source                  1..7
                        mol_type = protein
                        organism = synthetic construct
SEQUENCE: 66
DVNNRPS                                                      7

SEQ ID NO: 67           moltype = AA  length = 9
FEATURE                 Location/Qualifiers
REGION                  1..9
                        note = Human antibody library
source                  1..9
                        mol_type = protein
                        organism = synthetic construct
SEQUENCE: 67
MSYTITALL                                                   9

SEQ ID NO: 68           moltype = AA  length = 112
FEATURE                 Location/Qualifiers
REGION                  1..112
                        note = Human antibody library
source                  1..112
                        mol_type = protein
                        organism = synthetic construct
SEQUENCE: 68
QSELTQPDSV SGSPGQSITI SCTGSSNDIG SYDYVSWYQQ HPGRAPKFIL YDVNNRPSGV  60
ADRFSGFKSG NTASLTISGL QPDDEADYFC MSYTITALLF GGGTRVTVLG QP          112

SEQ ID NO: 69           moltype = AA  length = 14
```

-continued

```
FEATURE                Location/Qualifiers
REGION                 1..14
                       note = Human antibody library
source                 1..14
                       mol_type = protein
                       organism = synthetic construct
SEQUENCE: 69
TGSSHDIGSY DYVS                                                      14

SEQ ID NO: 70          moltype = AA   length = 7
FEATURE                Location/Qualifiers
REGION                 1..7
                       note = Human antibody library
source                 1..7
                       mol_type = protein
                       organism = synthetic construct
SEQUENCE: 70
DVNNRPS                                                              7

SEQ ID NO: 71          moltype = AA   length = 9
FEATURE                Location/Qualifiers
REGION                 1..9
                       note = Human antibody library
source                 1..9
                       mol_type = protein
                       organism = synthetic construct
SEQUENCE: 71
MSYTITTLL                                                            9

SEQ ID NO: 72          moltype = AA   length = 112
FEATURE                Location/Qualifiers
REGION                 1..112
                       note = Human antibody library
source                 1..112
                       mol_type = protein
                       organism = synthetic construct
SEQUENCE: 72
QSALTQPDSV SGSPGQSITI SCTGSSHDIG SYDYVSWYQY HPGKAPKFIL YDVNNRPSGV    60
SDRFSGSKSG NTASLTISGL QPDDEADYFC MSYTITTLLF GTGTRVTVLS QP            112

SEQ ID NO: 73          moltype = AA   length = 14
FEATURE                Location/Qualifiers
REGION                 1..14
                       note = Human antibody library
source                 1..14
                       mol_type = protein
                       organism = synthetic construct
SEQUENCE: 73
AGTSSDVGAY DYVS                                                      14

SEQ ID NO: 74          moltype = AA   length = 7
FEATURE                Location/Qualifiers
REGION                 1..7
                       note = Human antibody library
source                 1..7
                       mol_type = protein
                       organism = synthetic construct
SEQUENCE: 74
DVYNRPS                                                              7

SEQ ID NO: 75          moltype = AA   length = 9
FEATURE                Location/Qualifiers
REGION                 1..9
                       note = Human antibody library
source                 1..9
                       mol_type = protein
                       organism = synthetic construct
SEQUENCE: 75
MSYTITTLL                                                            9

SEQ ID NO: 76          moltype = AA   length = 112
FEATURE                Location/Qualifiers
REGION                 1..112
                       note = Human antibody library
source                 1..112
                       mol_type = protein
                       organism = synthetic construct
SEQUENCE: 76
QSALTQPASM SGSRGQSITI SCAGTSSDVG AYDYVSWYKH LPGNAPKFIL YDVYNRPSGV    60
```

```
SDRFSGSKSG NTASLTISGL QPDDEADYFC MSYTITTLLF GTGTRVTVLS QP          112

SEQ ID NO: 77          moltype = AA  length = 14
FEATURE                Location/Qualifiers
REGION                 1..14
                       note = Human antibody library
source                 1..14
                       mol_type = protein
                       organism = synthetic construct
SEQUENCE: 77
TGSSHDIGAY DYVS                                                     14

SEQ ID NO: 78          moltype = AA  length = 7
FEATURE                Location/Qualifiers
REGION                 1..7
                       note = Human antibody library
source                 1..7
                       mol_type = protein
                       organism = synthetic construct
SEQUENCE: 78
DVYNRPS                                                             7

SEQ ID NO: 79          moltype = AA  length = 9
FEATURE                Location/Qualifiers
REGION                 1..9
                       note = Human antibody library
source                 1..9
                       mol_type = protein
                       organism = synthetic construct
SEQUENCE: 79
MSYTITTLL                                                          9

SEQ ID NO: 80          moltype = AA  length = 112
FEATURE                Location/Qualifiers
REGION                 1..112
                       note = Human antibody library
source                 1..112
                       mol_type = protein
                       organism = synthetic construct
SEQUENCE: 80
QSVLTQPDSV SGSPGQSITI SCTGSSHDIG AYDYVSWYKH LPGNAPKFIL YDVYNRPSGV  60
SDRFSGSKSG NTASLTISGL QPDDEADYFC MSYTITTLLF GTGTRVTVLS QP          112

SEQ ID NO: 81          moltype = AA  length = 14
FEATURE                Location/Qualifiers
REGION                 1..14
                       note = from human Fab library
source                 1..14
                       mol_type = protein
                       organism = synthetic construct
SEQUENCE: 81
TGSSHDIGAY DYVS                                                     14

SEQ ID NO: 82          moltype = AA  length = 7
FEATURE                Location/Qualifiers
REGION                 1..7
                       note = from human Fab library
source                 1..7
                       mol_type = protein
                       organism = synthetic construct
SEQUENCE: 82
DVYNRPS                                                             7

SEQ ID NO: 83          moltype = AA  length = 9
FEATURE                Location/Qualifiers
REGION                 1..9
                       note = from human Fab library
source                 1..9
                       mol_type = protein
                       organism = synthetic construct
SEQUENCE: 83
MSYTITTLL                                                          9

SEQ ID NO: 84          moltype = AA  length = 112
FEATURE                Location/Qualifiers
REGION                 1..112
                       note = from human Fab library
source                 1..112
                       mol_type = protein
```

-continued

```
                    organism = synthetic construct
SEQUENCE: 84
QSVLTQPASV SGSPGQSITI SCTGSSHDIG AYDYVSWYKH LPGNAPKFIL YDVYNRPSGV   60
SDRFSGSKSG NTASLTISGL QPDDEADYFC MSYTITTLLF GTGTRVTVLS QP           112

SEQ ID NO: 85          moltype = AA   length = 14
FEATURE                Location/Qualifiers
REGION                 1..14
                       note = from human Fab library
source                 1..14
                       mol_type = protein
                       organism = synthetic construct
SEQUENCE: 85
TGSSHDIGAY DYVS                                                      14

SEQ ID NO: 86          moltype = AA   length = 7
FEATURE                Location/Qualifiers
REGION                 1..7
                       note = from human Fab library
source                 1..7
                       mol_type = protein
                       organism = synthetic construct
SEQUENCE: 86
DVYNRPS                                                              7

SEQ ID NO: 87          moltype = AA   length = 9
FEATURE                Location/Qualifiers
REGION                 1..9
                       note = from human Fab library
source                 1..9
                       mol_type = protein
                       organism = synthetic construct
SEQUENCE: 87
MSYTITTLL                                                            9

SEQ ID NO: 88          moltype = AA   length = 112
FEATURE                Location/Qualifiers
REGION                 1..112
                       note = from human Fab library
source                 1..112
                       mol_type = protein
                       organism = synthetic construct
SEQUENCE: 88
QSVLTQPYSV SGSPGQSITI SCTGSSHDIG AYDYVSWYKH LPGNAPKFIL YDVYNRPSGV   60
SDRFSGSKSG NTASLTISGL QPDDEADYFC MSYTITTLLF GTGTRVTVLS QP           112

SEQ ID NO: 89          moltype = AA   length = 14
FEATURE                Location/Qualifiers
REGION                 1..14
                       note = Human antibody library
source                 1..14
                       mol_type = protein
                       organism = synthetic construct
SEQUENCE: 89
TGSSHDIGAY DYVS                                                      14

SEQ ID NO: 90          moltype = AA   length = 7
FEATURE                Location/Qualifiers
REGION                 1..7
                       note = Human antibody library
source                 1..7
                       mol_type = protein
                       organism = synthetic construct
SEQUENCE: 90
DVYNRPS                                                              7

SEQ ID NO: 91          moltype = AA   length = 9
FEATURE                Location/Qualifiers
REGION                 1..9
                       note = Human antibody library
source                 1..9
                       mol_type = protein
                       organism = synthetic construct
SEQUENCE: 91
MSYTITTLL                                                            9

SEQ ID NO: 92          moltype = AA   length = 112
FEATURE                Location/Qualifiers
REGION                 1..112
```

```
                        note = Human antibody library
source                  1..112
                        mol_type = protein
                        organism = synthetic construct
SEQUENCE: 92
QSALTQPDSV SGSPGQSITI SCTGSSHDIG AYDYVSWYKH LPGNAPKFIL YDVYNRPSGV  60
SDRFSGSKSG NTASLTISGL QPDDEADYFC MSYTITTLLF GTGTRVTVLS QP          112

SEQ ID NO: 93           moltype = AA  length = 14
FEATURE                 Location/Qualifiers
REGION                  1..14
                        note = from human Fab library
source                  1..14
                        mol_type = protein
                        organism = synthetic construct
SEQUENCE: 93
TGSSHDIGAY DYVS                                                    14

SEQ ID NO: 94           moltype = AA  length = 7
FEATURE                 Location/Qualifiers
REGION                  1..7
                        note = from human Fab library
source                  1..7
                        mol_type = protein
                        organism = synthetic construct
SEQUENCE: 94
DVYNRPS                                                            7

SEQ ID NO: 95           moltype = AA  length = 9
FEATURE                 Location/Qualifiers
REGION                  1..9
                        note = from human Fab library
source                  1..9
                        mol_type = protein
                        organism = synthetic construct
SEQUENCE: 95
MSYTITTLL                                                          9

SEQ ID NO: 96           moltype = AA  length = 112
FEATURE                 Location/Qualifiers
REGION                  1..112
                        note = from human Fab library
source                  1..112
                        mol_type = protein
                        organism = synthetic construct
SEQUENCE: 96
QSELTQPDSV SGSPGQSITI SCTGSSHDIG AYDYVSWYKH LPGNAPKFIL YDVYNRPSGV  60
SDRFSGSKSG NTASLTISGL QPDDEADYFC MSYTITTLLF GTGTRVTVLS QP          112

SEQ ID NO: 97           moltype = AA  length = 12
FEATURE                 Location/Qualifiers
REGION                  1..12
                        note = Human antibody library
source                  1..12
                        mol_type = protein
                        organism = synthetic construct
SEQUENCE: 97
RASQSVSSSY LA                                                      12

SEQ ID NO: 98           moltype = AA  length = 7
FEATURE                 Location/Qualifiers
REGION                  1..7
                        note = Human antibody library
source                  1..7
                        mol_type = protein
                        organism = synthetic construct
SEQUENCE: 98
GASSRAT                                                            7

SEQ ID NO: 99           moltype = AA  length = 9
FEATURE                 Location/Qualifiers
REGION                  1..9
                        note = Human antibody library
source                  1..9
                        mol_type = protein
                        organism = synthetic construct
SEQUENCE: 99
QQFDSSPPT                                                          9
```

-continued

```
SEQ ID NO: 100        moltype = AA   length = 109
FEATURE               Location/Qualifiers
REGION                1..109
                      note = Human antibody library
source                1..109
                      mol_type = protein
                      organism = synthetic construct
SEQUENCE: 100
DIQMTQSPGT LSLSPGERAT LSCRASQSVS SSYLAWYQQK PGQAPRLLMY GASSRATGFP   60
DRFSGSGSGT DFSLTISRLE PEDFAVYYCQ QFDSSPPTFG GGTKVEIKR              109

SEQ ID NO: 101        moltype = AA   length = 12
FEATURE               Location/Qualifiers
REGION                1..12
                      note = Human antibody library
source                1..12
                      mol_type = protein
                      organism = synthetic construct
SEQUENCE: 101
RASERISSNY LM                                                       12

SEQ ID NO: 102        moltype = AA   length = 7
FEATURE               Location/Qualifiers
REGION                1..7
                      note = Human antibody library
source                1..7
                      mol_type = protein
                      organism = synthetic construct
SEQUENCE: 102
GASIRAT                                                              7

SEQ ID NO: 103        moltype = AA   length = 9
FEATURE               Location/Qualifiers
REGION                1..9
                      note = Human antibody library
source                1..9
                      mol_type = protein
                      organism = synthetic construct
SEQUENCE: 103
QQYSSPLT                                                             9

SEQ ID NO: 104        moltype = AA   length = 109
FEATURE               Location/Qualifiers
REGION                1..109
                      note = Human antibody library
source                1..109
                      mol_type = protein
                      organism = synthetic construct
SEQUENCE: 104
DIQMTQSPGT LSVLPGERAT LSCRASERIS SNYLMWYQQK PGQAPRLLMY GASIRATGIP   60
DRFSGSESGT DFTLTISRVE PEDFAVYYCQ QYSSPLTFG GGTKVEMKR               109

SEQ ID NO: 105        moltype = AA   length = 12
FEATURE               Location/Qualifiers
REGION                1..12
                      note = Human antibody library
source                1..12
                      mol_type = protein
                      organism = synthetic construct
SEQUENCE: 105
RASQSISSNY LA                                                       12

SEQ ID NO: 106        moltype = AA   length = 7
FEATURE               Location/Qualifiers
REGION                1..7
                      note = Human antibody library
source                1..7
                      mol_type = protein
                      organism = synthetic construct
SEQUENCE: 106
GASSRST                                                              7

SEQ ID NO: 107        moltype = AA   length = 9
FEATURE               Location/Qualifiers
REGION                1..9
                      note = Human antibody library
source                1..9
                      mol_type = protein
                      organism = synthetic construct
```

-continued

```
SEQUENCE: 107
QQFDTLPIT                                                            9

SEQ ID NO: 108         moltype = AA   length = 109
FEATURE                Location/Qualifiers
REGION                 1..109
                       note = Human antibody library
source                 1..109
                       mol_type = protein
                       organism = synthetic construct
SEQUENCE: 108
DIQMTQSPGT LSLSPGERAT LSCRASQSIS SNYLAWYQQR PGQAPRLLIY GASSRSTGTP    60
DRFSGSGSGT DFTLTISRLE PEDFAIYYCQ QFDTLPITFG QGTRLDIKR               109

SEQ ID NO: 109         moltype = AA   length = 13
FEATURE                Location/Qualifiers
REGION                 1..13
                       note = Human antibody library
source                 1..13
                       mol_type = protein
                       organism = synthetic construct
SEQUENCE: 109
RASQSIRSSG YLS                                                       13

SEQ ID NO: 110         moltype = AA   length = 7
FEATURE                Location/Qualifiers
REGION                 1..7
                       note = Human antibody library
source                 1..7
                       mol_type = protein
                       organism = synthetic construct
SEQUENCE: 110
GASTRAT                                                              7

SEQ ID NO: 111         moltype = AA   length = 9
FEATURE                Location/Qualifiers
REGION                 1..9
                       note = Human antibody library
source                 1..9
                       mol_type = protein
                       organism = synthetic construct
SEQUENCE: 111
QQYGSSTIT                                                            9

SEQ ID NO: 112         moltype = AA   length = 110
FEATURE                Location/Qualifiers
REGION                 1..110
                       note = Human antibody library
source                 1..110
                       mol_type = protein
                       organism = synthetic construct
SEQUENCE: 112
DIQMTQSPAT LSLSPGERAT LSCRASQSIR SSGYLSWFQQ KPGQAPRLLI YGASTRATGT    60
PARFSGSGSG TDFTLTIDRL ESEDFAVYFC QQYGSSTITF GQGTRLEIKR              110

SEQ ID NO: 113         moltype = AA   length = 12
FEATURE                Location/Qualifiers
REGION                 1..12
                       note = Human antibody library
source                 1..12
                       mol_type = protein
                       organism = synthetic construct
SEQUENCE: 113
RASQSVSSNY LG                                                        12

SEQ ID NO: 114         moltype = AA   length = 7
FEATURE                Location/Qualifiers
REGION                 1..7
                       note = Human antibody library
source                 1..7
                       mol_type = protein
                       organism = synthetic construct
SEQUENCE: 114
GASSRAT                                                              7

SEQ ID NO: 115         moltype = AA   length = 9
FEATURE                Location/Qualifiers
REGION                 1..9
                       note = Human antibody library
```

```
source                   1..9
                         mol_type = protein
                         organism = synthetic construct
SEQUENCE: 115
QQFDNLPVT                                                        9

SEQ ID NO: 116           moltype = AA  length = 109
FEATURE                  Location/Qualifiers
REGION                   1..109
                         note = Human antibody library
source                   1..109
                         mol_type = protein
                         organism = synthetic construct
SEQUENCE: 116
DIQMTQSPGT LSLSPGERAT LSCRASQSVS SNYLGWYQQK PGQAPRLLIY GASSRATGIP  60
DRFSGSGSGT DFTLTISRLE PEDFAVYYCQ QFDNLPVTFG GGTKVEMKR             109

SEQ ID NO: 117           moltype = AA  length = 12
FEATURE                  Location/Qualifiers
REGION                   1..12
                         note = Human antibody library
source                   1..12
                         mol_type = protein
                         organism = synthetic construct
SEQUENCE: 117
RASQSVSSNY LA                                                     12

SEQ ID NO: 118           moltype = AA  length = 7
FEATURE                  Location/Qualifiers
REGION                   1..7
                         note = Human antibody library
source                   1..7
                         mol_type = protein
                         organism = synthetic construct
SEQUENCE: 118
GASSRAT                                                           7

SEQ ID NO: 119           moltype = AA  length = 9
FEATURE                  Location/Qualifiers
REGION                   1..9
                         note = Human antibody library
source                   1..9
                         mol_type = protein
                         organism = synthetic construct
SEQUENCE: 119
QQFDTSPLT                                                         9

SEQ ID NO: 120           moltype = AA  length = 109
FEATURE                  Location/Qualifiers
REGION                   1..109
                         note = Human antibody library
source                   1..109
                         mol_type = protein
                         organism = synthetic construct
SEQUENCE: 120
DIQMTQSPGT LSLSPGERAT LSCRASQSVS SNYLAWYQQK PGQAPRLLIY GASSRATGIP  60
DRFSGSGSGT DFTLTISRLE PEDFAVYYCQ QFDTSPLTIG GGTRVDIKR             109

SEQ ID NO: 121           moltype = AA  length = 12
FEATURE                  Location/Qualifiers
REGION                   1..12
                         note = Human antibody library
source                   1..12
                         mol_type = protein
                         organism = synthetic construct
SEQUENCE: 121
RASQSVSSNY LA                                                     12

SEQ ID NO: 122           moltype = AA  length = 7
FEATURE                  Location/Qualifiers
REGION                   1..7
                         note = Human antibody library
source                   1..7
                         mol_type = protein
                         organism = synthetic construct
SEQUENCE: 122
GASSRAT                                                           7

SEQ ID NO: 123           moltype = AA  length = 9
```

-continued

```
FEATURE              Location/Qualifiers
REGION               1..9
                     note = Human antibody library
source               1..9
                     mol_type = protein
                     organism = synthetic construct
SEQUENCE: 123
QQFDSSPLS                                                      9

SEQ ID NO: 124       moltype = AA  length = 109
FEATURE              Location/Qualifiers
REGION               1..109
                     note = Human antibody library
source               1..109
                     mol_type = protein
                     organism = synthetic construct
SEQUENCE: 124
DIQMTQSPGT LSLSPGERAT LSCRASQSVS SNYLAWYQQK PGQAPRLLIY GASSRATGIP  60
DRFSGSGSGT DFSLTISRLE PEDSAVYYCQ QFDSSPLSFG GGTKVEIKR              109

SEQ ID NO: 125       moltype = AA  length = 12
FEATURE              Location/Qualifiers
REGION               1..12
                     note = Human antibody library
source               1..12
                     mol_type = protein
                     organism = synthetic construct
SEQUENCE: 125
RASQSVSSWY LA                                                  12

SEQ ID NO: 126       moltype = AA  length = 7
FEATURE              Location/Qualifiers
REGION               1..7
                     note = Human antibody library
source               1..7
                     mol_type = protein
                     organism = synthetic construct
SEQUENCE: 126
GASNRAT                                                        7

SEQ ID NO: 127       moltype = AA  length = 9
FEATURE              Location/Qualifiers
REGION               1..9
                     note = Human antibody library
source               1..9
                     mol_type = protein
                     organism = synthetic construct
SEQUENCE: 127
QQFDSSPLT                                                      9

SEQ ID NO: 128       moltype = AA  length = 109
FEATURE              Location/Qualifiers
REGION               1..109
                     note = Human antibody library
source               1..109
                     mol_type = protein
                     organism = synthetic construct
SEQUENCE: 128
DIQMTQSPGT LSLSPGERAT LSCRASQSVS SWYLAWYQQK PGQAPRLLMY GASNRATGIP  60
DRFSGSGSGT DFTLTISRLE PEDSAVYYCQ QFDSSPLTIG GGTKVEIKR              109

SEQ ID NO: 129       moltype = AA  length = 12
FEATURE              Location/Qualifiers
REGION               1..12
                     note = Human antibody library
source               1..12
                     mol_type = protein
                     organism = synthetic construct
SEQUENCE: 129
RASQNVGSSY LA                                                  12

SEQ ID NO: 130       moltype = AA  length = 7
FEATURE              Location/Qualifiers
REGION               1..7
                     note = Human antibody library
source               1..7
                     mol_type = protein
                     organism = synthetic construct
SEQUENCE: 130
```

```
GASSRAT                                                           7

SEQ ID NO: 131          moltype = AA  length = 9
FEATURE                 Location/Qualifiers
REGION                  1..9
                        note = Human antibody library
source                  1..9
                        mol_type = protein
                        organism = synthetic construct
SEQUENCE: 131
QQFDSSPPT                                                         9

SEQ ID NO: 132          moltype = AA  length = 109
FEATURE                 Location/Qualifiers
REGION                  1..109
                        note = Human antibody library
source                  1..109
                        mol_type = protein
                        organism = synthetic construct
SEQUENCE: 132
DIQMTQSPGT LSLSPGERAT LSCRASQNVG SSYLAWYQQK PGQAPRLLMY GASSRATGFP  60
DRFSGSGSGT DFSLTISRLE PEDFAVYYCQ QFDSSPPTFG GGTKVEIKR             109

SEQ ID NO: 133          moltype = AA  length = 12
FEATURE                 Location/Qualifiers
REGION                  1..12
                        note = Human antibody library
source                  1..12
                        mol_type = protein
                        organism = synthetic construct
SEQUENCE: 133
RASQSVSSSY LA                                                     12

SEQ ID NO: 134          moltype = AA  length = 7
FEATURE                 Location/Qualifiers
REGION                  1..7
                        note = Human antibody library
source                  1..7
                        mol_type = protein
                        organism = synthetic construct
SEQUENCE: 134
GASSRAT                                                           7

SEQ ID NO: 135          moltype = AA  length = 9
FEATURE                 Location/Qualifiers
REGION                  1..9
                        note = Human antibody library
source                  1..9
                        mol_type = protein
                        organism = synthetic construct
SEQUENCE: 135
QQFDSSPPT                                                         9

SEQ ID NO: 136          moltype = AA  length = 109
FEATURE                 Location/Qualifiers
REGION                  1..109
                        note = Human antibody library
source                  1..109
                        mol_type = protein
                        organism = synthetic construct
SEQUENCE: 136
DIQMTQSPGT LSLSPGERAT LSCRASQSVS SSYLAWYQQK PGQAPRLLMY GASSRATGFP  60
DRFSGSGSGT DFSLTISRLE PEDFAVYYCQ QFDSSPPTFG GGTKVEIKR             109

SEQ ID NO: 137          moltype = AA  length = 12
FEATURE                 Location/Qualifiers
REGION                  1..12
                        note = from human antibody library
source                  1..12
                        mol_type = protein
                        organism = synthetic construct
SEQUENCE: 137
RASQSVSSSY LA                                                     12

SEQ ID NO: 138          moltype = AA  length = 7
FEATURE                 Location/Qualifiers
REGION                  1..7
                        note = from human antibody library
source                  1..7
```

```
                          mol_type = protein
                          organism = synthetic construct
SEQUENCE: 138
GASSRAT                                                        7

SEQ ID NO: 139          moltype = AA  length = 9
FEATURE                 Location/Qualifiers
REGION                  1..9
                          note = from human antibody library
source                  1..9
                          mol_type = protein
                          organism = synthetic construct
SEQUENCE: 139
QQFDSSPPT                                                      9

SEQ ID NO: 140          moltype = AA  length = 109
FEATURE                 Location/Qualifiers
REGION                  1..109
                          note = from human antibody library
source                  1..109
                          mol_type = protein
                          organism = synthetic construct
SEQUENCE: 140
DIQMTQSPGT LSLSPGERAT LSCRASQSVS SSYLAWYQQK PGRAPRLLMY GASSRATGFP   60
DRFSGSGSGT DFSLTISRLE PEDFAVYYCQ QFDSSPPTFG GGTKVEIKR              109

SEQ ID NO: 141          moltype = AA  length = 12
FEATURE                 Location/Qualifiers
REGION                  1..12
                          note = Human antibody library
source                  1..12
                          mol_type = protein
                          organism = synthetic construct
SEQUENCE: 141
RASQSVSSSY LA                                                  12

SEQ ID NO: 142          moltype = AA  length = 7
FEATURE                 Location/Qualifiers
REGION                  1..7
                          note = Human antibody library
source                  1..7
                          mol_type = protein
                          organism = synthetic construct
SEQUENCE: 142
GASSRAT                                                        7

SEQ ID NO: 143          moltype = AA  length = 10
FEATURE                 Location/Qualifiers
REGION                  1..10
                          note = Human antibody library
source                  1..10
                          mol_type = protein
                          organism = synthetic construct
SEQUENCE: 143
QQFGSSPPYT                                                     10

SEQ ID NO: 144          moltype = AA  length = 110
FEATURE                 Location/Qualifiers
REGION                  1..110
                          note = Human antibody library
source                  1..110
                          mol_type = protein
                          organism = synthetic construct
SEQUENCE: 144
DIQMTQSPGT LSLSPGERAT LSCRASQSVS SSYLAWYQQK PGQAPRLLIY GASSRATGIP   60
DRFSGSGSGT DYTLTINRLE PEDFAVYYCQ QFGSSPPYTF GQGTKLEIKR             110

SEQ ID NO: 145          moltype = AA  length = 12
FEATURE                 Location/Qualifiers
REGION                  1..12
                          note = Human antibody library
source                  1..12
                          mol_type = protein
                          organism = synthetic construct
SEQUENCE: 145
RASQSVSSSY LA                                                  12

SEQ ID NO: 146          moltype = AA  length = 7
FEATURE                 Location/Qualifiers
```

-continued

```
REGION                   1..7
                         note = Human antibody library
source                   1..7
                         mol_type = protein
                         organism = synthetic construct
SEQUENCE: 146
GASTRAT                                                              7

SEQ ID NO: 147           moltype = AA  length = 10
FEATURE                  Location/Qualifiers
REGION                   1..10
                         note = Human antibody library
source                   1..10
                         mol_type = protein
                         organism = synthetic construct
SEQUENCE: 147
QQFDNWPPWT                                                           10

SEQ ID NO: 148           moltype = AA  length = 110
FEATURE                  Location/Qualifiers
REGION                   1..110
                         note = Human antibody library
source                   1..110
                         mol_type = protein
                         organism = synthetic construct
SEQUENCE: 148
DIQMTQSPGT LSLSPGERAT LSCRASQSVS SSYLAWYQQK PGQAPRLLIY GASTRATGIP   60
PRFSGSGSGT EFTLTISSVQ SEDFAIYYCQ QFDNWPPWTF GQGTKVEIKR              110

SEQ ID NO: 149           moltype = AA  length = 12
FEATURE                  Location/Qualifiers
REGION                   1..12
                         note = Human antibody library
source                   1..12
                         mol_type = protein
                         organism = synthetic construct
SEQUENCE: 149
RASQSVSSNY FG                                                       12

SEQ ID NO: 150           moltype = AA  length = 7
FEATURE                  Location/Qualifiers
REGION                   1..7
                         note = Human antibody library
source                   1..7
                         mol_type = protein
                         organism = synthetic construct
SEQUENCE: 150
GASSRAT                                                              7

SEQ ID NO: 151           moltype = AA  length = 9
FEATURE                  Location/Qualifiers
REGION                   1..9
                         note = Human antibody library
source                   1..9
                         mol_type = protein
                         organism = synthetic construct
SEQUENCE: 151
QQFDSSPLT                                                            9

SEQ ID NO: 152           moltype = AA  length = 109
FEATURE                  Location/Qualifiers
REGION                   1..109
                         note = Human antibody library
source                   1..109
                         mol_type = protein
                         organism = synthetic construct
SEQUENCE: 152
DIQMTQSPGT LSLSPGEGAT LSCRASQSVS SNYFGWYQQK PGQAPRLLIY GASSRATGIP   60
DRFSGSGSGT DFTLTISRLE PEDSAVYYCQ QFDSSPLTFG GGTKVEIKR               109

SEQ ID NO: 153           moltype = AA  length = 12
FEATURE                  Location/Qualifiers
REGION                   1..12
                         note = from human antibody library
source                   1..12
                         mol_type = protein
                         organism = synthetic construct
SEQUENCE: 153
RASQSVSSNY LA                                                       12
```

```
SEQ ID NO: 154          moltype = AA   length = 7
FEATURE                 Location/Qualifiers
REGION                  1..7
                        note = Human antibody library
source                  1..7
                        mol_type = protein
                        organism = synthetic construct
SEQUENCE: 154
GASSRAT                                                              7

SEQ ID NO: 155          moltype = AA   length = 9
FEATURE                 Location/Qualifiers
REGION                  1..9
                        note = Human antibody library
source                  1..9
                        mol_type = protein
                        organism = synthetic construct
SEQUENCE: 155
QQFDSSPLS                                                            9

SEQ ID NO: 156          moltype = AA   length = 109
FEATURE                 Location/Qualifiers
REGION                  1..109
                        note = Human antibody library
source                  1..109
                        mol_type = protein
                        organism = synthetic construct
SEQUENCE: 156
DIQMTQSPGT LSLSPGERAT LSCRASQSVS SNYLAWYQQK PGQAPRLLIY GASSRATGIP   60
DRFSGSGSGT DFSLTISRLE PEDSAVYYCQ QFDSSPLSFG GGTKVEIKR              109

SEQ ID NO: 157          moltype = AA   length = 12
FEATURE                 Location/Qualifiers
REGION                  1..12
                        note = Human antibody library
source                  1..12
                        mol_type = protein
                        organism = synthetic construct
SEQUENCE: 157
RASQSVSSNY LA                                                       12

SEQ ID NO: 158          moltype = AA   length = 7
FEATURE                 Location/Qualifiers
REGION                  1..7
                        note = Human antibody library
source                  1..7
                        mol_type = protein
                        organism = synthetic construct
SEQUENCE: 158
GASTRAT                                                              7

SEQ ID NO: 159          moltype = AA   length = 9
FEATURE                 Location/Qualifiers
REGION                  1..9
                        note = Human antibody library
source                  1..9
                        mol_type = protein
                        organism = synthetic construct
SEQUENCE: 159
QQFDSSPLS                                                            9

SEQ ID NO: 160          moltype = AA   length = 109
FEATURE                 Location/Qualifiers
REGION                  1..109
                        note = Human antibody library
source                  1..109
                        mol_type = protein
                        organism = synthetic construct
SEQUENCE: 160
DIQMTQSPGT LSLSPGDRAT LSCRASQSVS SNYLAWYQQK PGQAPRVLIY GASTRATGIP   60
DRFTGSGSGT DFTLTISRLE PEDSAVYYCQ QFDSSPLSFG GGTKVEIKR              109

SEQ ID NO: 161          moltype = AA   length = 12
FEATURE                 Location/Qualifiers
REGION                  1..12
                        note = Human antibody library
source                  1..12
                        mol_type = protein
```

-continued

```
                                         organism = synthetic construct
SEQUENCE: 161
RASQSLNNNY LA                                                        12

SEQ ID NO: 162            moltype = AA   length = 7
FEATURE                   Location/Qualifiers
REGION                    1..7
                          note = Human antibody library
source                    1..7
                          mol_type = protein
                          organism = synthetic construct
SEQUENCE: 162
GASTRAT                                                              7

SEQ ID NO: 163            moltype = AA   length = 9
FEATURE                   Location/Qualifiers
REGION                    1..9
                          note = Human antibody library
source                    1..9
                          mol_type = protein
                          organism = synthetic construct
SEQUENCE: 163
QQFDSSPPT                                                            9

SEQ ID NO: 164            moltype = AA   length = 109
FEATURE                   Location/Qualifiers
REGION                    1..109
                          note = Human antibody library
source                    1..109
                          mol_type = protein
                          organism = synthetic construct
SEQUENCE: 164
DIQMTQSPGT LSLSPGERAT LSCRASQSLN NNYLAWYQQK PGQAPRLLMY GASTRATGIP    60
ARFSGSGSGT EFTLTISSLQ SEDFAVYYCQ QFDSSPPTFG GGTKVEIKR               109

SEQ ID NO: 165            moltype = AA   length = 12
FEATURE                   Location/Qualifiers
REGION                    1..12
                          note = Human antibody library
source                    1..12
                          mol_type = protein
                          organism = synthetic construct
SEQUENCE: 165
RASHSVSSDY LA                                                        12

SEQ ID NO: 166            moltype = AA   length = 7
FEATURE                   Location/Qualifiers
REGION                    1..7
                          note = Human antibody library
source                    1..7
                          mol_type = protein
                          organism = synthetic construct
SEQUENCE: 166
GASSRAT                                                              7

SEQ ID NO: 167            moltype = AA   length = 9
FEATURE                   Location/Qualifiers
REGION                    1..9
                          note = Human antibody library
source                    1..9
                          mol_type = protein
                          organism = synthetic construct
SEQUENCE: 167
QQFDSSPPT                                                            9

SEQ ID NO: 168            moltype = AA   length = 109
FEATURE                   Location/Qualifiers
REGION                    1..109
                          note = Human antibody library
source                    1..109
                          mol_type = protein
                          organism = synthetic construct
SEQUENCE: 168
DIQMTQSPAT LSLSPGERAT LSCRASHSVS SDYLAWYQQK PGRAPRLLMY GASSRATGFP    60
DRFSGSGSGT DFSLTISRLE PEDFAMYYCQ QFDSSPPTFG GGTKVEIKR               109

SEQ ID NO: 169            moltype = AA   length = 12
FEATURE                   Location/Qualifiers
REGION                    1..12
```

```
                              note = from human antibody library
source                        1..12
                              mol_type = protein
                              organism = synthetic construct
SEQUENCE: 169
RASHSVSSDY LA                                                    12

SEQ ID NO: 170                moltype = AA  length = 7
FEATURE                       Location/Qualifiers
REGION                        1..7
                              note = from human antibody library
source                        1..7
                              mol_type = protein
                              organism = synthetic construct
SEQUENCE: 170
GASSRAT                                                          7

SEQ ID NO: 171                moltype = AA  length = 9
FEATURE                       Location/Qualifiers
REGION                        1..9
                              note = from human antibody library
source                        1..9
                              mol_type = protein
                              organism = synthetic construct
SEQUENCE: 171
QQFDSSPPT                                                        9

SEQ ID NO: 172                moltype = AA  length = 109
FEATURE                       Location/Qualifiers
REGION                        1..109
                              note = from human antibody library
source                        1..109
                              mol_type = protein
                              organism = synthetic construct
SEQUENCE: 172
DIQMTQSPAT LSVSPGERAT LSCRASHSVS SDYLAWYQQK PGRAPRLLMY GASSRATGFP  60
DRFSGSGSGT DFSLTISRLE PEDFAMYYCQ QFDSSPPTFG GGTKVEIKR             109

SEQ ID NO: 173                moltype = AA  length = 12
FEATURE                       Location/Qualifiers
REGION                        1..12
                              note = Human antibody library
source                        1..12
                              mol_type = protein
                              organism = synthetic construct
SEQUENCE: 173
RASHSVSSDY LA                                                    12

SEQ ID NO: 174                moltype = AA  length = 7
FEATURE                       Location/Qualifiers
REGION                        1..7
                              note = Human antibody library
source                        1..7
                              mol_type = protein
                              organism = synthetic construct
SEQUENCE: 174
GASSRAT                                                          7

SEQ ID NO: 175                moltype = AA  length = 9
FEATURE                       Location/Qualifiers
REGION                        1..9
                              note = Human antibody library
source                        1..9
                              mol_type = protein
                              organism = synthetic construct
SEQUENCE: 175
QQFDSSPPT                                                        9

SEQ ID NO: 176                moltype = AA  length = 109
FEATURE                       Location/Qualifiers
REGION                        1..109
                              note = Human antibody library
source                        1..109
                              mol_type = protein
                              organism = synthetic construct
SEQUENCE: 176
DIQMTQSPGT LSLSPGERAT LSCRASHSVS SDYLAWYQQK PGRAPRLLMY GASSRATGFP  60
DRFSGSGSGT DFSLTISRLE PEDFAVYYCQ QFDSSPPTFG GGTKVEIKR             109
```

-continued

```
SEQ ID NO: 177            moltype = AA   length = 12
FEATURE                   Location/Qualifiers
REGION                    1..12
                          note = Human antibody library
source                    1..12
                          mol_type = protein
                          organism = synthetic construct
SEQUENCE: 177
RASHSVSSDY LA                                                    12

SEQ ID NO: 178            moltype = AA   length = 7
FEATURE                   Location/Qualifiers
REGION                    1..7
                          note = Human antibody library
source                    1..7
                          mol_type = protein
                          organism = synthetic construct
SEQUENCE: 178
GASSRAT                                                          7

SEQ ID NO: 179            moltype = AA   length = 9
FEATURE                   Location/Qualifiers
REGION                    1..9
                          note = Human antibody library
source                    1..9
                          mol_type = protein
                          organism = synthetic construct
SEQUENCE: 179
QQFDSSPPT                                                        9

SEQ ID NO: 180            moltype = AA   length = 111
FEATURE                   Location/Qualifiers
REGION                    1..111
                          note = from human Fab library
source                    1..111
                          mol_type = protein
                          organism = synthetic construct
SEQUENCE: 180
IADIQMTQSP DTLSLSPGER ATLSCRASHS VSSDYLAWYQ QKPGRAPRLL MYGASSRATG   60
FPDRFSGSGS GTDFSLTISR LEPEDFAVYY CQQFDSSPPT FGGGTKVEIK R           111

SEQ ID NO: 181            moltype = AA   length = 12
FEATURE                   Location/Qualifiers
REGION                    1..12
                          note = from human antibody library
source                    1..12
                          mol_type = protein
                          organism = synthetic construct
SEQUENCE: 181
RASHSVSSDY LA                                                    12

SEQ ID NO: 182            moltype = AA   length = 7
FEATURE                   Location/Qualifiers
REGION                    1..7
                          note = from human antibody library
source                    1..7
                          mol_type = protein
                          organism = synthetic construct
SEQUENCE: 182
GASSRAT                                                          7

SEQ ID NO: 183            moltype = AA   length = 9
FEATURE                   Location/Qualifiers
REGION                    1..9
                          note = from human antibody library
source                    1..9
                          mol_type = protein
                          organism = synthetic construct
SEQUENCE: 183
QQFDSSPPT                                                        9

SEQ ID NO: 184            moltype = AA   length = 109
FEATURE                   Location/Qualifiers
REGION                    1..109
                          note = from human antibody library
source                    1..109
                          mol_type = protein
                          organism = synthetic construct
SEQUENCE: 184
```

```
DIQMTQSPDT LSLSPGERAT LSCRASHSVS SDYLAWYQQK PGRAPRLLMY GASSRATGFP  60
DRFSGSGSGT DFSLTISRLE PEDFAVYYCQ QFDSSPPTFG GGTRIDIKR              109

SEQ ID NO: 185          moltype = AA  length = 10
FEATURE                 Location/Qualifiers
REGION                  1..10
                        note = consensus
VARIANT                 8
                        note = residue is V or I
VARIANT                 10
                        note = residue is G or L
source                  1..10
                        mol_type = protein
                        organism = synthetic construct
SEQUENCE: 185
GFTFSWYXMX                                                         10

SEQ ID NO: 186          moltype = AA  length = 17
FEATURE                 Location/Qualifiers
REGION                  1..17
                        note = consensus
VARIANT                 3
                        note = residue is Y or G
VARIANT                 4
                        note = residue is P or S
VARIANT                 8
                        note = residue is A or F
VARIANT                 10
                        note = residue is N or D
source                  1..17
                        mol_type = protein
                        organism = synthetic construct
SEQUENCE: 186
SIXXSGGXTX YADSVKG                                                 17

SEQ ID NO: 187          moltype =   length =
SEQUENCE: 187
000

SEQ ID NO: 188          moltype = AA  length = 13
FEATURE                 Location/Qualifiers
REGION                  1..13
                        note = consensus
VARIANT                 4
                        note = residue is S or T
VARIANT                 7
                        note = residue is I or L
VARIANT                 8
                        note = residue is E or G
VARIANT                 9
                        note = residue is T S or N
VARIANT                 10
                        note = residue is N or Y
VARIANT                 11
                        note = residue is T P A or Y
VARIANT                 12
                        note = residue is V or L
VARIANT                 13
                        note = residue is N I or Y
source                  1..13
                        mol_type = protein
                        organism = synthetic construct
SEQUENCE: 188
SGSXSNXXXX XXX                                                     13

SEQ ID NO: 189          moltype = AA  length = 14
FEATURE                 Location/Qualifiers
REGION                  1..14
                        note = consensus
VARIANT                 1
                        note = residue is A or T
VARIANT                 3
                        note = residue is S or T
VARIANT                 5
                        note = residue is H S or N
VARIANT                 7
                        note = residue is I or V
VARIANT                 9
                        note = residue is S or A
```

-continued

```
source                  1..14
                        mol_type = protein
                        organism = synthetic construct
SEQUENCE: 189
XGXSXDXGXY DYVS                                                    14

SEQ ID NO: 190          moltype =   length =
SEQUENCE: 190
000

SEQ ID NO: 191          moltype =   length =
SEQUENCE: 191
000

SEQ ID NO: 192          moltype = AA  length = 11
FEATURE                 Location/Qualifiers
REGION                  1..11
                        note = consensus
VARIANT                 2
                        note = residue is A S or T
VARIANT                 6
                        note = residue is N or S
VARIANT                 8
                        note = residue is N I or G
VARIANT                 9
                        note = residue is G or S
VARIANT                 10
                        note = residue is P W or V
VARIANT                 11
                        note = residue is V or L
source                  1..11
                        mol_type = protein
                        organism = synthetic construct
SEQUENCE: 192
AXWDDXLXXX X                                                       11

SEQ ID NO: 193          moltype = AA  length = 9
FEATURE                 Location/Qualifiers
REGION                  1..9
                        note = consensus
VARIANT                 7
                        note = residue is A or T
source                  1..9
                        mol_type = protein
                        organism = synthetic construct
SEQUENCE: 193
MYSTITXLL                                                          9

SEQ ID NO: 194          moltype = AA  length = 13
FEATURE                 Location/Qualifiers
REGION                  1..13
                        note = consensus
VARIANT                 4
                        note = residue is Q E or H
VARIANT                 5
                        note = residue is S R or N
VARIANT                 6
                        note = residue is V I or L
VARIANT                 7
                        note = residue is S R G or N
VARIANT                 8
                        note = residue is S or N
VARIANT                 9
                        note = residue is S N W or D
VARIANT                 10
                        note = residue is G or no amino acid
VARIANT                 12
                        note = residue is L or F
VARIANT                 13
                        note = residue is A G M or S
source                  1..13
                        mol_type = protein
                        organism = synthetic construct
SEQUENCE: 194
RASXXXXXXX YXX                                                     13

SEQ ID NO: 195          moltype = AA  length = 7
FEATURE                 Location/Qualifiers
REGION                  1..7
```

-continued

```
                            note = consensus
VARIANT                     4
                            note = residue is S T I or N
source                      1..7
                            mol_type = protein
                            organism = synthetic construct
SEQUENCE: 195
GASXRAT                                                         7

SEQ ID NO: 196      moltype =    length =
SEQUENCE: 196
000

SEQ ID NO: 197      moltype = AA   length = 7
FEATURE             Location/Qualifiers
REGION              1..7
                    note = Mutation of library member
source              1..7
                    mol_type = protein
                    organism = synthetic construct
SEQUENCE: 197
GFTFSWY                                                         7

SEQ ID NO: 198      moltype = AA   length = 6
FEATURE             Location/Qualifiers
REGION              1..6
                    note = Mutation of library member
source              1..6
                    mol_type = protein
                    organism = synthetic construct
SEQUENCE: 198
YPQGGA                                                          6

SEQ ID NO: 199      moltype = AA   length = 6
FEATURE             Location/Qualifiers
REGION              1..6
                    note = Mutation of library member
source              1..6
                    mol_type = protein
                    organism = synthetic construct
SEQUENCE: 199
GNYFDY                                                          6

SEQ ID NO: 200      moltype = AA   length = 115
FEATURE             Location/Qualifiers
REGION              1..115
                    note = Mutation of library member
source              1..115
                    mol_type = protein
                    organism = synthetic construct
SEQUENCE: 200
EVQLLESGGG LVQPGGSLRL SCAASGFTFS WYVMGWVRQA PGKGLEWVSS IYPQGGATSY  60
ADSVKGRFTI SRDNSKNTLY LQMNSLRAED TAVYYCARGN YFDYWGQGTL VTVSS       115

SEQ ID NO: 201      moltype = AA   length = 12
FEATURE             Location/Qualifiers
REGION              1..12
                    note = Mutation of library member
source              1..12
                    mol_type = protein
                    organism = synthetic construct
SEQUENCE: 201
RASQSVSSNY FG                                                   12

SEQ ID NO: 202      moltype = AA   length = 7
FEATURE             Location/Qualifiers
REGION              1..7
                    note = Mutation of library member
source              1..7
                    mol_type = protein
                    organism = synthetic construct
SEQUENCE: 202
GASSRAT                                                         7

SEQ ID NO: 203      moltype = AA   length = 9
FEATURE             Location/Qualifiers
REGION              1..9
                    note = Mutation of library member
source              1..9
```

-continued

```
                            mol_type = protein
                            organism = synthetic construct
SEQUENCE: 203
QQFDSLPLT                                                      9

SEQ ID NO: 204         moltype = AA  length = 109
FEATURE                Location/Qualifiers
REGION                 1..109
                       note = Mutation of library member
source                 1..109
                       mol_type = protein
                       organism = synthetic construct
SEQUENCE: 204
DIQMTQSPGT LSLSPGEGAT LSCRASQSVS SNYFGWYQQK PGQAPRLLIY GASSRATGIP  60
DRFSGSGSGT DFTLTISRLE PEDSAVYYCQ QFDSLPLTFG GGTKVEIKR             109

SEQ ID NO: 205         moltype = AA  length = 7
FEATURE                Location/Qualifiers
REGION                 1..7
                       note = Mutation of library member
source                 1..7
                       mol_type = protein
                       organism = synthetic construct
SEQUENCE: 205
GFTFSWY                                                        7

SEQ ID NO: 206         moltype = AA  length = 6
FEATURE                Location/Qualifiers
REGION                 1..6
                       note = Mutation of library member
source                 1..6
                       mol_type = protein
                       organism = synthetic construct
SEQUENCE: 206
YPQGGA                                                         6

SEQ ID NO: 207         moltype = AA  length = 6
FEATURE                Location/Qualifiers
REGION                 1..6
                       note = Mutation of library member
source                 1..6
                       mol_type = protein
                       organism = synthetic construct
SEQUENCE: 207
GNYFDY                                                         6

SEQ ID NO: 208         moltype = AA  length = 115
FEATURE                Location/Qualifiers
REGION                 1..115
                       note = Mutation of library member
source                 1..115
                       mol_type = protein
                       organism = synthetic construct
SEQUENCE: 208
EVQLLESGGG LVQPGGSLRL SCAASGFTFS WYVMSWVRQA PGKGLEWVSS IYPQGGATNY  60
ADSVKGRFTI SRDNSKNTLY LQMNSLRAED TAVYYCARGN YFDYWGQGTL VTVSS       115

SEQ ID NO: 209         moltype = AA  length = 12
FEATURE                Location/Qualifiers
REGION                 1..12
                       note = Mutation of library member
source                 1..12
                       mol_type = protein
                       organism = synthetic construct
SEQUENCE: 209
RASQSVSSNY FG                                                  12

SEQ ID NO: 210         moltype = AA  length = 7
FEATURE                Location/Qualifiers
REGION                 1..7
                       note = Mutation of library member
source                 1..7
                       mol_type = protein
                       organism = synthetic construct
SEQUENCE: 210
GASSRAT                                                        7

SEQ ID NO: 211         moltype = AA  length = 9
FEATURE                Location/Qualifiers
```

```
REGION                    1..9
                          note = Mutation of library member
source                    1..9
                          mol_type = protein
                          organism = synthetic construct
SEQUENCE: 211
QQHDSSPLS                                                              9

SEQ ID NO: 212            moltype = AA  length = 109
FEATURE                   Location/Qualifiers
REGION                    1..109
                          note = Mutated library sequence
source                    1..109
                          mol_type = protein
                          organism = synthetic construct
SEQUENCE: 212
DIQMTQSPGT LSLSPGEGAT LSCRASQSVS SNYFGWYQQK PGQAPRLLIY GASSRATGIP    60
DRFSGSGSGT DFTLTISRLE PEDSAVYYCQ QHDSSPLSFG GGTKVEIKR               109

SEQ ID NO: 213            moltype = AA  length = 7
FEATURE                   Location/Qualifiers
REGION                    1..7
                          note = Mutated library sequence
source                    1..7
                          mol_type = protein
                          organism = synthetic construct
SEQUENCE: 213
GFTFSWY                                                                7

SEQ ID NO: 214            moltype = AA  length = 6
FEATURE                   Location/Qualifiers
REGION                    1..6
                          note = Mutated library sequence
source                    1..6
                          mol_type = protein
                          organism = synthetic construct
SEQUENCE: 214
YPSGGA                                                                 6

SEQ ID NO: 215            moltype = AA  length = 6
FEATURE                   Location/Qualifiers
REGION                    1..6
                          note = Mutated library sequence
source                    1..6
                          mol_type = protein
                          organism = synthetic construct
SEQUENCE: 215
GNYLDY                                                                 6

SEQ ID NO: 216            moltype = AA  length = 115
FEATURE                   Location/Qualifiers
REGION                    1..115
                          note = Mutated library sequence
source                    1..115
                          mol_type = protein
                          organism = synthetic construct
SEQUENCE: 216
EVQLLESGGG LVQPGGSLRL SCAASGFTFS WYVMGWVRQA PGKGLEWVSS IYPSGGATNY    60
ADSVKGRFTI SRDNSKNTLY LQMNSLRAED TAVYYCARGN YLDYWGQGTL VTVSS        115

SEQ ID NO: 217            moltype = AA  length = 12
FEATURE                   Location/Qualifiers
REGION                    1..12
                          note = Mutated library sequence
source                    1..12
                          mol_type = protein
                          organism = synthetic construct
SEQUENCE: 217
RASQSVSSNY FG                                                         12

SEQ ID NO: 218            moltype = AA  length = 7
FEATURE                   Location/Qualifiers
REGION                    1..7
                          note = Mutated library sequence
source                    1..7
                          mol_type = protein
                          organism = synthetic construct
SEQUENCE: 218
GASSRAT                                                                7
```

```
SEQ ID NO: 219            moltype = AA   length = 9
FEATURE                   Location/Qualifiers
REGION                    1..9
                          note = Mutated library sequence
source                    1..9
                          mol_type = protein
                          organism = synthetic construct
SEQUENCE: 219
QQFDSSPLS                                                        9

SEQ ID NO: 220            moltype = AA   length = 109
FEATURE                   Location/Qualifiers
REGION                    1..109
                          note = Mutated library sequence
source                    1..109
                          mol_type = protein
                          organism = synthetic construct
SEQUENCE: 220
DIQMTQSPGT LSLSPGEGAT LSCRASQSVS SNYFGWYQQK PGQAPRLLIY GASSRATGIP  60
DRFSGSGSGT DFTLTISRLE PEDSAVYYCQ QFDSSPLSFG GGTKVEIKR              109

SEQ ID NO: 221            moltype = AA   length = 7
FEATURE                   Location/Qualifiers
REGION                    1..7
                          note = Mutated library sequence
source                    1..7
                          mol_type = protein
                          organism = synthetic construct
SEQUENCE: 221
GFTFSWY                                                           7

SEQ ID NO: 222            moltype = AA   length = 6
FEATURE                   Location/Qualifiers
REGION                    1..6
                          note = Mutated library sequence
source                    1..6
                          mol_type = protein
                          organism = synthetic construct
SEQUENCE: 222
YPSGGA                                                            6

SEQ ID NO: 223            moltype = AA   length = 6
FEATURE                   Location/Qualifiers
REGION                    1..6
                          note = Mutated library sequence
source                    1..6
                          mol_type = protein
                          organism = synthetic construct
SEQUENCE: 223
GPYLDY                                                            6

SEQ ID NO: 224            moltype = AA   length = 115
FEATURE                   Location/Qualifiers
REGION                    1..115
                          note = Mutated library sequence
source                    1..115
                          mol_type = protein
                          organism = synthetic construct
SEQUENCE: 224
EVQLLESGGG LVQPGGSLRL SCAASGFTFS WYVMGWVRQA PGKGLEWVSS IYPSGGATNY  60
ADSVKGRFTI SRDNSKNTLY LQMNSLRAED TAVYYCARGP YLDYWGQGTL VTVSS       115

SEQ ID NO: 225            moltype = AA   length = 12
FEATURE                   Location/Qualifiers
REGION                    1..12
                          note = Mutated library sequence
source                    1..12
                          mol_type = protein
                          organism = synthetic construct
SEQUENCE: 225
RASQSVSSNY FG                                                     12

SEQ ID NO: 226            moltype = AA   length = 7
FEATURE                   Location/Qualifiers
REGION                    1..7
                          note = Mutated library sequence
source                    1..7
                          mol_type = protein
```

-continued

```
                          organism = synthetic construct
SEQUENCE: 226
GASSRAT                                                           7

SEQ ID NO: 227            moltype = AA  length = 9
FEATURE                   Location/Qualifiers
REGION                    1..9
                          note = Mutated library sequence
source                    1..9
                          mol_type = protein
                          organism = synthetic construct
SEQUENCE: 227
QQFDSSPLT                                                         9

SEQ ID NO: 228            moltype = AA  length = 109
FEATURE                   Location/Qualifiers
REGION                    1..109
                          note = Mutated library sequence
source                    1..109
                          mol_type = protein
                          organism = synthetic construct
SEQUENCE: 228
DIQMTQSPGT LSLSPGEGAT LSCRASQSVS SNYFGWYQQK PGQAPRLLIY GASSRATGIP  60
DRFSGSGSGT DFTLTISRLE PEDSAVYYCQ QFDSSPLTFG GGTKVEIKR            109

SEQ ID NO: 229            moltype = AA  length = 7
FEATURE                   Location/Qualifiers
REGION                    1..7
                          note = Mutated library sequence
source                    1..7
                          mol_type = protein
                          organism = synthetic construct
SEQUENCE: 229
GFTFSWY                                                           7

SEQ ID NO: 230            moltype = AA  length = 6
FEATURE                   Location/Qualifiers
REGION                    1..6
                          note = Mutated library sequence
source                    1..6
                          mol_type = protein
                          organism = synthetic construct
SEQUENCE: 230
YPSGGA                                                            6

SEQ ID NO: 231            moltype = AA  length = 6
FEATURE                   Location/Qualifiers
REGION                    1..6
                          note = Mutated library sequence
source                    1..6
                          mol_type = protein
                          organism = synthetic construct
SEQUENCE: 231
GSYLDY                                                            6

SEQ ID NO: 232            moltype = AA  length = 115
FEATURE                   Location/Qualifiers
REGION                    1..115
                          note = Mutated library sequence
source                    1..115
                          mol_type = protein
                          organism = synthetic construct
SEQUENCE: 232
EVQLLESGGG LVQPGGSLRL SCAASGFTFS WYVMGWVRQA PGKGLEWVSS IYPSGGATNY  60
ADSVKGRFTI SRDNSKNTLY LQMNSLRAED TAVYYCARGS YLDYWGQGTL VTVSS      115

SEQ ID NO: 233            moltype = AA  length = 12
FEATURE                   Location/Qualifiers
REGION                    1..12
                          note = Mutated library sequence
source                    1..12
                          mol_type = protein
                          organism = synthetic construct
SEQUENCE: 233
RASQSVSSNY FG                                                     12

SEQ ID NO: 234            moltype = AA  length = 7
FEATURE                   Location/Qualifiers
REGION                    1..7
```

-continued

```
                         note = Mutated library sequence
source                   1..7
                         mol_type = protein
                         organism = synthetic construct
SEQUENCE: 234
GASSRAT                                                                      7

SEQ ID NO: 235           moltype = AA   length = 9
FEATURE                  Location/Qualifiers
REGION                   1..9
                         note = Mutated library sequence
source                   1..9
                         mol_type = protein
                         organism = synthetic construct
SEQUENCE: 235
QQFDSSPLT                                                                    9

SEQ ID NO: 236           moltype = AA   length = 109
FEATURE                  Location/Qualifiers
REGION                   1..109
                         note = Mutated library sequence
source                   1..109
                         mol_type = protein
                         organism = synthetic construct
SEQUENCE: 236
DIQMTQSPGT LSLSPGEGAT LSCRASQSVS SNYFGWYQQK PGQAPRLLIY GASSRATGIP   60
DRFSGSGSGT DFTLTISRLE PEDSAVYYCQ QFDSSPLTFG GGTKVEIKR               109

SEQ ID NO: 237           moltype = AA   length = 10
FEATURE                  Location/Qualifiers
REGION                   1..10
                         note = Mutated library sequence
source                   1..10
                         mol_type = protein
                         organism = synthetic construct
SEQUENCE: 237
GFTFSWYVMG                                                                   10

SEQ ID NO: 238           moltype = AA   length = 17
FEATURE                  Location/Qualifiers
REGION                   1..17
                         note = Mutated library sequence
source                   1..17
                         mol_type = protein
                         organism = synthetic construct
SEQUENCE: 238
SIYPQGGATS YADSVKG                                                           17

SEQ ID NO: 239           moltype = AA   length = 17
FEATURE                  Location/Qualifiers
REGION                   1..17
                         note = Mutated library sequence
source                   1..17
                         mol_type = protein
                         organism = synthetic construct
SEQUENCE: 239
SIYPQGGATN YADSVKG                                                           17

SEQ ID NO: 240           moltype = AA   length = 17
FEATURE                  Location/Qualifiers
REGION                   1..17
                         note = Mutated library sequence
source                   1..17
                         mol_type = protein
                         organism = synthetic construct
SEQUENCE: 240
SIYPSGGATN YADSVKG                                                           17

SEQ ID NO: 241           moltype = AA   length = 6
FEATURE                  Location/Qualifiers
REGION                   1..6
                         note = Mutated library sequence
source                   1..6
                         mol_type = protein
                         organism = synthetic construct
SEQUENCE: 241
GNYFDY                                                                       6

SEQ ID NO: 242           moltype = AA   length = 6
```

-continued

```
FEATURE              Location/Qualifiers
REGION               1..6
                     note = Mutated library sequence
source               1..6
                     mol_type = protein
                     organism = synthetic construct
SEQUENCE: 242
GNYLDY                                                                        6

SEQ ID NO: 243       moltype = AA  length = 6
FEATURE              Location/Qualifiers
REGION               1..6
                     note = Mutated library sequence
source               1..6
                     mol_type = protein
                     organism = synthetic construct
SEQUENCE: 243
GPYLDY                                                                        6

SEQ ID NO: 244       moltype = AA  length = 6
FEATURE              Location/Qualifiers
REGION               1..6
                     note = Mutated library sequence
source               1..6
                     mol_type = protein
                     organism = synthetic construct
SEQUENCE: 244
GSYLDY                                                                        6

SEQ ID NO: 245       moltype = AA  length = 12
FEATURE              Location/Qualifiers
REGION               1..12
                     note = Mutated library sequence
source               1..12
                     mol_type = protein
                     organism = synthetic construct
SEQUENCE: 245
RASQSVSSNY FG                                                                 12

SEQ ID NO: 246       moltype = AA  length = 7
FEATURE              Location/Qualifiers
REGION               1..7
                     note = Mutated library sequence
source               1..7
                     mol_type = protein
                     organism = synthetic construct
SEQUENCE: 246
GASSRAT                                                                       7

SEQ ID NO: 247       moltype = AA  length = 9
FEATURE              Location/Qualifiers
REGION               1..9
                     note = Mutated library sequence
source               1..9
                     mol_type = protein
                     organism = synthetic construct
SEQUENCE: 247
QQFDSLPLT                                                                     9

SEQ ID NO: 248       moltype = AA  length = 9
FEATURE              Location/Qualifiers
REGION               1..9
                     note = Mutated library sequence
source               1..9
                     mol_type = protein
                     organism = synthetic construct
SEQUENCE: 248
QQHDSSPLS                                                                     9

SEQ ID NO: 249       moltype = AA  length = 9
FEATURE              Location/Qualifiers
REGION               1..9
                     note = Mutated library sequence
source               1..9
                     mol_type = protein
                     organism = synthetic construct
SEQUENCE: 249
QQFDSSPLS                                                                     9
```

-continued

```
SEQ ID NO: 250          moltype = AA   length = 9
FEATURE                 Location/Qualifiers
REGION                  1..9
                        note = Mutated library sequence
source                  1..9
                        mol_type = protein
                        organism = synthetic construct
SEQUENCE: 250
QQFDSSPLT                                                           9

SEQ ID NO: 251          moltype = AA   length = 5
FEATURE                 Location/Qualifiers
REGION                  1..5
                        note = glycine serine linker
source                  1..5
                        mol_type = protein
                        organism = synthetic construct
SEQUENCE: 251
GGGGS                                                               5

SEQ ID NO: 252          moltype = AA   length = 10
FEATURE                 Location/Qualifiers
REGION                  1..10
                        note = glycine serine linker
source                  1..10
                        mol_type = protein
                        organism = synthetic construct
SEQUENCE: 252
GGGGSGGGGS                                                         10
```

HUMAN ANTI-VEGFR-2/KDR ANTIBODIES

CROSS-REFERENCE TO RELATED APPLICATIONS

This application is a divisional of U.S. application Ser. No. 16/799,977, filed Feb. 25, 2020, which is a divisional of U.S. application Ser. No. 15/517,778, filed Apr. 7, 2017, now U.S. Pat. No. 10,588,968, which is a national phase entry pursuant to 35 U.S.C. § 371 of International Application No. PCT/US2015/054569, filed Oct. 7, 2015, which claims priority to U.S. Application No. 62/061,097, filed on Oct. 7, 2014, the entire contents of which are incorporated by reference herein for all purposes.

This application also relates to PCT/US2013/063754, filed Oct. 7, 2013, and to U.S. Ser. No. 61/710,420, filed Oct. 5, 2012, both of which are incorporated herein by reference in their entireties.

FIELD OF THE INVENTION

The invention relates to antibodies that bind to VEGFR-2. The antibodies are used for treating neoplastic diseases and hyperproliferative disorders, and can be used alone or in combination with other agents.

SEQUENCE LISTING

The present application contains a Sequence Listing which has been submitted electronically in XML format. Said XML copy, created on Mar. 7, 2023, is named "2023-03-6_01183-0203-02US-KAD-ST26.xml" and is 330,401 bytes in size. The information in the electronic format of the sequence listing is incorporated herein by reference in its entirety.

BACKGROUND OF THE INVENTION

Angiogenesis is a highly complex process of developing new blood vessels that involves the proliferation and migration of, and tissue infiltration by capillary endothelial cells from pre-existing blood vessels, cell assembly into tubular structures, joining of newly forming tubular assemblies to closed-circuit vascular systems, and maturation of newly formed capillary vessels.

Angiogenesis is important in normal physiological processes including embryonic development, follicular growth, and wound healing. Undue angiogenesis also leads to neovascularization in neoplastic diseases, and in non-neoplastic diseases such as age-related macular degeneration (AMD), diabetic retinopathy, and neovascular glaucoma. Anti-angiogenic therapy that targets vascular endothelial growth factor (VEGF) with ranibizumab (Lucentis) has been shown to be effective in delaying progression of AMD. However, neovascularization is complex and multiple angiogenic mechanisms are likely to contribute. There remains a need to develop agents and therapies for treating diseases associated with neovascularization.

SUMMARY OF THE INVENTION

The present invention provides human antibodies, and fragments thereof that bind to VEGFR-2 (KDR). In some embodiments, the antibodies block ligand binding (e.g., one or more of VEGF-A, VEGF-C, VEGF-D, or VEGF-E) to VEGFR-2. In some embodiments, the antibodies neutralize activation of VEGFR-2. The antibodies are used for treating neoplastic diseases, including, for example, solid and non-solid tumors, and hyperproliferative disorders. Accordingly, the invention provides methods of neutralizing the activation of KDR, methods of inhibiting tumor growth, including inhibition of tumor associated angiogenesis, and methods of treating angiogenesis related disorders. The present invention provides kits having human antibodies or antibody fragments that bind to VEGR receptors.

In one embodiment, the invention provides an isolated antibody or fragment thereof that binds to human VEGFR2, comprising a heavy chain variable domain, which comprises a CDR1, a CDR2, and a CDR3 sequence, wherein:
(i) the CDR1 sequence is GFTFSWYVMG (SEQ ID NO: 237),
(ii) the CDR2 sequence is selected from the group consisting of

```
                              (SEQ ID NO: 238)
        SIYPQGGATSYADSVKG, (SEQ ID NO: 239)
        SIYPQGGATNYADSVKG,
        and (SEQ ID NO: 240)
        SIYPSGGATNYADSVKG;
```
and
(ii) the CDR3 sequence selected from the group consisting of

```
                              (SEQ ID NO: 241)
        GNYFDY, (SEQ ID NO: 242)
        GNYLDY, (SEQ ID NO: 243)
        GPYLDY
        and (SEQ ID NO: 244)
        GSYLDY,
``` with the proviso that the heavy chain variable domain does not comprise both the CDR2 sequence of SEQ ID NO: 240 and the CDR3 sequecne of SEQ ID NO: 241.

In one embodiment, the invention provides an isolated antibody or fragment thereof that binds to human VEGFR2, comprising a light chain variable domain, which comprises a CDR1, a CDR2, and a CDR3 sequence, wherein
(i) the CDR1 sequence is RASQSVSSNYFG (SEQ ID NO: 245),
(ii) the CDR2 sequence is GASSRAT (SEQ ID NO: 246), and
(iii) the CDR3 sequence is selected from the group consisting of

```
                              (SEQ ID NO: 247)
        QQFDSLPLT, (SEQ ID NO: 248)
        QQHDSSPLS, (SEQ ID NO: 249)
        QQFDSSPLS,
        and (SEQ ID NO: 250)
        QQFDSSPLT.
```

In one embodiment of the invention, the CDR2 of the heavy chain variable domain has the sequence SIYPQG-GATSYADSVKG (SEQ ID NO: 238), and the CDR3 of the heavy chain variable domain has the sequence GNYFDY (SEQ ID NO: 241).

In one embodiment of the invention, the CDR3 of the light chain variable domain has the sequence QQFDSLPLT (SEQ ID NO: 247).

In one embodiment of the invention, the heavy chain variable domain has a sequence that is selected from the group consisting of

```
                                    (SEQ ID NO: 200)
EVQLLESGGGLVQPGGSLRLSCAASGFTFSWYVMGWVRQAPGKGLEWVS

SIYPQGGATSYADSVKGRFTISRDNSKNTLYLQMNSLRAEDTAVYYCAR

GNYFDYWGQGTLVTVSS, (SEQ ID NO: 208)
EVQLLESGGGLVQPGGSLRLSCAASGFTFSWYVMSWVRQAPGKGLEWVS

SIYPQGGATNYADSVKGRFTISRDNSKNTLYLQMNSLRAEDTAVYYCAR

GNYFDYWGQGTLVTVSS, (SEQ ID NO: 216)
EVQLLESGGGLVQPGGSLRLSCAASGFTFSWYVMGWVRQAPGKGLEWVS

SIYPSGGATNYADSVKGRFTISRDNSKNTLYLQMNSLRAEDTAVYYCAR

GNYLDYWGQGTLVTVSS, (SEQ ID NO: 224)
EVQLLESGGGLVQPGGSLRLSCAASGFTFSWYVMGWVRQAPGKGLEWVS

SIYPSGGATNYADSVKGRFTISRDNSKNTLYLQMNSLRAEDTAVYYCAR

GPYLDYWGQGTLVTVSS,
and (SEQ ID NO: 232)
EVQLLESGGGLVQPGGSLRLSCAASGFTFSWYVMGWVRQAPGKGLEWVS

SIYPSGGATNYADSVKGRFTISRDNSKNTLYLQMNSLRAEDTAVYYCAR

GSYLDYWGQGTLVTVSS.
```

In one embodiment of the invention, the light chain variable domain has a sequence that is selected from the group consisting of

```
                                    (SEQ ID NO: 204)
DIQMTQSPGTLSLSPGEGATLSCRASQSVSSNYFGWYQQKPGQAPRLLI

YGASSRATGIPDRFSGSGSGTDFTLTISRLEPEDSAVYYCQQFDSLPLT

FGGGTKVEIKR, (SEQ ID NO: 212)
DIQMTQSPGTLSLSPGEGATLSCRASQSVSSNYFGWYQQKPGQAPRLLI

YGASSRATGIPDRFSGSGSGTDFTLTISRLEPEDSAVYYCQQHDSSPLS

FGGGTKVEIKR, (SEQ ID NO: 220)
DIQMTQSPGTLSLSPGEGATLSCRASQSVSSNYFGWYQQKPGQAPRLLI

YGASSRATGIPDRFSGSGSGTDFTLTISRLEPEDSAVYYCQQFDSSPLS

FGGGTKVEIKR,
```

-continued

```
                                    (SEQ ID NO: 228)
DIQMTQSPGTLSLSPGEGATLSCRASQSVSSNYFGWYQQKPGQAPRLLI

YGASSRATGIPDRFSGSGSGTDFTLTISRLEPEDSAVYYCQQFDSSPLT

FGGGTKVEIKR,
and (SEQ ID NO: 236)
DIQMTQSPGTLSLSPGEGATLSCRASQSVSSNYFGWYQQKPGQAPRLLI

YGASSRATGIPDRFSGSGSGTDFTLTISRLEPEDSAVYYCQQFDSSPLT

FGGGTKVEIKR.
```

In one embodiment of the invention, the heavy chain variable domain has a sequence that is

```
                                    (SEQ ID NO: 200)
EVQLLESGGGLVQPGGSLRLSCAASGFTFSWYVMGWVRQAPGKGLEWVS

SIYPQGGATSYADSVKGRFTISRDNSKNTLYLQMNSLRAEDTAVYYCAR

GNYFDYWGQGTLVTVSS,
and the light chain variable domain has a sequence
that is
                                    (SEQ ID NO: 204)
DIQMTQSPGTLSLSPGEGATLSCRASQSVSSNYFGWYQQKPGQAPRLLI

YGASSRATGIPDRFSGSGSGTDFTLTISRLEPEDSAVYYCQQFDSLPLT

FGGGTKVEIKR.
```

In one embodiment of the invention, the antibody or fragment has isotype IgG.

In one embodiment of the invention, the antibody or fragment is an scFv, Fv, Fab', Fab, F(ab')2, or diabody.

In one embodiment of the invention, the the antibody or fragment binds to human VEGFR2 and murine hVEGFR2.

The present invention provides an isolated nucleic acid encoding the antibody or fragment of the present invention.

The present invention provides a nucleic acid vector comprising an isolated nucleic acid encoding the antibody or fragment of the present invention.

The present invention provides a prokaryotic or eukary-otic host cell comprising an isolated nucleic acid encoding the antibody or fragment of the present invention.

The present invention provides a composition comprising an antibody or fragment of the present invention, and a pharmaceutically acceptable carrier.

The present invention provides a method of neutralizing activation of human VEGFR2 or murine VEGFR2 compris-ing contacting a cell with an effective amount of an antibody or fragment of the present invention.

The present invention provides a method of inhibiting angiogenesis comprising administering to a subject an effec-tive amount of an antibody or fragment of the present invention.

The present invention provides a method of reducing tumor growth comprising administering to a subject an effective amount of an antibody or fragment of the present invention.

The present invention provides a method of treating a neoplastic diseases in a subject, comprising administering to a subject an effective amount of an antibody or fragment of the present invention, wherein the neoplastic diseases is selected from the group consitring of lung cancer, colorectal cancer renal cell carcinoma, glioblastoma, ovarian cancer, bladder cancer, gastric cancer, multiple myeloma, non-small cell lung cancer and pancreatic cancer.

In one embodiment of the invention, the method which further comprises administering to a subject an effective amount of an epidermal growth factor receptor (EGFR) antagonist.

In one embodiment of the invention, the method which further comprises administering to a subject an effective amount of an fms-like tyrosine kinase receptor (flt-1) antagonist.

In one embodiment of the invention, the method which further comprises administering to a subject an effective amount of a rho associated kinase 2 (ROCK2) antagonist.

In one embodiment of the invention, the method which further comprises administering to a subject an effective amount of a matrix metalloproteinase antagonist.

In one embodiment of the invention, the method which further comprises administering to a subject an effective amount of a PDGFRβ antibody.

In one embodiment of the invention, the method which further comprises administering to a subject an effective amount of a PD-L1 antibody.

In one embodiment of the invention, the patient is a human.

BRIEF DESCRIPTION OF THE FIGURES

FIGS. 1A-C show human heavy chain, lambda light chain, and kappa light chain variable region sequences, respectively, of anti-VEGFR2 antibodies of the invention identified by phage display.

FIG. 2 shows binding of antibodies of the invention to hVEGFR2 (top) and a construct containing domains 2 and 3 of hVEGFR2 (middle). The bottom panel shows ligand (VEGF$_{165}$) blocking.

FIG. 4 shows binding to hVEGFR2 and VEGF$_{165}$ ligand blocking by Mabs 104, 105, 106, and 108. Similar results were obtained for Mabs 103, 107, 109, and 110 in a separate experiment. These Mabs contain the heavy chain variable domain of Mab101, recombined with different light chain variable domains.

FIG. 6A depicts heavy chain amino acid sequences of five affinity matured antibodies derived from Mab 138, which contains the V$_H$ domain having SEQ ID NO:4 (sequence aso shown in this Figure). FIG. 6B depicts light chain amino acid sequences of the same five affinity matured antibodies derived from SEQ ID NO: 160 (sequence aso shown in this Figure).

6

Mab 106 blocks the binding of human VEGF with human VEGFR2 but not the binding of murine VEGF with murine VEGFR2.

Figures 8A, 8B:
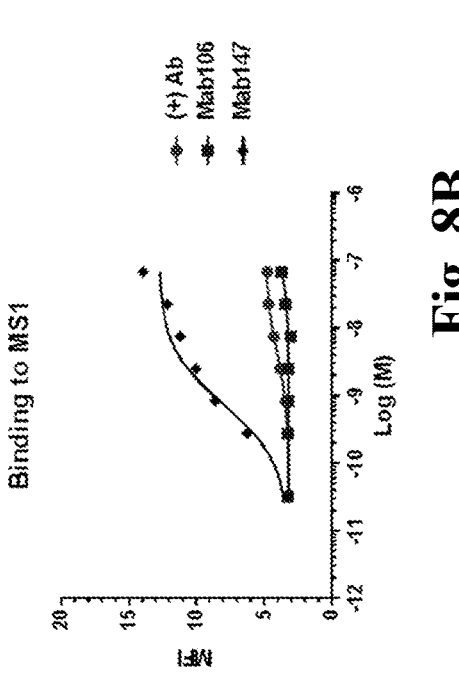

FIG. 8A depicts the binding of Mab106 and Mab 147 to human VEGFR2 on HUVEC (Human Umbilical Vein Endothelial Cells) and porcine aortic endothelial (PAE) cells overexpressing KDR (KDR-PAE). FIG. 8B show Mab 147, but not Mab 106, binds to VEGFR2 on MS1 murine endothelial cells. In FIGS. 8A and 8B, the control is an antibody that binds to hVEGFR2 but not m VEGFR2.

FIG. 9 shows inhibition of VEGFR2-mediated signal transduction by Mab 106 and Mab 147. Mab 106 and Mab 147 inhibit phosphorylation of KDR and p44/42 in KDR-PAE (FIG. 9A) cells and in HUVEC (FIG. 9B) in a dose dependent manner.

Figure 10A:
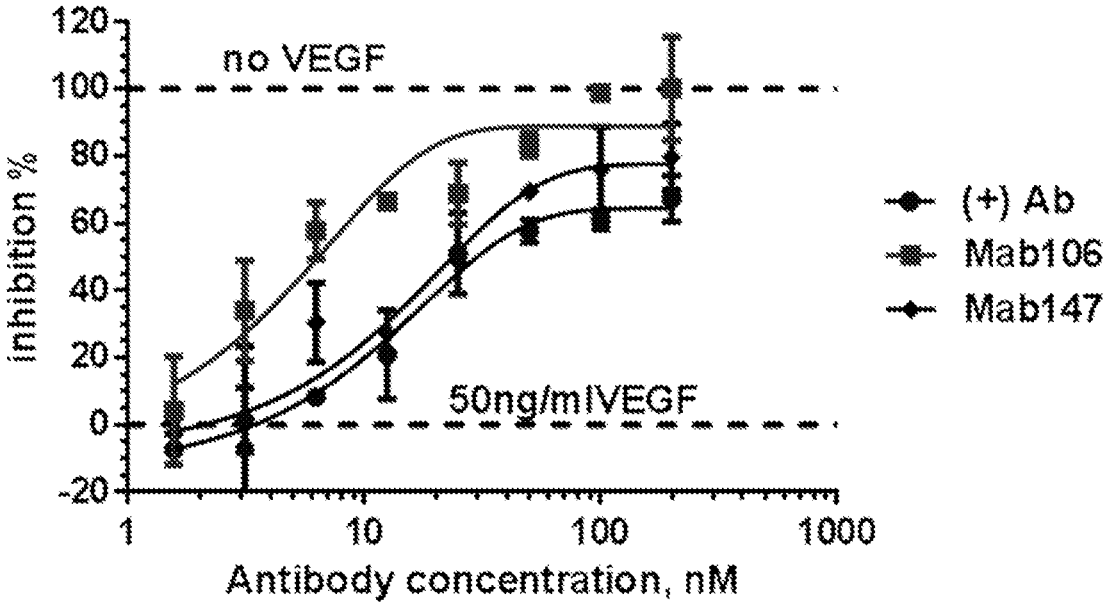
Figure 10B:
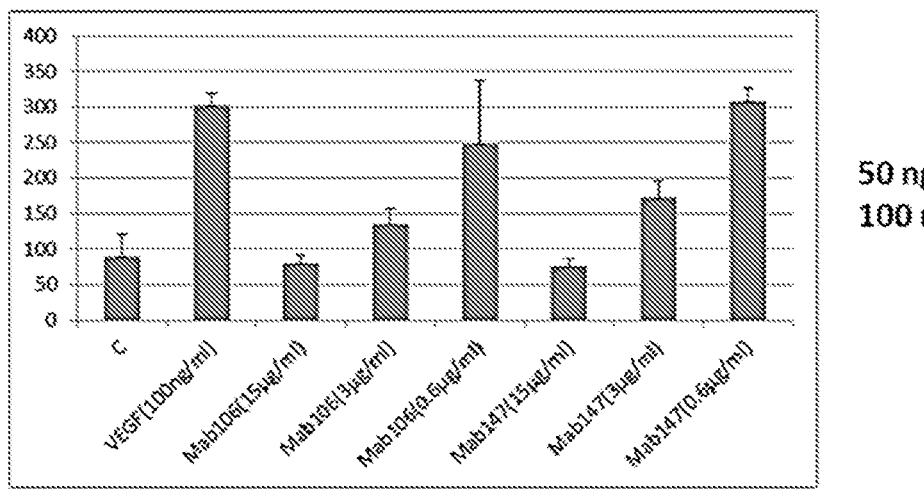

FIG. 10A depicts inhibition of proliferation of KDR-PAE cells by Mab 106, Mab 147, and a control antibody that binds to hVEGFR2. FIG. 10B shows inhibition of induced cell migration. Migration of KDR-PAE cells was induced with a VEGF gradient (50 ng/ml VEGF (up), 100 ng/ml VEGF (low)). The plot depicts cell counts in the presence of 0.6 μg/ml, 3 μg/ml, or 15 μg/ml of Mab 106 or Mab 147 antibody.

Figure 11:
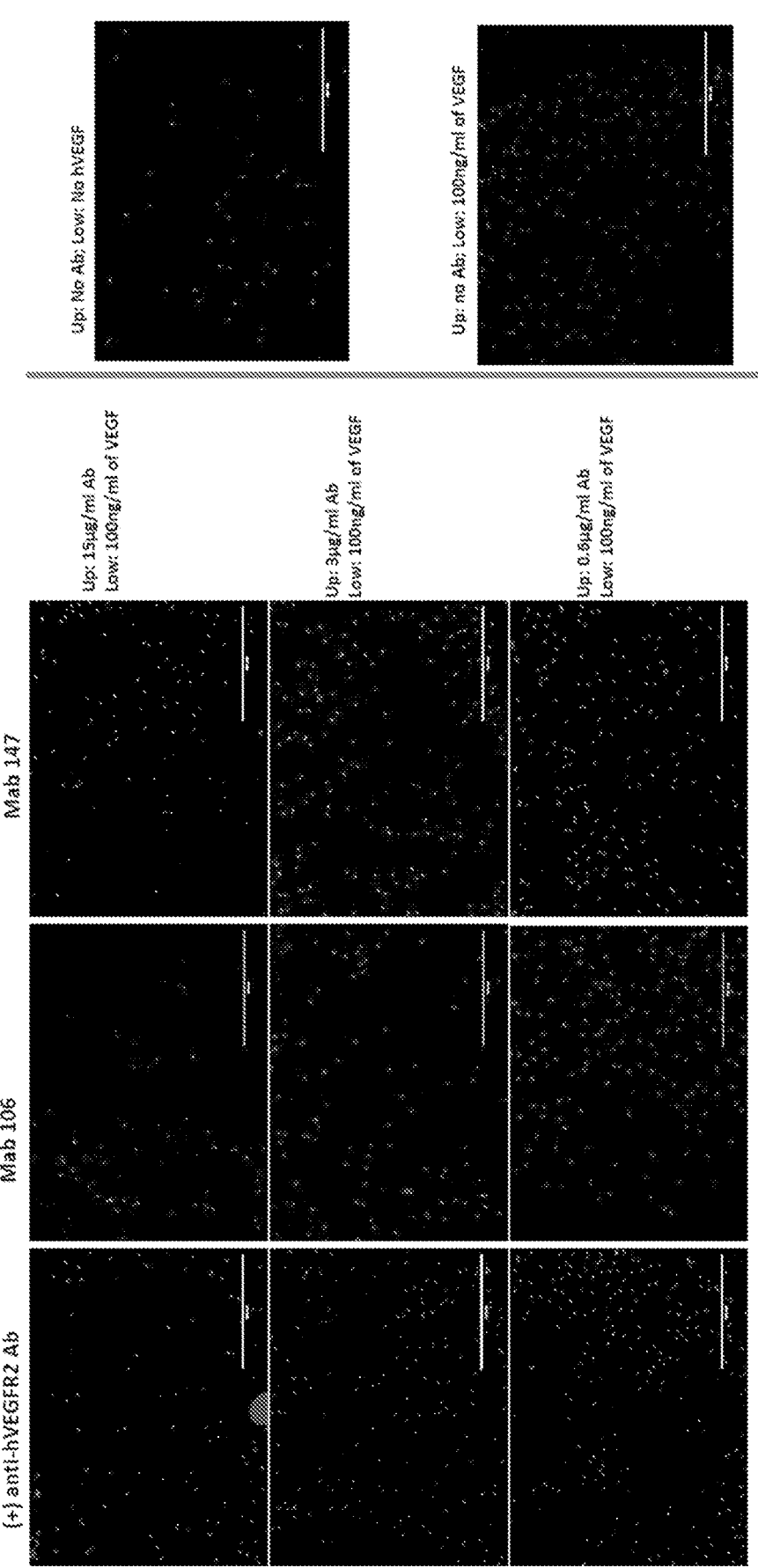

FIG. 11 depicts inhibition of VEGF-induced migration of KDR-PAE cells by Mab 147.

Figure 12A:
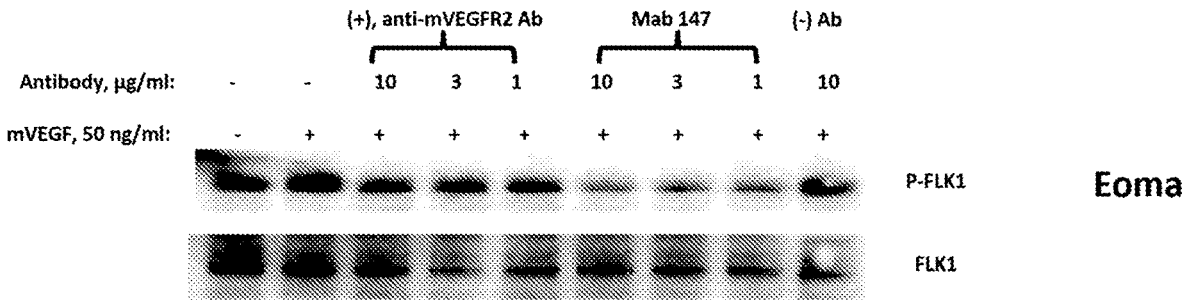
Figure 12B:
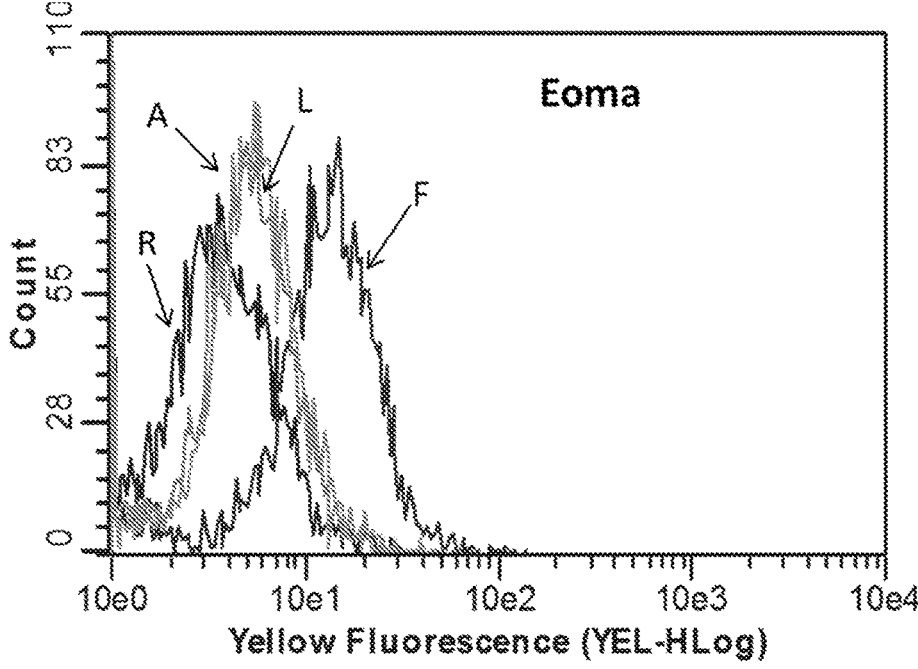

FIG. 12A depicts inhibition of VEGFR2-mediated signal transduction in murine EOMA cells by Mab 147. And FIG. 12B depicts FACS studies demonstaring that Mab 147 has increased binding to EOMA cells by comparison to control antibodies.

DETAILED DESCRIPTION

In one aspect, the invention provides novel VEGFR2 antibodies or antigen binding fragments of such antibodies are employed, which are effective to inhibit VEGFR2-dependent signal transduction. As used herein, "inhibiting a receptor" means diminishing and/or inactivating the intrinsic kinase activity of the receptor to transduce a signal. A reliable assay for VEGFR2 inhibition is reduction of receptor phosphorylation.

The present invention is not limited by any particular mechanism of VEGFR2 inhibition. The mechanism followed by one antibody is not necessarily the same as that followed by another. Some possible mechanisms include preventing binding of the VEGF ligand to the extracellular binding domain of the VEGFR2, and preventing dimerization or oligomerization of receptors. Other mechanisms cannot, however, be ruled out.

Antibodies are proteins that recognize and bind to a specific antigen or substance. In preferred embodiments, the antibodies of the present invention bind KDR at least as strongly as the natural ligand. Affinity, represented by the equilibrium constant for the dissociation of an antigen with an antibody (Kd), measures the binding strength between an antigenic determinant and an antibody binding site. Avidity is the measure of the strength of binding between an antibody with its antigen. Avidity is related to both the affinity between an antigenic determinant and an antigen binding site on the antibody, and the number of binding sites (valence) per antibody. For example, a monovalent antibody (e.g., Fab) has one binding site for a particular epitope. An IgG antibody has two antigen binding sites. Typical values of K (the reciprocal of the dissociation constant K$_d$) are $10^5$ to $10^{11}$ liters/mol. Any K weaker than $10^4$ liters/mol is considered to indicate binding which is nonspecific.

Antibodies of the invention inhibit activation of VEGFR2. One measure of VEGFR2 inhibition is reduced tyrosine kinase activity of the receptor. Tyrosine kinase inhibition can be determined using well-known methods, such as measuring the autophosphorylation level of the receptor. Inhibition of VEGFR2 can also be observed through inhibition or regulation of phosphorylation events of natural or synthetic VEGFR2 substrates and other components of the VEGFR2 signal transduction pathway. Phosphorylation can be detected, for example, using an antibody specific for phosphotyrosine in an ELISA assay or on a western blot. Some assays for tyrosine kinase activity are described in Panek et al., *J. Pharmacol. Exp. Thera.*, 283: 1433-44 (1997) and Batley et al., *Life Sci.*, 62:143-50 (1998).

In vivo assays can also be utilized. For example, receptor tyrosine kinase inhibition can be observed by mitogenic assays using cell lines stimulated with receptor ligand in the presence and absence of inhibitor. For example, HUVEC cells (ATCC) stimulated with VEGF can be used to assay VEGFR inhibition. Another method involves testing for inhibition of growth of VEGF-expressing tumor cells, using for example, human tumor cells injected into a mouse. See, U.S. Pat. No. 6,365,157 (Rockwell et al.).

The invention provides anti-VEGFR2 antibodies, including nucleic acids encoding such antibodies and compositions comprising such antibodies. In one embodiment the invention provides an isolated antibody heavy chain variable region comprising a CDR-1H, CDR-2H, and CDR-3H sequence, wherein:

(i) the CDR-1H sequence is GFTFSWYX$_1$MX$_2$ (SEQ ID NO:185), wherein X$_1$ is V or I, X$_2$ is G or L, (ii) the CDR-2H sequence is SIX$_1$X$_2$SGGX$_3$TX$_4$YADSVKG (SEQ ID NO:186), wherein X$_1$ is Y or G, X$_2$ is P or S, X$_3$ is A or F, X$_4$ is N or D, and (iii) the CDR-3H sequence is GNYFDY (SEQ ID NO:3) or GLAAPRS (SEQ ID NO: 11).

In one embodiment, the invention provides an isolated light chain variable region comprising a CDR-L1, CDR-L2, and CDR-L3, wherein (i) the CDR-L1 sequence is X$_1$GX$_2$X$_3$LX$_4$X$_5$X$_6$X$_7$X$_8$S (SEQ ID NO:187), wherein X$_1$ is S, Q, or T, X$_2$ is D, E, or Q, X$_3$ is K, S, N, I, or A, X$_4$ is G or R, X$_5$ is D, S, H, E, or N, X$_6$ is E, Y, Q, R, or N, X$_7$ is Y, F, or S, and X$_8$ is A or S, or SGSX$_1$SNX$_2$X$_3$X$_4$X$_5$X$_6$X$_7$X$_8$ (SEQ ID NO: 188), wherein X$_1$ is S, or T, X$_2$ is I or L, X$_3$ is E or G, X$_4$ is T, S, or N, X$_5$ is N or Y, X$_6$ is T, P, A, or Y, X$_7$ is V or L, and X$_8$ is N, I, or Y, or X$_1$GX$_2$SX$_3$DX$_4$GX$_5$YDYVS (SEQ ID NO: 189), wherein X$_1$ is A or T, X$_2$ is S or T, X$_3$ is H, S, or N, X$_4$ is I or V, and X$_5$ is S or A, (ii) the CDR-L2 sequence is X$_1$X$_2$X$_3$X$_4$X$_5$PS (SEQ ID NO:190), wherein wherein X$_1$ is Q, D, T, Y, S, or A, X$_2$ is D, N, S, T, or V, X$_3$ is D, N, S, T, or Y, X$_4$ is Q, K, N, or L, and X$_5$ is R or L, and (iii) wherein the CDR-L3 sequence is QX$_1$WX$_2$X$_3$X$_4$X$_5$X$_6$X$_7$X$_8$ (SEQ ID NO:191), wherein X$_1$ is A or T, X$_2$ is D or G, X$_3$ is R or no amino acid, X$_4$ is S, F, or N, X$_5$ is S, T, or N, X$_6$ is S, T, or P, X$_7$ is A, V, L, I, or Y, and X$_8$ is V or L, or AX$_1$WDDX$_2$LX$_3$X$_4$X$_5$X$_6$ (SEQ ID NO: 192), wherein X$_1$ is A, S, or T, X$_2$ is N or S, X$_3$ is N, I, or G, X$_4$ is G or S, X$_5$ is P, W, or V, and X$_6$ is V or L, or MYSTITX$_1$LL (SEQ ID NO:193), wherein X$_1$ is A or T.

In one embodiment, the invention provides an isolated light chain variable region comprising a CDR-L1, CDR-L2, and CDR-L3, wherein (i) the CDR-L1 sequence is RASX$_1$X$_2$X$_3$X$_4$X$_5$X$_6$X$_7$YX$_8$X$_9$ (SEQ ID NO:194), wherein X$_1$ is Q, E, or H, X$_2$ is S, R, or N, X$_3$ is V, I, or L, X$_4$ is S, R, G or N, X$_5$ is S or N, X$_6$ is S, N, W, or D, X$_7$ is G or no amino acid, X$_8$ is L or F, and X$_9$ is A, G, M, or S, (ii) the CDR-L2 sequence is GASX$_1$RAT (SEQ ID NO:195), wherein X$_1$ is S, T, I, or N, and (iii) the CDR-L3 sequence is QQX$_1$X$_2$X$_3$X$_4$X$_5$X$_6$X$_7$X$_8$ (SEQ ID NO:196), wherein X$_1$ is F or Y, X$_2$ is D, G, or Y, X$_3$ is S, T, or N, X$_4$ is S, L, or W, X$_5$ is P or no amino acid, X$_6$ is P or T, X$_7$ is L, I, V, P, W, or Y, and X$_8$ is T or S.

In an embodiment of the invention, an antibody is provided which comprises a heavy chain variable domain comprising one, two, three, four, five, or six of the light chain varible domain and heavy chain variable domain CDR sequences set forth above.

Non-limiting examples of VEGFR2-binding antibody sequences are provided. As described herein, from human Fab phage display libraries, two neutralizing antibodies were identified that bind to human VEGFR2, block binding of the ligand VEGFA to hVEGFR2, and inhibit the VEGFR2 phosphorylation and downstream signal transduction stimulated by VEGFA. Table 1 indicates amino acid sequences of the CDRs and variable domains of antibodies of the antibodies. The Kas of Mab 101 and Mab 102 are about 6.6 mM and 1.7 nM, respectively.

TABLE 1

| | Antibody Amino Acid Sequences by SEQ ID NO | | | | | | | |
|---|---|---|---|---|---|---|---|---|
| Mab | CDR-H1 | CDR-H2 | CDR-H3 | $V_H$ domain | CDR-L1 | CDR-L2 | CDR-L3 | $V_L$ domain |
| 101 | 1 | 2 | 3 | 4 | 5 | 6 | 7 | 8 |
| 102 | 9 | 10 | 11 | 12 | 13 | 14 | 15 | 16 |

The heavy chain of Mab 101 was reshuffled with κ light chain genes (κ-library) and λ light chain genes (λ-library). 20 unique λ light chain variants were found by panning the λ-library against both human VEGFR2 and mouse VEGFR2. 22 unique κ light chain variants were found by panning the κ-library against both human VEGFR2 and mouse VEGFR2. Table 2 indicates amino acid sequences of the CDRs and variable domains of the light chains. The Kas of Mabs 105, 106, and 107 were increased about 10 fold (0.24 nM, 0.22 nM, and 0.12 nM, respectively). Like the parent antibody, these antibodies bind to VEGFR2 and block binding of VEGFA to VEGFR2, and inhibit VEGFA-stimulated phosphorylation of VEGFR2, AKT, and MAPK. (FIG. 4).

Several of the antibodies, including Mabs 138, 139, 140, and 146, also cross react with mouse VEGFR2. These antibodies also inhibited VEGFA-stimulated phosphorylation of VEFGR2 and downstream signal transduction molecules, including MAPK.

TABLE 2

| | | SEQ ID NO | | | |
|---|---|---|---|---|---|
| Mab | light chain | CDR-L1 | CDR-L2 | CDR-L3 | $V_L$ |
| 103 | λ | 17 | 18 | 19 | 20 |
| 104 | λ | 21 | 22 | 23 | 24 |
| 105 | λ | 25 | 26 | 27 | 28 |
| 106 | λ | 29 | 30 | 31 | 32 |
| 107 | λ | 33 | 34 | 35 | 36 |
| 108 | λ | 37 | 38 | 39 | 40 |
| 109 | λ | 41 | 42 | 43 | 44 |
| 110 | λ | 45 | 46 | 47 | 48 |
| 111 | λ | 49 | 50 | 51 | 52 |
| 112 | λ | 53 | 54 | 55 | 56 |
| 113 | λ | 57 | 58 | 59 | 60 |
| 114 | λ | 61 | 62 | 63 | 64 |
| 115 | λ | 65 | 66 | 67 | 68 |
| 116 | λ | 69 | 70 | 71 | 72 |
| 117 | λ | 73 | 74 | 75 | 76 |
| 118 | λ | 77 | 78 | 79 | 80 |
| 119 | λ | 81 | 82 | 83 | 84 |
| 120 | λ | 85 | 86 | 87 | 88 |
| 121 | λ | 89 | 90 | 91 | 92 |
| 122 | λ | 93 | 94 | 95 | 96 |
| 123 | κ | 97 | 98 | 99 | 100 |
| 124 | κ | 101 | 102 | 103 | 104 |
| 125 | κ | 105 | 106 | 107 | 108 |
| 126 | κ | 109 | 110 | 111 | 112 |
| 127 | κ | 113 | 114 | 115 | 116 |
| 128 | κ | 117 | 118 | 119 | 120 |
| 129 | κ | 121 | 122 | 123 | 124 |
| 130 | κ | 125 | 126 | 127 | 128 |
| 131 | κ | 129 | 130 | 131 | 132 |
| 132 | κ | 133 | 134 | 135 | 136 |
| 133 | κ | 137 | 138 | 139 | 140 |
| 134 | κ | 141 | 142 | 143 | 144 |
| 135 | κ | 145 | 146 | 147 | 148 |
| 136 | κ | 149 | 150 | 151 | 152 |
| 137 | κ | 153 | 154 | 155 | 156 |
| 138 | κ | 157 | 158 | 159 | 160 |
| 139 | κ | 161 | 162 | 163 | 164 |
| 140 | κ | 165 | 166 | 167 | 168 |
| 141 | κ | 169 | 170 | 171 | 172 |
| 142 | κ | 173 | 174 | 175 | 176 |
| 143 | κ | 177 | 178 | 179 | 180 |
| 144 | κ | 181 | 182 | 183 | 184 |

κ and λ light chains by SEQ ID NO

The invention provides an isolated VEGFR2 antibody, and VEGFR2 binding fragments thereof, which comprises one, two, or three heavy chain CDRs and one, two, or three light chain CDRs, selected from the sequences set forth in Table 1 and Table 2. In an antibody of the invention, when more than one CDR is selected from the sequences presented in Table 1 and Table 2, the different CDRs need not be selected from the same monoclonal antibody presented in those tables, but can be selected from two or more antibody variable domains presented in the tables. Specific embodiments include, but are not limited to, the following. In an embodiment of the invention, the isolated VEGFR2 antibody comprises one, two, or three heavy chain CDRs having SEQ ID NO:1, SEQ ID NO:2, and SEQ ID NO:3. In an embodiment, of the invention, the antibody comprises one, two, or three light chain CDRs having SEQ ID NO:5, SEQ ID NO:6, and SEQ ID NO:7. In another embodiment, the antibody comprises one, two, or three light chain CDRs having sequences as set forth in Table 1 or 2. Non-limiting examples include a light chain variable region comprising one or more of SEQ ID NO:25, SEQ ID NO:26, and SEQ ID NO:27, one or more of SEQ ID NO: 29, SEQ ID NO:30, and SEQ ID NO:31, or one or more of SEQ ID NO:33, SEQ ID NO: 34, and SEQ ID NO:35. In certain embodiments, the VEGFR2 antibody comprises a heavy chain variable domain comprising SEQ ID NO:4 or SEQ ID NO: 12. In certain embodiments, the VEGFR2 antibody comprises a light chain variable domain comprising SEQ ID NO:8, SEQ ID NO: 16, SEQ ID NO:27, SEQ ID NO:31, or SEQ ID NO:35. In certain embodiments, the antibodies comprise one of the above-mentioned heavy chain variable domains and one of the above-mentioned light chain variable domains. In certain embodiments, the VEGFR2 antibodies or binding fragments thereof comprise one or more CDRs or one or more variable domains with an amino acid sequence at least 85% at least 90%, at least 95%, at least 97%, at least 98%, or at least 99%, identical to the CDR and variable domain sequences set forth in Table 1 or 2. In certain embodiments, antibodies of the invention have CDR amino acids identical to those disclosed herein and frameworks that are at least least 85%, at least 90%, of at least 95% identical.

"Identity" refers to the number or percentage of identical positions shared by two amino acid or nucleic acid sequences, taking into account the number of gaps, and the length of each gap, which need to be introduced for optimal alignment of the two sequences. "Substantially identical" means an amino acid sequence that which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein. Preferably, the amino acid sequence is at least 80%, more preferably at least 85%, and most preferably at least 90% similar to another amino acid sequence. Methods and computer programs for determining sequence similarity are publically available, including, but not limited to, the GCG program package (Devereux et al., Nucleic Acids Research 12:387, 1984), BLASTP, BLASTN, FASTA (Altschul et al., J. Mol. Biol. 215:403 (1990), and the ALIGN program (version 2.0). The well-known Smith Waterman algorithm may also be used to determine similarity. The BLAST program is publicly available from NCBI and other sources (BLAST Manual, Altschul, et al., NCBI NLM NIH, Bethesda, Md. 20894; BLAST 2.0 at www.ncbi.nlm.nih.gov/blast/). In comparing sequences, these methods account for various substitutions, deletions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

Antibodies of the invention also include those for which binding characteristics have been improved by direct mutation, methods of affinity maturation, phage display, or chain shuffling. Affinity and specificity may be modified or improved by mutating CDRs and screening for antigen binding sites having the desired characteristics. CDRs are mutated in a variety of ways. One way is to randomize individual residues or combinations of residues so that in a population of otherwise identical antigen binding sites, all twenty amino acids are found at particular positions. Alternatively, mutations are induced over a range of CDR residues by error prone PCR methods (see, e.g., Hawkins et al., J. Mol. Biol., 226:889-896 (1992)). For example, phage display vectors containing heavy and light chain variable region genes may be propagated in mutator strains of E. coli (see, e.g., Low et al., J. Mol. Biol., 250:359-368 (1996)). These methods of mutagenesis are illustrative of the many methods known to one of skill in the art.

To minimize the immunogenicity of antibodies that bind to VEGF receptors, the present invention provides antibodies which comprise human variable and constant domain sequences. The antibodies may be or may combine members of any immunoglobulin class, such as IgG, IgM, IgA, IgD, or IgE, and the subclasses thereof. The antibody class may be selected to optimize effector functions (e.g., complement dependent cytoxicity (CDC) and antibody dependent cellular cytoxicity (ADCC)) of natural antibodies.

Certain embodiments of the invention involve the use of VEGFR2-binding antibody fragments. An Fv is the smallest fragment that contains a complete heavy and light chain variable domain, including all six hypervariable loops (CDRs). Lacking constant domains, the variable domains are noncovalently associated. The heavy and light chains may be connected into a single polypeptide chain (a "single-chain Fv" or "scFv") using a linker that allows the $V_H$ and $V_L$ domains to associate to form an antigen binding site. In an embodiment of the invention, the linker is (Gly-Gly-Gly-Gly-Ser) 3. Since scFv fragments lack the constant domains of whole antibodies, they are considerably smaller than whole antibodies. scFv fragments are also free of normal heavy-chain constant domain interactions with other biological molecules which may be undesired in certain embodiments.

Fragments of an antibody containing $V_H$, $V_L$, and optionally $C_L$, $C_H1$, or other constant domains can also be used. Monovalent fragments of antibodies generated by papain digestion are referred to as Fab and lack the heavy chain hinge region. Fragments generated by pepsin digestion, referred to as F(ab')$_2$, retain the heavy chain hinge and are divalent. Such fragments may also be recombinantly produced. Many other useful antigen-binding antibody fragments are known in the art, and include, without limitation, diabodies, triabodies, single domain antibodies, and other monovalent and multivalent forms.

The invention further provides multivalent antigen-binding proteins, which can be in the form, without limitation, of antibodies, antigen-binding fragments thereof, and proteins comprising all or part of antigen-binding portions of antibodies. Multivalent antigen-binding proteins may be monospecific, bispecific, or multispecific. The term specificity refers to the number of different types of antigenic determinants to which a particular molecule can bind. If an immunoglobulin molecule binds to only one type of antigenic determinant, the immunoglobulin molecule is monospecific. If the immunoglobulin molecule binds to different types of antigenic determinants then the immunoglobulin molecule is multispecific.

For example, a bispecific multivalent single chain antibody allows for the recognition of two different types of epitopes. Both epitopes may be on the same antigen (e.g., VEGFR2). Alternatively, one epitope may be on one antigen (e.g., VEGFR2), and the second epitope on a different antigen.

In one embodiment, a multivalent single chain antibody includes a variable light-chain fragment linked to a variable heavy-chain fragment (similar to an scFv), which is further linked by another peptide linker to at least one other antigen binding domain. Typically, the peptide linker is composed of about fifteen amino acid residues. In a preferred embodiment, the number of $V_L$ and $V_H$ domains is equivalent. For example, a bivalent single chain antibody can be represented as follows: $V_L$-L$_1$-$V_H$-L$_2$-$V_L$-L$_3$-$V_H$ or $V_L$-L$_1$-$V_H$-L$_2$-$V_H$-L$_3$-$V_L$ or $V_H$-L$_1$-$V_L$-L$_2$-$V_H$-L$_3$-$V_L$ or $V_H$-L$_1$-$V_L$-L$_2$-$V_L$-L$_3$-$V_H$. Multivalent single chain antibodies which are trivalent or greater have one or more antibody fragments joined to a bivalent single chain antibody by additional peptide linkers. One example of a trivalent single chain antibody is: $V_L$-L$_1$-$V_H$-L$_2$-$V_L$-L$_1$-$V_H$-L$_2$-$V_L$-LI-$V_H$.

Two single chain antibodies can be combined to form a diabody, also known as bivalent dimer. Diabodies have two chains. Each chain of the diabody includes a $V_H$ domain connected to a $V_L$ domain by a short linker of about 5-10 amino acid residues, e.g. (Gly-Gly-Gly-Gly-Ser), (Gly-Gly-Gly-Gly-Ser) 2. Such linkers are short enough to prevent intrachain pairing between domains on the same chain, thus driving interchain pairing between complementary domains on different chains and recreate two antigen-binding sites. The diabody structure is rigid and compact, with antigen-binding sites are at opposite ends of the molecule. Diabodies may be monospecfic or bispecific.

Three single chain antibodies can be combined to form a triabody, also known as a trivalent trimers. In some embodiments, triabodies are constructed with the carboxy terminus of a $V_L$ or $V_H$ domain directly fused to the amino terminus of a $V_H$ or $V_L$ domain, i.e., without any linker sequence. The triabody has three Fv heads with the polypeptides arranged in a cyclic, head-to-tail fashion. A possible conformation of the triabody molecule is planar with the three binding sites located in a plane at an angle of 120 degrees from one another. Triabodies may be monospecific, bispecific or trispecific.

It is understood that the anti-VEGFR2 antibodies of the invention, where used in a mammal for the purpose of prophylaxis or treatment, will be administered in the form of a composition additionally comprising a pharmaceutically acceptable carrier. Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the antibodies.

In the methods of the present invention, a therapeutically effective amount of an antibody of the invention is administered to a mammal in need thereof. The term "administering" as used herein means delivering the antibodies of the present invention to a mammal by any method that may achieve the result sought. They may be administered, for example, intravenously or intramuscularly. Although human antibodies of the invention are particularly useful for administration to humans, they may be administered to other mammals as well. The term "mammal" as used herein is intended to include, but is not limited to, humans, laboratory animals, domestic pets and farm animals. "Therapeutically effective amount" means an amount of antibody of the present invention that, when administered to a mammal, is effective in producing the desired therapeutic effect, such as inhibiting kinase activity. For example, depending on the disease, for an antibody, this may require 0.1, 1.0, 3.0, 6.0, or 10.0 mg/Kg. For an IgG having a molecular mass of 150,000 g/mole (two binding sites), these doses correspond to approximately 18 nM, 180 nM, 540 nM, 1.08 μM, and 1.8 μM of binding sites for a 5 L blood volume.

Antibodies of the invention are useful for inhibiting tumor growth, angiogenesis associated with tumor growth, or other pathologic condition associated with angiogenesis. Tumors that can be treated include primary tumors, metastatic tumors, and refractory tumors. Refractory tumors include tumors that fail to respond or are resistant to treatment with chemotherapeutic agents alone, antibodies alone, radiation alone or combinations thereof. Refractory tumors also encompass tumors that appear to be inhibited by treatment with such agents, but recur up to five years, sometimes up to ten years or longer after treatment is discontinued. The antibodies are effective for treating vascularized tumors and tumor that are not vascularized, or not yet substantially vascularized.

Examples of solid tumors which may be accordingly treated include breast carcinoma, lung carcinoma, colorectal carcinoma, pancreatic carcinoma, glioma and lymphoma. Some examples of such tumors include epidermoid tumors, squamous tumors, such as head and neck tumors, colorectal tumors, prostate tumors, breast tumors, lung tumors, including small cell and non-small cell lung tumors, pancreatic tumors, thyroid tumors, ovarian tumors, and liver tumors. Other examples include Kaposi's sarcoma, CNS neoplasms, neuroblastomas, capillary hemangioblastomas, meningiomas and cerebral metastases, melanoma, gastrointestinal and renal carcinomas and sarcomas, rhabdomyosarcoma, glioblastoma, preferably glioblastoma multiforme, and leiomyosarcoma. Examples of vascularized skin cancers for which the antagonists of this invention are effective include squamous cell carcinoma, basal cell carcinoma and skin cancers that can be treated by suppressing the growth of malignant keratinocytes, such as human malignant keratinocytes.

Examples of non-solid tumors include leukemia, multiple myeloma and lymphoma. Some examples of leukemias include acute myelogenous leukemia (AML), chronic myelogenous leukemia (CML), acute lymphocytic leukemia (ALL), chronic lymphocytic leukemia (CLL), erythrocytic leukemia or monocytic leukemia. Some examples of lymphomas include Hodgkin's and non-Hodgkin's lymphoma.

Antibodies of the invention can also be used to treat or preventing pathologic conditions characterized by excessive angiogenesis, involving, for example, vascularization and/or inflammation, such as atherosclerosis, rheumatoid arthritis (RA), hemangiomas, angiofibromas, and psoriasis. Other non-limiting examples of non-neoplastic angiogenic disease are retinopathy of prematurity (retrolental fibroplastic), corneal graft rejection, insulin-dependent diabetes mellitus, multiple sclerosis, myasthenia gravis, Chron's disease, autoimmune nephritis, primary biliary cirrhosis, acute pancreatitis, allograph rejection, allergic inflammation, contact dermatitis and delayed hypersensitivity reactions, inflammatory bowel disease, septic shock, osteoporosis, osteoarthritis, cognition defects induced by neuronal inflammation, Osler-Weber syndrome, restinosis, and fungal, parasitic and viral infections, including cytomegaloviral infections.

Ocular diseases characterized by excessive angiogeneis include neovascular glaucoma, proliferative retinopathy including proliferative diabetic retinopathy, and macular degeneration The invention provides methods and compounds for treating ocular diseases and disorders. In one embodiment, the invention provides for treating age related macular degeneration (AMD), which occurs in "dry" and "wet" forms. The "wet" form of AMD causes vision loss due to abnormal blood vessel growth (neovascularization). Bleeding, leaking, and scarring from these retinal blood vessels eventually causes irreversible damage to the photoreceptors. The dry form results from atrophy of the retinal pigment epithelial layer, which causes vision loss through loss of photoreceptors (rods and cones) in the central part of the eye. In another embodiment, the invention provides a method of treating choroidal neovascularization (CNV). Choroidal neovascularization is a process in which new blood vessels grow in the choroid, through the Bruch membrane and invade the subretinal space, and is a symptom of, among other causes, age-related macular degeneration, myopia and ocular trauma. In another embodiment, the invention provides a method of treating diabetic macular edema (DME). In another embodiment, the invention provides a method of treating macular edema that is secondary to branch retinal vein occlusion (BRVO) or central retinal vein occlusion (CRVO). Other diseases treatable according to the invention include, without limitation, iris neovascularization, uveitis, neovascular glaucoma, and retinitis of prematurity (ROP). The method of treatment can be prophylactic, such as to stave off corneal neovascularization after corneal transplant, or to modulate the wound healing process in trabeculectomy surgery.

Antibodies and antigen binding fragments of the invention can be advantageously administered with second agents to patients in need thereof. For example, in some embodiments, a VEGFR-2 antibody of the invention is administered to a subject with an anti-neoplastic agent. In some embodiments, a VEGFR-2 antibody is administered to a subject with a second angiogenesis inhibitor. In some embodiments, a VEGFR-2 antibody of the invention is administered with an anti-inflammatory agent or an immunosuppressant.

Antineoplastic agents include cytotoxic chemotherapeutic agents, targeted small molecules and biological molecules, and radiation. Non-limiting examples of chemotherapeutic agents include cisplatin, dacarbazine (DTIC), dactinomycin, irinotecan, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin, paclitaxel (taxol), docetaxel (taxotere), aldesleukin, asparaginase, busulfan, carboplatin, cladribine, dacarbazine, floxuridine, fludarabine, hydroxyurea, ifosfamide, interferon alpha, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil, taxol and combinations thereof.

Targeted small molecules and biological molecules include, without limitation, inhibitors of components of signal transduction pathways, such as modulators of tyrosine kinases and inhibitors of receptor tyrosine kinases, and agents that bind to tumor-specfic antigens. Non-limiting examples of growth factor receptors involved in tumorigenesis are the receptors for platelet-derived growth factor (PDGFR), insulin-like growth factor (IGFR), nerve growth factor (NGFR), and fibroblast growth factor (FGFR), and receptors of the epidermal growth factor receptor family, including EGFR (erbB1), HER2 (erbB2), erbB3, and erbB4.

EGFR antagonists incluce antibodies that bind to EGFR or to an EGFR ligand, and inhibits ligand binding and/or receptor activation. For example, the agent can block formation of receptor dimers or heterodimer with other EGFR family menbers. Ligands for EGFR include, for example, EGF, TGF-$\alpha$ amphiregulin, heparin-binding EGF (HB-EGF) and betarecullulin. An EGFR antagonist can bind externally to the extracellular portion of EGFR, which may or may not inhibit binding of the ligand, or internally to the tyrosine kinase domain. EGFR antagonists further include agents that inhibit EGFR-dependent signal transduction, for example, by inhibiting the function of a component of the EGFR signal transduction pathway. Examples of EGFR antagonists that bind EGFR include, without limitation, biological molecules, such as antibodies (and functional equivalents thereof) specific for EGFR, and small molecules, such as synthetic kinase inhibitors that act directly on the cytoplasmic domain of EGFR.

Small molecule and biological inhibitors include inhibitors of epidermal growth factor receptor (EGFR), including gefitinib, erlotinib, and cetuximab, inhibitors of HER2 (e.g., trastuzumab, trastuzumab emtansine (trastuzumab-DM1; T-DM1) and pertuzumab), anti-VEGF antibodies and fragments (e.g., bevacizumab), antibodies that inhibit CD20 (e.g., rituximab, ibritumomab), anti-VEGFR antibodies (e.g., ramucirumab (IMC-1121B), IMC-1C11, and CDP791), anti-PDGFR antibodies, and imatinib. Small molecule kinase inhibitors can be specific for a particular tyrosine kinase or be inhibitors of two or more kinases. For example, the compound N-(3,4-dichloro-2-fluorophenyl)-7-({[(3aR,6aS)-2-methyloctahydrocyclopenta[c]pyrrol-5-yl]methyl}oxy)-6-(methyloxy) quinazolin-4-amine (also known as XL647, EXEL-7647 and KD-019) is an in vitro inhibitor of several receptor tyrosine kinases (RTKs), including EGFR, EphB4, KDR (VEGFR), Flt4 (VEGFR3) and ErbB2, and is also an inhibitor of the SRC kinase, which is involved in pathways that result in nonresponsiveness of tumors to certain TKIs. In an embodiment of the invention, treatment of a subject in need comprises administration of a rho-kinase inhibitor of Formula I and administration of KD-019.

Dasatinib (BMS-354825; Bristol-Myers Squibb, New York) is another orally bioavailable, ATP-site competitive Src inhibitor. Dasatanib also targets Bcr-Abl (FDA-approved for use in patients with chronic myelogenous leukemia (CML) or Philadelphia chromosome positive (Ph+) acute lymphoblastic leukemia (ALL)) as well as c-Kit, PDGFR, c-FMS, EphA2, and SFKs. Two other oral tyrosine kinase inhibitor of Src and Bcr-Abl are bosutinib (SKI-606) and saracatinib (AZD0530).

While VEGFR2 mediates the majority of the downstream effects of VEGF in angiogenesis, it can be advantageous to administer a second angiogenesis inhibitor. Anti-VEGFR-2 antibodies of the invention may be administered with antibodies that neutralize other receptors involved in tumor growth or angiogenesis.

Non-limiting examples of VEGF-binding agents include VEGF antibodies and VEGF traps (i.e., ligand binding domains of VEGF receptors. Two examples of antibodies (including VEGF-binding antibody fragments) are bevacizumab (Avastin), an antibody which binds to VEGF-A, and ranibizumab (Lucentis), an Fab derived from bevacizumab. In general, a VEGF trap is a protein that comprises VEGF binding domains of one or more VEGF receptor protein. VEGF-traps include, without limitation, soluble VEGFR-1, soluble neuropilin 1 (NRP1), soluble VEGFR-3 (which binds VEGF-C and VEGF-D), and aflibercept (Zaltrap; Eylea; VEGF Trap RIR2), comprised of segments of the extracellular domains of human vascular endothelial growth factor receptors VEGFR1 and VEGFR2 fused to the constant region (Fc) of human IgG1. Conbercept (KH902) is a fusion protein which contains the extracellular domain 2 of VEGFR-1 (Flt-1) and extracellular domain 3, 4 of VEGFR-2 (KDR) fused to the Fc portion of human IgG1. Several VEGF traps containing KDR and FLT-1 Ig-like domains in various combinations are disclosed in U.S. Pat. No. 8,216,575. DARPins (an acronym for designed ankyrin repeat proteins) are genetically engineered antibody mimetic proteins typically exhibiting highly specific and high-affinity target protein binding. DARPin® MP0112 is a vascular endothelial growth factor (VEGF) inhibitor and has entered clinical trials for the treatment of wet macular degeneration and diabetic macular edema.

According to the invention, VEGF expression can be targeted. For example, VEGF inhibitor PTC299 targets VEGF post-transcriptionally by selectively binding the 5'- and 3'-untranslated regions (UTR) of VEGF messenger RNA (mRNA), thereby preventing translation of VEGF. Pegaptanib (Macugen) is an RNA aptamer directed against VEGF-165.

Placental growth factor (PIGF) has been implicated in pathological angiogenesis. PIGF is structurally related to VEGF and is also a ligand for VEGFR-1. Consequently, VEGF traps comprising the extracellular domain of VEGFR1 (see above) are useful for targeting PIGF. Anti-angiogenic agents further include those that bind to the VEGFR-1/Flt-1 receptor. In certain embodiments, the antigen-binding proteins that bind to the extracellular domain of VEGFR-1 block binding by one or both of its ligands, VEGF and PIGF, and/or neutralize VEGF-induced or PIGF-induced activation of VEGFR-1.

PDGF is composed of four polypeptide chains that form homodimers PDGF-AA, BB, CC, and DD as well as the heterodimer PDGF-AB. The PDGF receptors (PDGFR)-α and -β mediate PDGF functions. Specifically, PDGFRα binds to PDGF-AA, -BB, -AB, and -CC, whereas PDGFRβ interacts with -BB and -DD. Non-limiting examples of PDGF-binding agents include anti-PDGF antibodies and PDGF traps. Agents that target PDGF include Fovista™ (E10030, Ophthotech), a pegylated aptamer targeting PDGF-B, and AX102 (Sennino et al., 2007, Cancer Res. 75 (15): 7359-67), a DNA oligonucleotide aptamer that binds PDGF-B.

In certain embodiments of the present invention, an antibody or an antigen binding fragment thereof is administered to a subject together with an effective amount of a PDGFRβ antibody Agents that target PDGF receptors include ramucirumab (IMC-3G3, human IgG$_1$) an anti-PDGFRα antibody, crenolanib (CP-868596), a selective inihibitor of PDGFRα (IC$_{50}$=0.9 nM) and PDGFRβ (IC$_{50}$=1.8 nM), and nilotinib (Tasigna®), an inhibitor of PDGFRα and PDGFRβ and other tyrosine kinases.

Angiogenesis inhibitors include intracellular agents that block signal transduction mediated by, for example, VEGF, PDGF, ligands of VEGF or PDGF receptors, or complement. Intracellular agents that inhibit angiogenesis inhibitors include the following, without limitation. Sunitinib (Sutent; SU11248) is a panspecific small-molecule inhibitor of VEGFR1-VEGFR3, PDGFRα and PDGFRβ, stem cell factor receptor (cKIT), Flt-3, and colony-stimulating factor-1 receptor (CSF-1R). Axitinib (AG013736; Inlyta) is another small molecule tyrosine kinase inhibitor that inhibits VEGFR-1-VEGFR-3, PDGFR, and cKIT. Cediranib (AZD2171) is an inhibitor of VEGFR-1-VEGFR-3, PDGFRβ, and cKIT. Sorafenib (Nexavar) is another small molecular inhibitor of several tyrosine protein kinases, including VEGFR, PDGFR, and Raf kinases. Pazopanib (Votrient; GW786034) inhibits VEGFR-1, -2 and -3, cKIT and PDGFR. Foretinib (GSK1363089; XL880) inhibits VEGFR2 and MET, as does cabozantinib (Cometriq; XL184). Ponatinib (Iclusig; AP24534) inhibits VEGFR, PDGFR and c kit. Tivozanib (AV-951) inhibits VEGFR-1, VEGFR-2 and VEGFR-3 at picomolar concentrations. CP-547632 is as a potent inhibitor of the VEGFR-2 and basic fibroblast growth factor (FGF) kinases. E-3810 ((6-(7-((1-aminocyclopropyl) methoxy)-6-methoxyquinolin-4-yloxy)-N-methyl-1-naphthamide) inhibits VEGFR-1, -2, and -3 and FGFR-1 and -2 kinases in the nanomolar range. Brivanib (BMS-582664) is a VEGFR-2 inhibitor that also inhibits FGF receptor signaling. CT-322 (Adnectin) is a small protein based on a human fibronectin domain and binds to and inhibits activation of VEGFR2. Vandetanib (Caprelas; Zactima; ZD6474) is an inhibitor of VEGFR2, EGFR, and RET tyrosine kinases. X-82 (Xcovery) is a small molecule indolinone inhibitor of signaling through the growth factor receptors VEGFR and PDGFR.

In certain embodiments, anti-VEGFR antibodies of the invention are coadministered with matrix metalloproteinase inhibitors. Matrix metalloproteases (MMPs), such as MMP-14, MMP-16, and MMP-24, cleave components of the extracellular matrix (ECM) and basement membranes, thereby allowing cancer cells to penetrate and infiltrate the subjacent stromal matrix. Additionally, a number of growth-factor receptors, cell adhesion molecules, chemokines, cyto-kines, apoptotic ligands, and angiogenic factors are sub-strates of MMPs. Hence, MMP activity may cause activation of growth factors, suppression of tumor cell apoptosis, destruction of chemokine gradients developed by host immune response, or release of angiogenic factors. MMPs may facilitate tumor growth by promoting the release of cell proliferation factors such as insulin-like growth factors which are bound to specific binding proteins (IGFBPs) (Manes et al., 1997 J. Biol. Chem. 272:25706-25712).

Collagenases, including MMP-2, have been found at elevated levels in melanoma and in cancers of the colon, breast, lung, prostate, and bladder. Usually, these elevated levels correlate with higher tumor grade and invasiveness. MMP-2 levels are significantly elevated in the serum of patients with metastatic lung cancer, and in those patients with high levels, response to chemotherapy is diminished. MMP-14, which cleaves proMMP-2 to release active MMP-2, is elevated in numerous cancers and can contribute to the growth of tumors, tumor embolism, and the mobility, inva-siveness and metastasis of cancer (e.g., CNS tumors (e.g., gliomas), head and neck cancer, oral cavity cancer, laryngeal cancer, chondrosarcoma, breast cancer). MMP-16 and MMP-24 are also elevated in numerous cancers and can contribute to both the growth of tumors and the invasiveness and metastasis of cancer (e.g., breast cancer, laryngeal cancer, ovarian cancer, testicular carcinoma, melanoma, brain tumors (e.g., astrocytomas, glioblastomas, gliomas).

In certain embodiments, anti-VEGFR antibodies of the invention are coadministered with MMP-14 antagonists, including but not limited to anti-MMP-14 antibodies dis-closed in U.S. Pat. Nos. 7,745,587 and 8,106,168. In one embodiment, the antibody is human monoclonal antibody DX-2400 (Dyax Corp). Coadministration with such an anti-body is suitable for treatment of human carcinomas, includ-ing but not limited to, uterine cervix, stomach, lung, breast, colon, head and neck, malignant brain tumors, and mela-noma.

In another embodiment, a VEGFR2 antibody of the invention can be administered in combination with one or more suitable adjuvants, such as, for example, cytokines (IL-10 and IL-13, for example) or other immune stimulators. It should be appreciated, however, that administration of only an anti-KDR antibody is sufficient to prevent, inhibit, or reduce the progression of the tumor in a therapeutically effective manner.

Anti-inflammatoirend immunosuppressants include ste-roid drugs such as glucocorticoids (e.g., dexamethasone), FK506 (tacrolimus), ciclosporin, fingolimod, interferon, such as IFNβ or IFNγ, a tumor necrosis factor-alpha (TNF-α) binding protein such as infliximab (Remicade), etaner-cept (Enbrel), or adalimumab (Humira), and mycophenolic acid.

Certain embodiments comprise administering an antibody of the invention and a second agent as follows: docetaxel for solid tumors, including breast cancer and urinary tract and renal cancers, paclitaxel (solid tumors, gastric adenocarci-noma), FOLFRI (i.e, irinotican, folinic acid, 5-Florouracil) for colorectal cancer, capecitabine (breast cancer), FOLFOX (i.e., oxaliplatin, leucovorin, 5-Fluorouracil) (gastric, esophageal, gastroesophageal cancers), eribulin (breast can-cer), FOLFIRI (i.e., irinotecan, levofolinate, 5-Fluorouracil) (colorectal carcinoma), carboplatin (NSCLC), mitoxantrone and prednisone (prostate cancer), OFF (oxaliplatin folinic acid, 5-Florouracil) (colorectal cancer), irinotican and cetux-imab (colorectal cancer), and dacarbazine (malignant mel-anona).

The antibodies and antigen binding fragments of the invention can be conjugated to an agent, e.g., a cytotoxic drug, cytotoxin enzyme, or radioisotope. This method includes administering the binding protein alone or attached to an agent (e.g., a cytotoxic drug), to a subject requiring such treatment. For example, VEGFR2 antibodies or frag-ments thereof may be used to deliver nanoparticles contain-ing agents, such as toxins, to VEGFR2 associated cells or tissues, e.g., tumors.

The VEGFR2 binding proteins can be used directly in vivo to eliminate antigen-expressing cells via natural complement-dependent cytotoxicity (CDC) or antibody dependent cellular cytotoxicity (ADCC). The binding pro-teins described herein can include complement binding effector domain, such as the Fc portions from IgG1, -2, or -3 or corresponding portions of IgM which bind complement.

When a VEGFR-2 antibody of the invention is adminis-tered with a second agent, the first and second agents can be adminstered sequentially or simultaneously. Each agent can be administered in single or multiple doses, and the doses can be administered on any schedule, including, without limitation, twice daily, daily, weekly, every two weeks, and monthly.

The invention also includes adjunctive administration. Adjunctive administration means that a second agent is administered to a patient in addition to a first agent that is already being administered to treat a disease or disease symptom. In some embodiments, adjunctive administration includes administering a second agent to a patient in which administration of the first agent did not treat, or did not sufficiently treat, the disease or disease symptom. In other embodiments, adjunctive administration includes adminis-tration of the second agent to a patient whose disease has been effectively treated by administration of the first agent.

In one embodiment of the invention, an antibody or an antigen binding fragment thereof is administered by injec-tion, a small molecule administered orally. In one such embodiment, the antibody is administered weekly or once or twice per month and the small molecule is administered daily.

In an embodiment of the invention, an antibody or an antigen binding fragment thereof is administered by injec-tion, and a ROCK2 inhibitor is administered orally. In a preferred embodiment, the agents are administered once daily. According to the invention, when a ROCK inhibitor, or a VEGFR2 antibody are administered to a subject to treat an ocular disease, a TGF-β antagonist can be administered to the subject to reduce or prevent scarring. For example, in an embodiment of the invention, when a ROCK inhibitor is administered to treat an ocular disorder, a TGF-β antagonist is also administered. In another embodiment, when a VEGF antagonist is administered to a subject to treat an ocular disorder, a TGF-β antagonist is also administered. In another embodiment of the invention, when a ROCK inhibitor and a VEGF antagonist are administered to a subject to treat an ocular disorder, a TGF-β antagonist is also administered. In ocular diseases involving neovascularization, leakage of new blood vessels is followed by scar formation (e.g., discaform scar). The invention includes administration of a TGF-β antagonist as well as a VEGF antagonist and a ROCK2 inhibitor to a subject to treat neovascularization in ocular disease.

Useful TGF-β antagonists include, without imitation, the following: (i) anti-TGF-β antibodies and antigen binding fragments thereof, such as pan-TGF-β antibody GC-1008 (Genzyme), anti-TGF-$\beta_1$ antibody metelimumab (CAT-192) (Cambridge Antibody Technology), and antigen binding fragments of those antibodies, (ii) soluble TGF-β receptors or ligand binding fragments thereof, such as P144, a synthetic peptide encompassing amino acids 730-743 from the membraneproximal ligand-binding domain of TGF-β type III receptor (Esparza-López et al., 2001, J. Biol. Chem. 276 (18): 14588-96), and a type II TGF-β receptor-Fc (IgG$_1$) fusion (Smith, J. et al., 1999, Circulation Res. 84:1212-22), (iii) peptides that bind to TGF-β receptors that block one or more isoforms of TGF-β, such as the 25 amino acid peptides from TGF-$\beta_1$, TGF-$\beta_2$, and TGF-$\beta_3$ disclosed by Huang et al., 1997, J. Biol. Chem. 272:27155-59, that bind to TGF-β receptors, and (iv) antisense agents that inhibit TGF-β synthesis, such as trabedersen (Antisense Pharma GmbH), an oligonucleotide that inhibits the synthesis of TGF-β2. Additional antagonists are disclosed in WO2006/052568, WO 02/094833, WO 04/048382, WO 04/048381, WO 04/050659, WO 04/021989, WO 04/026871, and WO 04/026307.

In certain embodiments of the present invention, an antibody or an antigen binding fragment thereof is administered to a subject together with an effective amount of a PD-L1 antibody (see U.S. 61/927,907 and PCT/US15/11657, which are incorporated herein by reference in their entirety).

In certain embodiments, a dose of a compound or a composition is administered to a subject every day, every other day, every couple of days, every third day, once a week, twice a week, three times a week, or once every two weeks. In other embodiments, two, three or four doses of a compound or a composition is administered to a subject every day, every couple of days, every third day, once a week or once every two weeks. In some embodiments, a dose(s) of a compound or a composition is administered for 2 days, 3 days, 5 days, 7 days, 14 days, or 21 days. In certain embodiments, a dose of a compound or a composition is administered for 1 month, 1.5 months, 2 months, 2.5 months, 3 months, 4 months, 5 months, 6 months or more.

Methods of administration include but are not limited to parenteral, intradermal, intravitrial, intramuscular, intraperitoneal, intravenous, subcutaneous, intranasal, epidural, oral, sublingual, intranasal, intracerebral, intravaginal, transdermal, transmucosal, rectally, by inhalation, or topically, particularly to the ears, nose, eyes, or skin. The mode of administration is left to the discretion of the practitioner. In most instances, administration will result in the release of a compound into the bloodstream. For treatment of ocular disease, intravitrial administration of biological agents is preferred.

In specific embodiments, it may be desirable to administer a compound locally. This may be achieved, for example, and not by way of limitation, by local infusion, topical application, by injection, by means of a catheter, or by means of an implant, said implant being of a porous, non-porous, or gelatinous material, including membranes, such as sialastic membranes, or fibers. In such instances, administration may selectively target a local tissue without substantial release of a compound into the bloodstream.

Pulmonary administration can also be employed, e.g., by use of an inhaler or nebulizer, and formulation with an aerosolizing agent, or via perfusion in a fluorocarbon or synthetic pulmonary surfactant. In certain embodiments, a compound is formulated as a suppository, with traditional binders and vehicles such as triglycerides.

In another embodiment, a compound is delivered in a vesicle, in particular a liposome (See Langer, 1990, Science 249:1527-1533; Treat et al., in Liposomes in the Therapy of Infectious Disease and Bacterial infection, Lopez-Berestein and Fidler (eds.), Liss, New York, pp. 353-365 (1989); Lopez Berestein, ibid., pp. 317-327; see generally ibid.).

In another embodiment, a compound is delivered in a controlled release system (See, e.g., Goodson, in Medical Applications of Controlled Release, supra, vol. 2, pp. 115-138 (1984)). Examples of controlled-release systems are discussed in the review by Langer, 1990, Science 249:1527-1533 may be used. In one embodiment, a pump may be used (See Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (See Medical Applications of Controlled Release, Langer and Wise (eds.), CRC Pres., Boca Raton, Florida (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; See also Levy et al., 1985, Science 228:190; During et al., 1989, Ann. Neurol. 25:351; Howard et al., 1989, J. Neurosurg. 71:105).

The above-described administration schedules are provided for illustrative purposes only and should not be considered limiting. A person of ordinary skill in the art will readily understand that all doses are within the scope of the invention.

It is to be understood and expected that variations in the principles of invention herein disclosed may be made by one skilled in the art and it is intended that such modifications are to be included within the scope of the present invention.

Throughout this application, various publications are referenced. These publications are hereby incorporated into this application by reference in their entireties to more fully describe the state of the art to which this invention pertains. The following examples further illustrate the invention, but should not be construed to limit the scope of the invention in any way.

EXAMPLES

Example 1

Identification of Antibodies that Bind to VEGFR Domains 2 and 3 and Block Ligand Binding.

Figure 3:
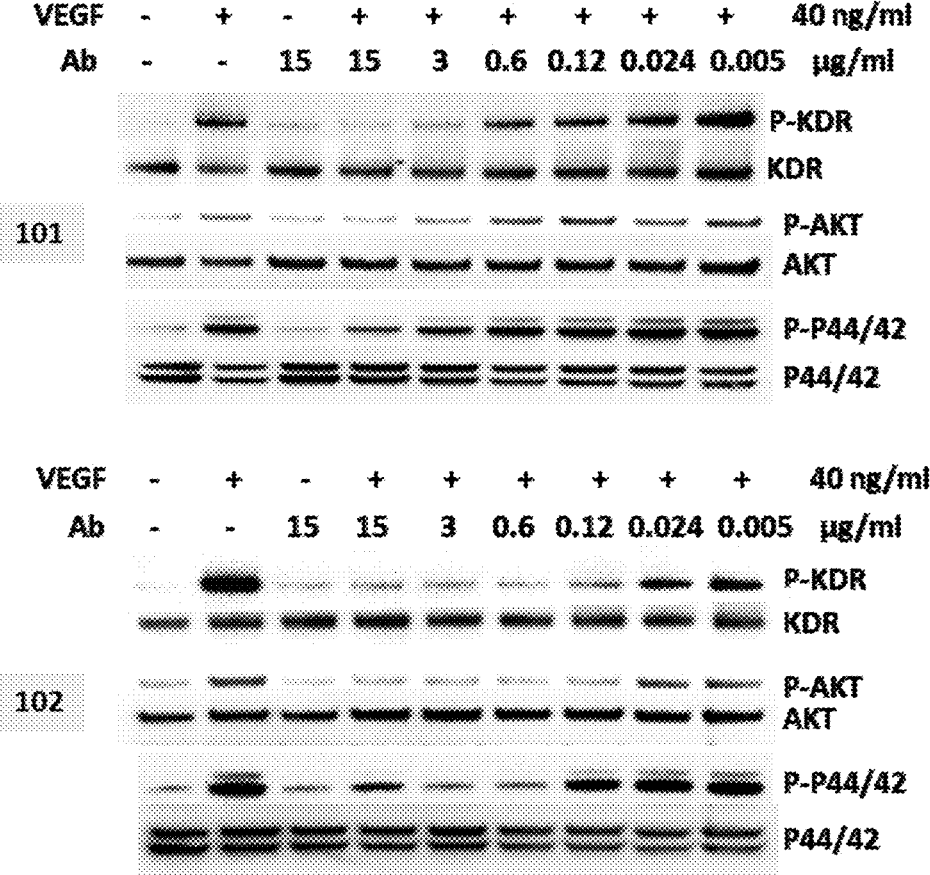
FIG. 3 shows Mabs 101 and 102 of the invention inhibit VEGFA-stimulated phosphorylation of VEGFR2, AKT, and MAPK in porcine aortic endothelial (PAE) cells overexpressing KDR (human VEGFR2).

Two antibodies that bind to and neutralize human VEGFR2, identified in Table 1, were isolated from human Fab phage display libraries. The antibodies block binding of the ligand VEGFA to hVEGFR2 (FIG. 2). The antibodies also bind to porcine aortic endothelial (PAE) cells expressing KDR, and inhibit VEGFA-stimulated phosphorylation of VEGFR2, AKT, and MAPK. (FIG. 3). Table 1 indicates amino acid sequences of the CDRs and variable domains of the antibodies. The K$_d$s of Mab 101 and Mab 102 are about 6.6 mM and 1.7 nM, respectively.

The heavy chain of Mab 101 was reshuffled with κ light chain genes (κ-library) and λ light chain genes (λ-library).

20 unique λ light chain variants were found by panning the λ-library against both human VEGFR2 and mouse VEGFR2. 22 unique κ light chain variants were found by panning the κ-library against both human VEGFR2 and mouse VEGFR2. Table 2 indicates amino acid sequences of the CDRs and variable domains of the light chains. The $K_d$s of Mabs 105, 106, and 107 were increased about 10 fold (0.24 nM, 0.22 nM, and 0.12 nM, respectively) (Table 3). These antibodies, and antibody Mab 101 from which they are derived, bind to domains 2 and 3 of VEGFR and to constructs containing those domains.

TABLE 3

| Antibody Binding Data | | | |
| --- | --- | --- | --- |
| Antibody | ka $10^4 M^{-1} s^{-1}$ | kd $10^{-4} s^{-1}$ | KD nM |
| 107 | 55.8 | 0.934 | 0.167 |
| 109 | 30.6 | 3.80 | 1.24 |
| 104 | 79.2 | 1.13 | 0.165 |
| 110 | 44.9 | 3.10 | 0.69 |
| 108 | 71.9 | 1.75 | 0.244 |
| 105 | 24.3 | 0.591 | 0.243 |
| 101 | 29.8 | 5.93 | 1.81 |

Figure 5A:
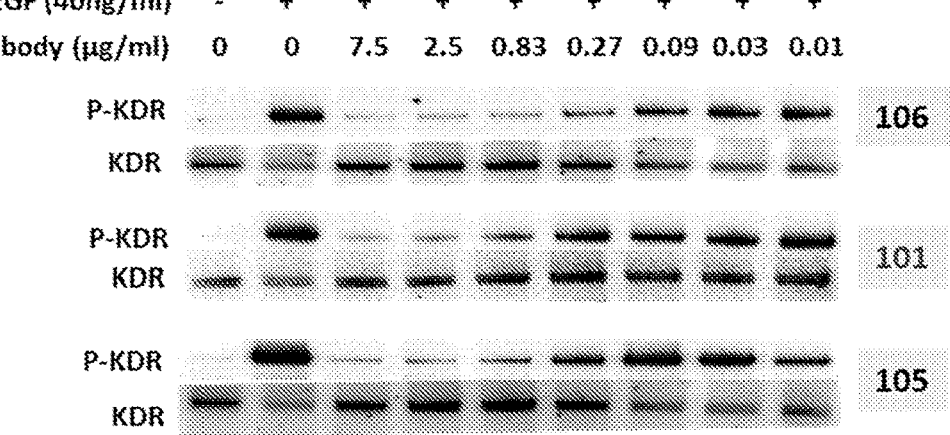
FIGS. 5A-5C show Mabs 105 and 106 of the invention inhibit VEGFA-stimulated phosphorylation of VEGFR2, AKT, and MAPK in porcine aortic endothelial (PAE) cells overexpressing KDR (human VEGFR2).
Figure 5B:
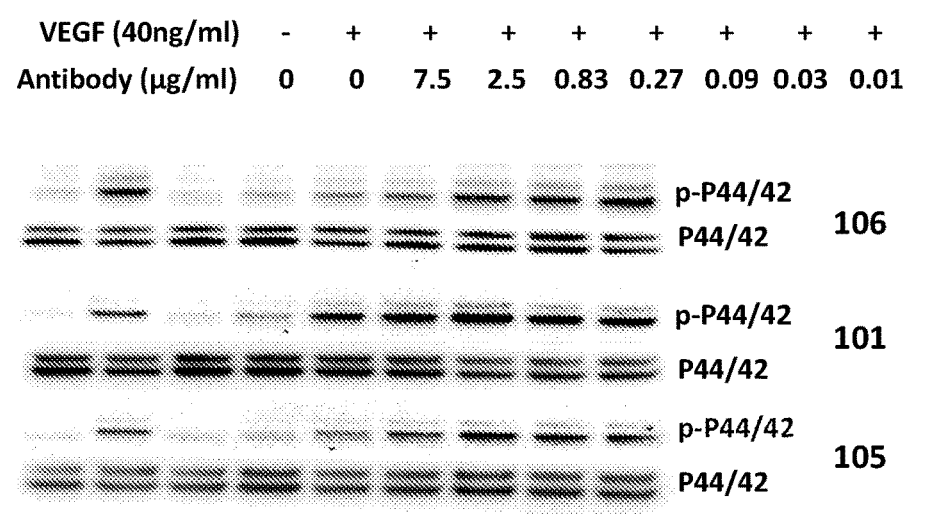
Figure 5C:
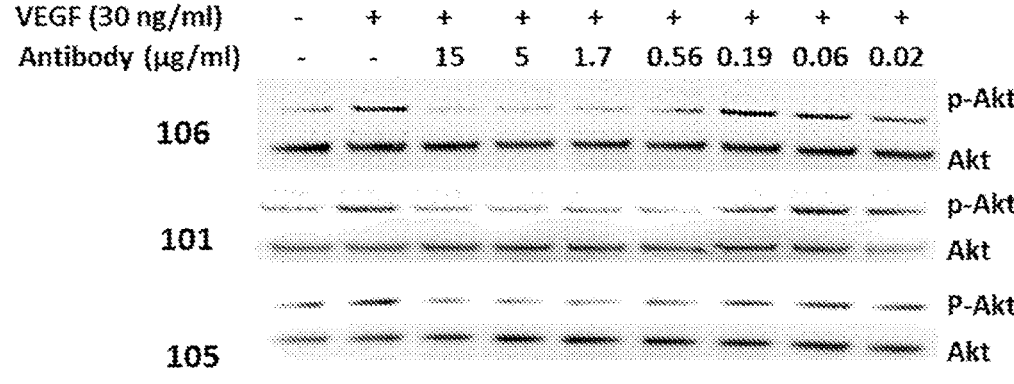

Like the parent antibody, these antibodies bind to VEGFR2 and block binding of VEGFA to VEGFR2 (FIG. 4), and inhibit VEGFA-stimulated phosphorylation of VEGFR2, AKT, and MAPK (FIGS. 5A-C).

Several of the antibodies, including Mabs 138, 139, 140, and 146, also cross react with mouse VEGFR2.

TABLE 4

| Cross Reactivity | | | | | | |
| --- | --- | --- | --- | --- | --- | --- |
| | hVEGFR2 | | | mVEGFR2 | | |
| Anti-body | ka $10^4 M^{-1} s^{-1}$ | kd $10^{-4} s^{-1}$ | KD nM | ka $10^4 M^{-1} s^{-1}$ | kd $10^{-4} s^{-1}$ | KD nM |
| 138 | 19.7 | 1.42 | 0.72 | 23.4 | 5.90 | 2.55 |
| 139 | 14.6 | 1.75 | 1.20 | 13.0 | 3.17 | 2.44 |
| 106 | 35.6 | 0.512 | 0.144 | | | |

Mabs 138, 139, and 140 inhibited VEGFA-stimulated phosphorylation of VEFGR2 and downstream signal transduction molecules, including MAPK.

Example 2

Inhibition of Tumor Growth In Vivo 6 to 8-week-old sex-matched (female) NOD-SCID mice are irradiated with 3.5 Gy from a $^{137}$Cs gamma-ray source at a dose rate of about 0.9 Gy/min and intravenously inoculated with $2 \times 10^7$ HL60 cells. Three days after tumor inoculation, groups of mice are treated twice weekly with various doses of Mab 106 and recorded for time of survival.

All untreated mice died within about two weeks. Even with the high tumor load, the survival time for mice treatment with 10 mg/kg Mab 106 is extended to as much as 28 days.

Example 3

Treatment of Colon Cancer in a Human Patient

Human subjects diagnosed with colon cancer are divided into treatment groups and given the standard chemotherapeutic regimen. Two patient groups are treated weekly with 5 mg/kg/week or 15 mg/kg/week for 4 months. A control group is given only the standard chemotherapeutic regimen. Tumor burden is assessed periodically by magnetic resonance imaging (MRI). Compared to the control group, it is expected that the patients who have received weekly antibody treatments show significant reductions in tumor growth or tumor size, increased delay to progression or prolonged survival compared to patients that do not receive the antibody treatment.

Mab 138 (Table 2), containing the heavy chain of Mab 101 (SEQ ID NO. 4; see FIG. 6A), was selected for affinity maturation. Mutations were introduced into CDR3 of the light chan and CDR1, CDR2, and CDR3 of the heavy chain. The resulting library was panned on human and murine VEGFR2. Table 5 indicates amino acid sequences of the heavy and light chain CDRs and variable domains of five of the resulting antibodies. FIG. 6 shows a comparison of the sequences to the Mab 138 heavy chain (SEQ ID NO. 4) and kappa light chain (i.e. SEQ ID NO:160).

TABLE 5

| Antibody Amino Acid Sequences by SEQ ID NO | | | | | | | | |
| --- | --- | --- | --- | --- | --- | --- | --- | --- |
| Mab # | CDR-H1 | CDR-H2 | CDR-H3 | $V_H$ domain | CDR-L1 | CDR-L2 | CDR-L3 | $V_L$ domain |
| 147 (B1C4_A7) | 197 | 198 | 199 | 200 | 201 | 202 | 203 | 204 |
| 148 (B1C4_H9) | 205 | 206 | 207 | 208 | 209 | 210 | 211 | 212 |
| 149 B1C4_E5) | 213 | 214 | 215 | 216 | 217 | 218 | 219 | 220 |
| 150 (B1C4_A6) | 221 | 222 | 223 | 224 | 225 | 226 | 227 | 228 |
| 151 (B1C4_G3) | 229 | 230 | 231 | 232 | 233 | 234 | 235 | 236 |

The binding constants of Mab 147 and Mab 149 as well as the parent Mab 138 for human, murine, and rat VEGFR2 were determined by Biacore analysis (Table 6).

TABLE 6

| Biacore Analysis of Binding to Human, Murine, and Rat VEGFR2 | | | | |
| --- | --- | --- | --- | --- |
| Mab | antigen | $k_a$ | $k_d$ | $K_D$ |
| 138 | rat | 4.30E+04 | 1.34E−03 | 3.12E−08 |
| | murine | 2.86E+04 | 2.33E−03 | 8.17E−08 |
| | human | 8.98E+04 | 6.00E−04 | 6.68E−09 |
| 147 | rat | 6.45E+04 | 8.99E−04 | 1.39E−08 |
| | murine | 4.38E+04 | 1.28E−03 | 2.94E−08 |
| | human | 1.13E+05 | 2.82E−04 | 2.51E−09 |
| 149 | rat | 3.32E+04 | 1.43E−03 | 4.31E−08 |
| | murine | 2.29E+04 | 1.81E−03 | 7.92E−08 |
| | human | 8.62E+04 | 6.59E−04 | 7.65E−09 |

Figures 7A, 7B:
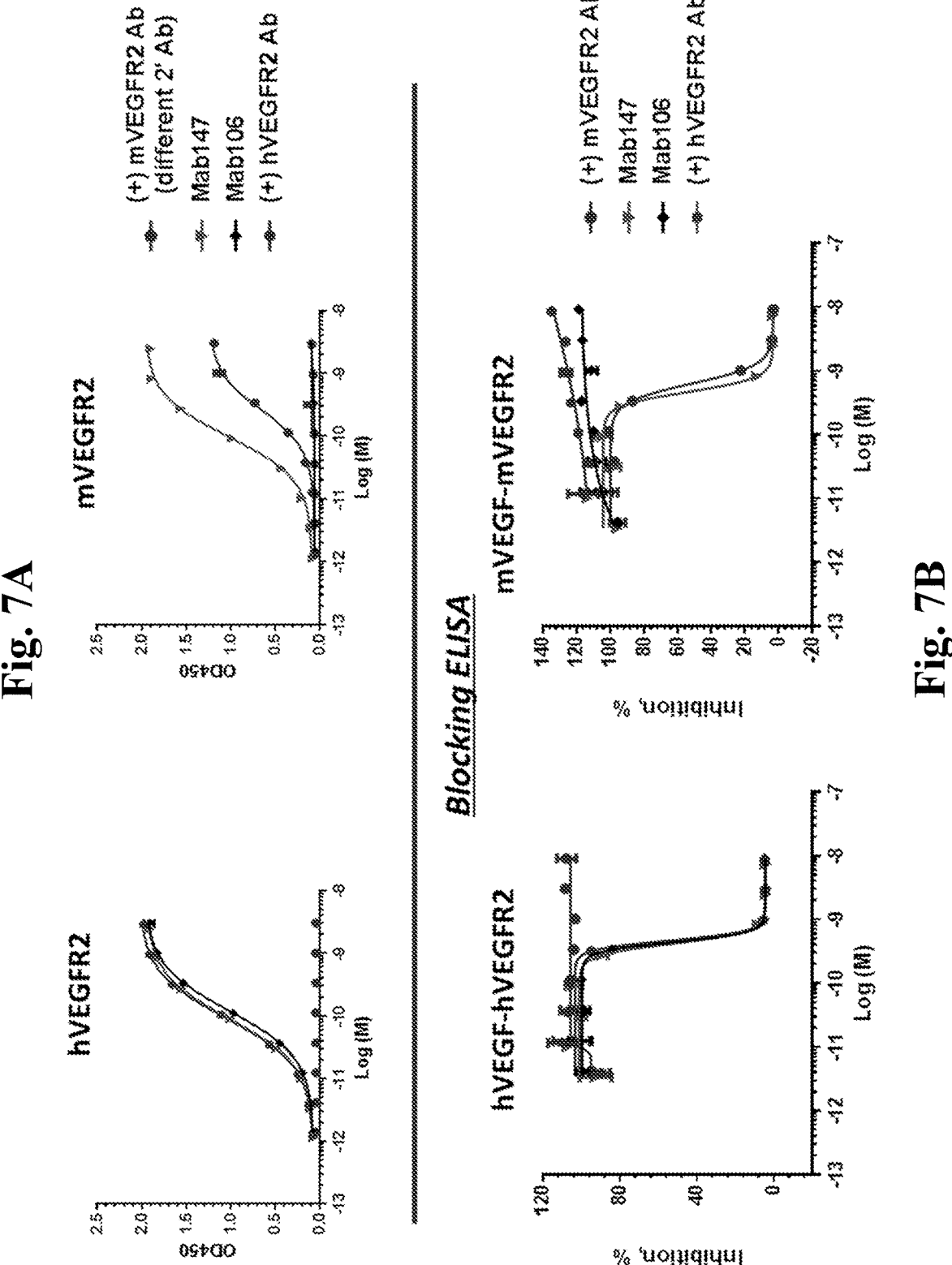
FIG. 7A depicts binding of antibodies of the invention to soluble human and murine VEGFR2 compared to DC101 (a murine monoclonal Ab that binds to murine VEGFR2) and a control antibody that binds only to human VEGFR2. Mab 147 binds to both human and murine VEGFR2. Mab 106 binds to human VEGFR2 but not murine VEGFR2.
FIG. 7B depicts data from ligand blocking experiments. Mab 147 blocks the binding of human VEGF with human VEGFR2 and the binding of murine VEGF with murine VEGFR2.

Mab 147 was examined by ELISA for its receptor binding and ligand blocking properties. Mab 147 binds to both soluble hVEGFR2 and soluble mVEGFR2 with similar affinity (FIG. 7A). Mab 147 blocks ligand binding to hVEGFR2 similar to a hVEGFR specific control antibody and also blocks ligangd binding to m VEGFR2 similar to a m VEGFR2-specific control antibody (FIG. 7B).

Binding of Mab 147 to hVEGFR2 and m VEGFR2 expressed on cell membranes was also confirmed. FIG. 8A shows binding to hVEGR2 expressed by human umbilical vein entothelial cells (HUVEC) as well as procine aortic endothelial (PAE) cells overexpressing KDR (i.e., human VEGFR2). Mab 147 also bound to m VEGFR expressed by MS1 murine endothelial cells (FIG. 8B).

Mab 147 inhibit VEGFR-2 mediated signal transduction, as indicated by reduced phosphorylation of KDR and p42/44 in KDR-PAE cells (FIG. 9A) and in HUVEC cells (FIG. 9B). Mab 106 and Mab 147 inhibit proliferation of KDR-PAE cells (FIG. 10A), as well as inhibit VEGF-induced migration of KDR-PAE cells (FIG. 10B). The effect of Mab 147 on inhibition of VEGF-induced migration by KDR-PAE cells is also shown in FIG. 11.

Mab 147 also inhibits VEGFR-2 mediated signal transduction in murine EOMA cells, as indicated by reduced phosphorylation of m VEGFR2 (FIG. 12A). FACS studies demonstrated that Mab 147 has increased binding to EOMA cells by comparison to control antibodies (FIG. 12B).

---

We claim:

1. A nucleic acid encoding an antibody or antigen binding fragment thereof that binds to human VEGFR2, the antibody or antigen binding fragment thereof comprising a heavy chain variable domain, which comprises a CDR1H, a CDR2H, and a CDR3H sequence, and a light chain variable domain, which comprises a CDR1L, a CDR2L, and a CDR3L sequence wherein:

(a) the CDR1H sequence is GFTFSWYVMS (amino acids 26-35 of SEQ ID NO: 208),
    the CDR2H sequence is SIYPQGGATNYADSVKG (SEQ ID NO: 239),
    the CDR3H sequence is GNYFDY (SEQ ID NO: 241),
    the CDR1L sequence is RASQSVSSNYFG (SEQ ID NO: 245),
    the CDR2L sequence is GASSRAT (SEQ ID NO: 246), and
    the CDR3L sequence is QQHDSSPLS (SEQ ID NO: 248);

(b) the CDR1H sequence is GFTFSWYVMG (SEQ ID NO: 237),
    the CDR2H sequence is SIYPSGGATNYADSVKG (SEQ ID NO: 240),
    the CDR3H sequence is GNYLDY (SEQ ID NO: 242),
    the CDR1L sequence is RASQSVSSNYFG (SEQ ID NO: 245),
    the CDR2L sequence is GASSRAT (SEQ ID NO: 246), and
    the CDR3L sequence is QQFDSSPLS (SEQ ID NO: 249);

(c) the CDR1H sequence is GFTFSWYVMG (SEQ ID NO: 237),
    the CDR2H sequence is SIYPSGGATNYADSVKG (SEQ ID NO: 240),
    the CDR3H sequence is GPYLDY (SEQ ID NO: 243),
    the CDR1L sequence is RASQSVSSNYFG (SEQ ID NO: 245),
    the CDR2L sequence is GASSRAT (SEQ ID NO: 246), and the CDR3L sequence is QQFDSSPLT (SEQ ID NO: 250); or (d) the CDR1H sequence is GFTFSWYVMG (SEQ ID NO: 237),
    the CDR2H sequence is SIYPSGGATNYADSVKG (SEQ ID NO: 240),
    the CDR3H sequence is GSYLDY (SEQ ID NO: 244),
    the CDR1L sequence is RASQSVSSNYFG (SEQ ID NO: 245),
    the CDR2L sequence is GASSRAT (SEQ ID NO: 246), and
    the CDR3L sequence is QQFDSSPLT (SEQ ID NO: 250).

2. The nucleic acid of claim 1, wherein:

(a) the heavy chain variable domain has a sequence that is at least 85% identical to the sequence of SEQ ID NO: 208, and the light chain variable domain has a sequence that is at least 85% identical to the sequence of SEQ ID NO: 212;

(b) the heavy chain variable domain has a sequence that is at least 85% identical to the sequence of SEQ ID NO: 216, and the light chain variable domain has a sequence that is at least 85% identical to the sequence of SEQ ID NO: 220;

(c) the heavy chain variable domain has a sequence that is at least 85% identical to the sequence of SEQ ID NO: 224, and the light chain variable domain has a sequence that is at least 85% identical to the sequence of SEQ ID NO: 228; or (d) the heavy chain variable domain has a sequence that is at least 85% identical to the sequence of SEQ ID NO: 232, and the light chain variable domain has a sequence that is at least 85% identical to the sequence of SEQ ID NO: 236.

3. The nucleic acid of claim 1, wherein:

(a) the heavy chain variable domain has a sequence that is SEQ ID NO: 208, and the light chain variable domain has a sequence that is SEQ ID NO: 212;

(b) the heavy chain variable domain has a sequence that is SEQ ID NO: 216, and the light chain variable domain has a sequence that is SEQ ID NO: 220;

(c) the heavy chain variable domain has a sequence that is SEQ ID NO: 224, and the light chain variable domain has a sequence that is SEQ ID NO: 228; or (d) the heavy chain variable domain has a sequence that is SEQ ID NO: 232, and the light chain variable domain has a sequence that is SEQ ID NO: 236.

4. The nucleic acid of claim 1, wherein the antibody or antigen binding fragment thereof has isotype IgG.

5. The nucleic acid of claim 1, wherein the antibody or antigen binding fragment thereof is an scFv, Fv, Fab', Fab, F(ab')2, or diabody.

6. The nucleic acid of claim 1, wherein the antibody or antigen binding fragment thereof binds to human VEGFR2 and murine VEGFR2.

\*    \*    \*    \*    \*